United States Patent [19]

Carter

[11] Patent Number: 4,746,358

[45] Date of Patent: May 24, 1988

[54] PHENYL-SUBSTITUTED SULFONAMIDES

[75] Inventor: Linda G. Carter, Wilmington, Del.

[73] Assignee: E. I. Du Pont de Nemours and Company, Wilmington, Del.

[21] Appl. No.: 7,912

[22] Filed: Jan. 27, 1987

Related U.S. Application Data

[60] Division of Ser. No. 828,249, Feb. 11, 1986, Pat. No. 4,659,368, which is a continuation-in-part of Ser. No. 649,542, Sep. 11, 1984, Pat. No. 4,595,407, which is a division of Ser. No. 437,366, Nov. 1, 1982, Pat. No. 4,502,882, which is a continuation-in-part of Ser. No. 363,379, Mar. 29, 1982, abandoned.

[51] Int. Cl.$^4$ .................... A01N 43/66; C07D 407/12
[52] U.S. Cl. .......................................... 71/93; 71/90; 71/91; 544/212; 544/207; 544/209; 544/321; 544/324; 544/331
[58] Field of Search ................. 71/93; 544/212, 207, 544/209; 71/90, 91

[56] References Cited

U.S. PATENT DOCUMENTS

| | | | |
|---|---|---|---|
| 4,127,405 | 11/1978 | Levitt | 71/93 |
| 4,391,627 | 7/1983 | Levitt | 71/90 |
| 4,465,506 | 8/1984 | Welch | 71/92 |
| 4,502,882 | 3/1985 | Carter | 71/93 |
| 4,514,211 | 4/1985 | Rorer | 71/92 |
| 4,595,407 | 6/1986 | Carter | 71/93 |

Primary Examiner—John M. Ford

[57] ABSTRACT

Novel N-[pyrimidin-2-yl]- and [triazin-2-yl]-aminocarbonyl]-1,3-benzodioxolesulfonamides and 1,4-benzodioxansulfonamides are useful as plant growth regulants and in particular as herbicides.

10 Claims, No Drawings

PHENYL-SUBSTITUTED SULFONAMIDES

CROSS REFERENCE TO RELATED APPLICATION

This application is a division of U.S. Ser. No. 828,249 filed Feb. 11, 1986 now U.S. Pat. No. 4,659,368; which in turn is a continuation-in-part of Ser. No. 649,542 filed Sept. 11, 1984 now U.S. Pat. No. 4,595,407; which is a division of Ser. No. 437,366 filed Nov. 1, 1982 now U.S. Pat. No. 4,502,882; which is a continuation-in-part of U.S. Ser. No. 363,379 filed Mar. 29, 1982 which is now abandoned.

BACKGROUND OF THE INVENTION

This invention relates to benzodioxolesulfonamides and benzodioxansulfonamides which are useful as plant growth regulants and in particular as herbicides.

*Chem. Ber.*, 105, 2791 (1972) describes the preparation of N-butylcarbamoyl-p-toluenesulfamate, but does not claim utility as a pesticide:

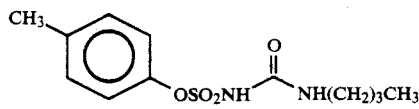

German Pat. No. 940,292 describes the preparation of N-[arylcarbamoyl]arylsulfamides and claims utility as textile assistants, pharmaceuticals and pesticides:

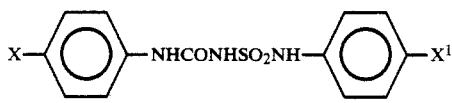

wherein each of X and X¹ is H, or each is ethoxy.

Netherlands Pat. No. 121,788, published Sept. 15, 1966, teaches the preparation of compounds of Formula (i), and their use as general or selective herbicides:

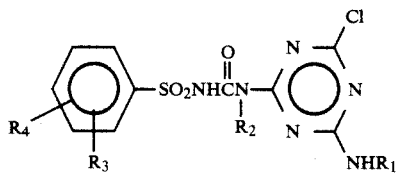

wherein
R₁ and R₂ may independently be alkyl of 1–4 carbon atoms; and
R₃ and R₄ may independently be hydrogen, chlorine or alkyl of 1–4 carbon atoms.

French Pat. No. 1,468,747 discloses the following para-substituted phenylsulfonamides, useful as antidiabetic agents:

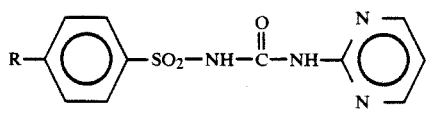

wherein
R = H, halogen, CF₃ or alkyl.

Logemann et al., Chem. Ab., 53, 18052 g (1959), disclose a number of sulfonamides, including uracil derivatives and those having the formula:

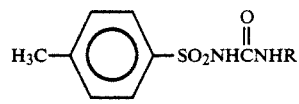

wherein
R is butyl, phenyl or

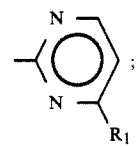

and
R₁ is hydrogen or methyl.

When tested for hypoglycemic effect in rats (oral doses of 25 mg/100 g), the compounds in which R is butyl and phenyl were most potent. The others were of low potency or inactive.

Wojciechowski, J. Acta. Polon. Pharm. 19, p. 121–5 (1962) [Chem. Ab., 59 1633 e] describes the synthesis of N-[(2,6-dimethoxypyrimidin-4-yl)aminocarbonyl]-4-methylbenzenesulfonamide:

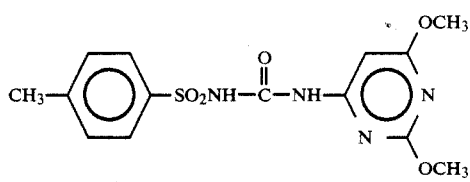

Based upon similarity to a known compound, the author predicted hypoglycemic activity for the foregoing compound.

Undesired vegetation can cause substantial damage to useful crops, especially agricultural products that satisfy man's basic food and fiber needs, such as cotton, rice, corn, wheat, soybean and the like.

Although a wide variety of materials are available which can be used for killing or inhibiting (controlling) the growth of undesired vegetation the need exists for still more effective herbicides that destroy or control weeds without causing significant damage to useful crops.

SUMMARY OF THE INVENTION

This invention relates to novel compounds of Formula I and Formula II, suitable agricultural compositions containing them, and their method-of-use as general and selective pre-emergence and post-emergence herbicides.

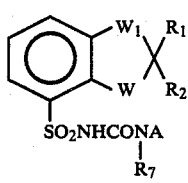 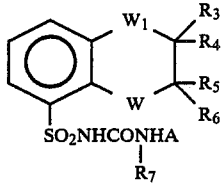 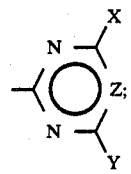

wherein
W is O, S, SO or $SO_2$;
$W_1$ is O, S, SO or $SO_2$;
$R_1$ is H or $CH_3$;
$R_2$ is H or $C_1$–$C_4$ alkyl;
$R_3$, $R_4$, $R_5$, $R_6$ and $R_7$ are independently H or $CH_3$;
A is

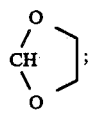 

X is $CH_3$, $OCH_3$, or Cl;
Y is $C_2H_5$, $CH_3$, $OCH_3$, $OC_2H_5$, $CH_2OCH_3$, $NH_2$, $NHCH_3$, $SCH_3$, $N(CH_3)_2$, $CH(OCH_3)_2$ or $$\begin{matrix} & O \\ & / \\ CH & \\ & \backslash \\ & O \end{matrix} \quad ;$$

Z is CH or N;
$X_1$ is $CH_3$ or $OCH_3$;
G is O or $CH_2$;
$X_2$ is $C_1$–$C_3$ alkyl or $CH_2CF_3$; and
$Y_2$ is $OCH_3$, $OC_2H_5$, $SCH_3$ or $SC_2H_5$;
provided that when X is Cl, then Z is CH and Y is $NH_2$, $NHCH_3$, $N(CH_3)_2$, or $OCH_3$; and their agriculturally suitable salts.

Preferred for reasons of higher herbicidal activity and/or more favorable ease of synthesis are:

(1) Compounds of Formula I where W and $W_1$ have identical values.

(2) Compounds of Formula II where W and $W_1$ have identical values.

(3) Compounds of Preferred 1 where A is

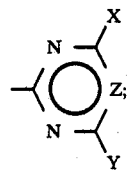

and $R_7$ is H.

(4) Compounds of Preferred 2 where A is (image showing heterocyclic structure with X, Y, Z)

and $R_7$ is H.

(5) Compounds of Preferred 3 where $R_2$ is H or $CH_3$.
(6) Compounds of Preferred 5 where Y is $CH_3$ or $OCH_3$.
(7) Compounds of Preferred 6 where W and $W_1$ are O or S.
(8) Compounds of Preferred 6 where W and $W_1$ are SO or $SO_2$.

Specifically Preferred are:
N-[(4-methoxy-6-methylpyrimidin-2-yl)aminocarbonyl]-2,2-dimethyl-1,3-benzodioxole-4-sulfonamide;
N-[(4,6-dimethylpyrimidin-2-yl)aminocarbonyl]-2,2-dimethyl-1,3-benzodioxole-4-sulfonamide;
N-[(4,6-dimethoxypyrimidin-2-yl)aminocarbonyl-2,2-dimethyl-1,3-benzodioxole-4-sulfonamide;
N-[(4,6-dimethoxy-1,3,5-triazin-2-yl)aminocarbonyl]-2,2-dimethyl-1,3-benzodioxole-4-sulfonamide;
N-[(4-methoxy-6-methyl-1,3,5-triazin-2-yl)aminocarbonyl]-2,2-dimethyl-1,3-benzodioxole-4-sulfonamide; and
N-[(4,6-dimethyl-1,3,5-triazin-2-yl)aminocarbonyl]-2,2-dimethyl-1,3-benzodioxole-4-sulfonamide.

DETAILED DESCRIPTION OF THE INVENTION

Synthesis

The compounds of Formulae (I) and (II) can be prepared by one of the methods described below in Equations 1 and 2.

As shown in Equation 1, compounds of Formula I can be prepared by reaction of the sulfonamide of Formula (III) with an appropriate methyl heterocyclic carbamate of Formula (IV) in the presence of an equimolar amount of trimethylaluminum, wherein $R_1$, $R_2$, $R_7$, $W_1$, W and A are as previously defined.

Equation 1

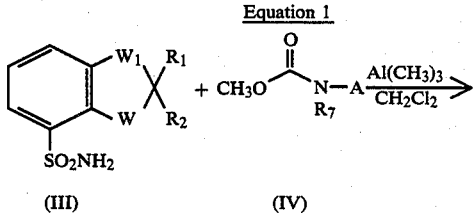

(III)                (IV)

-continued

Equation 1

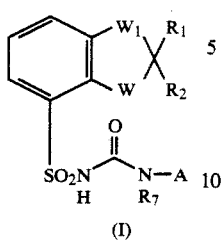

(I)

The reaction of Equation 1 takes place in methylene chloride at reflux or ambient temperature for 16-96 hours under an inert atmosphere. The product can be isolated after the sequential addition of aqueous acetic acid and hydrochloric acid to the reaction mixture followed by the partitioning of the product into methylene chloride. The product can be purified via crystallization from such solvents as n-butyl chloride, diethyl ether, tetrahydrofuran, or methylene chloride or by silica medium pressure liquid chromatography.

As shown in Equation 2, compounds of Formula (II) can be prepared by reaction of the sulfonamide of Formula (V) with an appropriate methyl heterocyclic carbamate of Formula (IV) in the presence of an equimolar amount of trimethylaluminum, wherein $R_3$ to $R_7$, $W_1$, W and A are as previously defined.

Equation 2

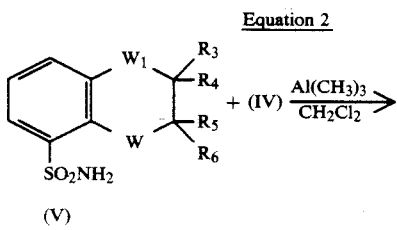

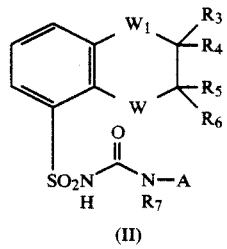

(II)

The reaction of Equation 2 is performed in methylene chloride at reflux for 16-72 hours under an inert atmosphere. The product is isolated upon sequential addition of aqueous acetic acid and hydrochloric acid to the reaction mixture followed by the partitioning of the product into methylene chloride. The product is purified via crystallization from solvents such as n-butyl chloride, diethyl ether or methylene chloride or by silica medium pressure liquid chromatography.

As shown in Equation 3, the sulfonamides of Formula (III) wherein $R_1$ and $R_2$ are not H and $W_1$ and W are as previously defined can be prepared from the appropriate 1,3-benzodioxole of Formula (VI) via the lithium sulfinate of Formula (VII).

Equation 3

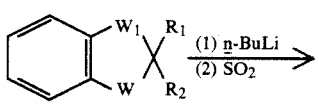

(VI)

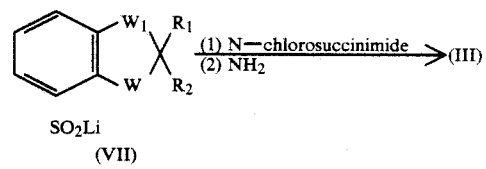

SO$_2$Li (VII)

Reaction of the arene of Formula (VI) with a butyllithium in ether or tetrahydrofuran in the presence or absence of a chelating agent such as N,N,N',N'-tetramethylethylene diamine at $-78°$ to ambient temperature for 2-16 hours followed by contacting with sulfur dioxide at $-78°$ to ambient temperature until no further exotherm is noted results in the formation of the lithium sulfinate of Formula (VII). The 4-sulfonamide of Formula (III) is isolated in a two-step sequence upon reaction of the lithium sulfinate of Formula (VII) with N-chlorosuccinimide in glacial acetic acid at $15°$ to $25°$ C. followed by contacting the product with an aqueous solution to give the sulfonyl chloride. The sulfonyl chloride is then contacted with excess ammonia in diethyl ether or methylene chloride at $10°-20°$ C. The 1,3-benzodioxoles of Formula (VI) wherein $W_1$ and W are O can be prepared according to the procedures of C. M. Yoder and J. J. Zuckerman, *J. Heterocycl. Chem.*, 1967, 4, 166; E. R. Cole et al., *Aust. J. Chem.*, 1980, 33, 675; and W. Bonthrone and J. W. Cornforth, *J. Chem. Soc. (C)*, 1969, 1202.

The 1,3-benzodithioles and the benzoxathioles of Formula VI, wherein $W_1$ and W are O or S, can be prepared according to the procedures suggested by S. Cabiddu et al. *Synthesis*, 1976, 797; G. Scherowsky and J. Weiland, *Chem. Ber.* 1974, 3155; and A. Pelter et al. *Tetrahed. Lett.* 1978, 26, 2345. Compounds of Formula (VI) wherein $W_1$ and/or W are higher oxidation states of sulfur can be prepared from compounds of Formula (VI), wherein $W_1$ and W are not both O, or $SO_2$ or a combination of O and $SO_2$, upon treatment with the appropriate equivalents of 30% hydrogen peroxide in acetic acid at ambient temperature or reflux for 4-17 hours as suggested by W. Parham et al. *J. Am. Chem. Soc.*, 1953, 75, 1953; permanganate treatment according to the procedure of D. Greenwood and H. Stevenson, *J. Chem. Soc.*, 1953, 1514, or via periodate oxidation. Mixtures of oxidized benzodithioles and benzoxathioles, obtained by these procedures, can be purified via fractional crystallization or column chromatography.

An alternative route to the preparation of the 4-sulfonamide of Formula (III), wherein $W_1$ and W are O or S and $R_1$ and $R_2$ are as previously defined, including H, from bromobenzene of Formula (VIII) is illustrated below in Equation 4.

Equation 4

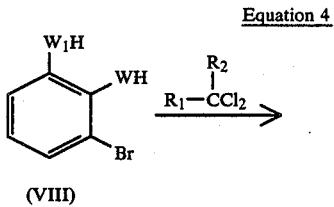

(VIII)

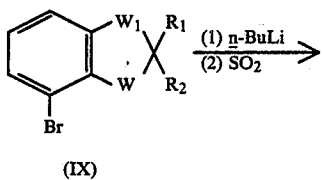

(IX)

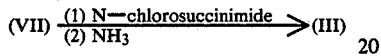

The 3-bromocatechol of Formula (VIII) can be prepared according to the procedure of H. S. Mason, *J. Am. Chem. Soc.* 1947, 69, 2241. The 4-bromo-1,3-benzodioxole of Formula (IX) can be prepared from 3-bromocatechol of Formula (VIII) via procedures similar to those described by W. Bonthrone and J. W. Cornforth, *J. Chem. Soc. (C)*, 1969, 1202. The bromo thiocatechols and bromothiophenols of Formula (VIII) can be prepared according to the procedures of L. Horner et al., *Phosphorus and sulfur*, 1982, 2, 353 and A. Ferretti; *Org. Synth.*, 1973, *Coll Vol V*, 419. The 4-bromo-1,3-benzodithioles and the bromoxathioles of Formula (IX) can be prepared according to the procedure of S. Cabiddu et al., *Synthesis*, loc. cit. A metal-halogen interchange of the bromo compound of Formula (IX) in an ether solution at $-70°$ to $-78°$ C. using 1.1 equivalents of n-butyllithium followed by sulfur dioxide contact at $-45°$ to $-78°$ C. can afford the lithium sulfinate of Formula (VII). The sulfonamide of Formula (III), can be prepared from the sulfinate of Formula (VII) by the N-chlorosuccinimide, ammonia procedures shown in Equation 3.

An alternative route to the preparation of 4-sulfonamides of Formula (III) wherein $W_1$ and W can be higher oxidation states of sulfur is illustrated in Equation 5.

Equation 5

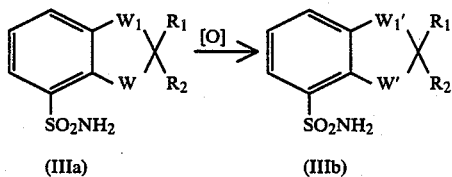

Reaction of the 4-sulfonamides of Formula (IIIa) wherein $W_1$ and W are not both O or $SO_2$ or a combination of O and $SO_2$ and $R_1$ and $R_2$ are as previously defined, with 30% hydrogen peroxide as suggested by W. Parham et al., *J. Am. Chem. Soc.*, loc. cit.; permangonate reaction according to the procedure of D. Greenwood and H. Stevenson, *J. Chem. Soc.*, loc. cit.; or periodate reaction may afford the 4-sulfonamides of Formula (IIIb) wherein $W_1'$ and W' may be higher oxidation states of sulfur. Mixtures of oxidized sulfonamides, obtained by these procedures, can be purified via fractional crystallization or column chromatography.

As illustrated below in Equation 6, 5-sulfonamides of Formula (V), wherein $R_3$ through $R_6$ are not H and $W_1$ and W are as previously defined can be prepared from arenes of Formula (X) via the lithium sulfinate of Formula (XI) according to the procedures of Equation 3.

Equation 6

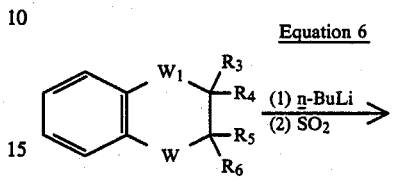

(X)

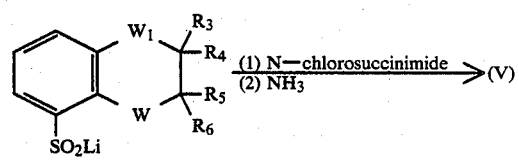

(XI)

the 1,4-benzodioxans of Formula (X) wherein $W_1$ and W are O can be prepared according to the procedures of Schroth et al., *Z. Chem.*, 1967, 7, 152 and B. N. Ghosh, *J. Chem. Soc.*, 1915, 107, 1591, W. Adam et al., *Synthesis*, 1982, 322, A. Bashall and J. Collins, *Tetrahed. Lett.*, 1975, 40, 3489.

The 1,4-benzodithians and the benzoxathians of Formula (X), wherein $W_1$ and W are both S or a combination of S and O can be prepared according to the procedures of W. Parham et al., *J. Am. Chem. Soc.*, loc. cit. and S. Cabiddu et al., *Synthesis*, loc. cit. Compounds of Formula (X) wherein $W_1$ and/or W can include higher oxidation states of sulfur can be prepared upon hydrogen peroxide, permanganate or periodate treatment as suggested by W. Parham et al., *J. Am. Chem. Soc.*, loc. cit. and D. Greenwood and H. Stevenson, *J. Chem. Soc.*, loc. cit. Mixtures of oxidized benzodithians and benzoxathians, obtained by these procedures, can be purified via fractional crystallization or column chromatography.

An alternative route to the preparation of the 5-sulfonamides of Formula (V), wherein $W_1$ and W are O or S and $R_3$ through $R_6$ are as previously defined and include H from the bromobenzenes of Formula (VIII) via the cyclic arene of Formula (XII) and lithium sulfonate of Formula (XI) according to the procedures of Equation 4 is illustrated in Equation 7.

Equation 7

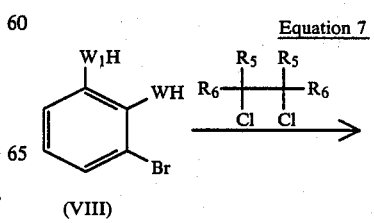

(VIII)

-continued

*Equation 7*

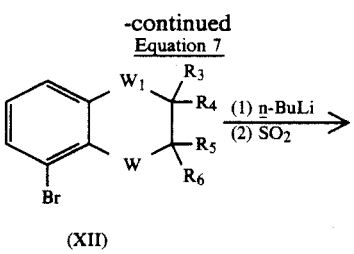

(XI) $\xrightarrow[(2)\ NH_3]{(1)\ N-chlorosuccinimide}$ (V)

The preparation of the bromobenzenes is illustrated in the discussion of Equation 4. The bromobenzodioxans of Formula (XII) can be prepared according to the procedures of Schroth et al., *Z. Chem.*, loc. cit. and B. Ghosh, *J. Chem. Soc.*, loc. cit. The bromobenzodithians and bromobenzoxathians of Formula (XII) can be prepared according to the procedures of the benzodithians and benzoxathians of Formula (X), discussed in Equation 6.

As illustrated in Equation 8, the 5-sulfonamides of Formula (Vb) wherein $R_3$ through $R_6$ are as previously defined and $W_1$ and W may include higher oxidation states of sulfur, may be prepared via the 5-sulfonamides of Formula (Va), wherein $W_1$ and W are not both O or $SO_2$ or a combination of O and $SO_2$ and $R_3$ through $R_6$ are as previously defined, according to the procedures of Equation 5.

*Equation 8*

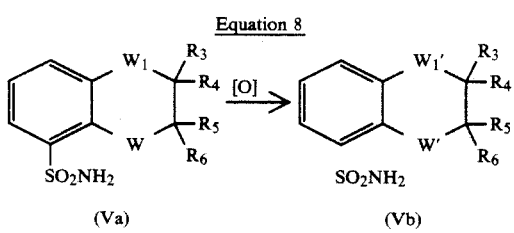

Equation 9 illustrates the preparation of the requisite methyl heterocyclic carbamates of Formula (IV) utilized in Equations 1 and 2, wherein $R_7$ and A are as previously defined.

*Equation 9*

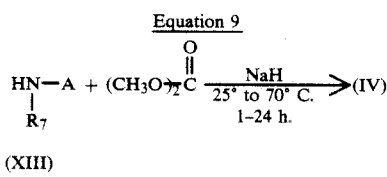

According to Equation 9, a heterocyclic amine of Formula (XIII) is contacted with two equivalents of sodium hydride and excess dimethylcarbonate to form (IV). This reaction is performed in an inert solvent such as tetrahydrofuran at 25° to 70° C. for 1 to 24 hours. The product is isolated by (a) addition of two equivalents of concentrated hydrochloric acid and aqueous saturated sodium chloride and (b) separation of the organic phase followed by concentration to dryness in vacuo.

The synthesis of the pyrimidine and triazine amines of Formula (XIII) has been reviewed in "The Chemistry of Heterocyclic Compounds," a series published by Interscience Publ., New York and London. The 2-aminopyrimidines are described by D. J. Brown in "The Pyrimidines," Vol. XXVI of this series. The 2-amino-1,3,5-triazines can be prepared according to methods described by E. M. Smolin and L. Rapaport in "s-Triazines and Derivatives," Vol. XIII of the same series. The synthesis of triazines is also described by F. C. Schaefer, U.S. Pat. No. 3,154,547 and by K. R. Huffman and F. C. Schaefer, *J. Org. Chem.*, 1963, 28, 1816.

Braker, Sheehan, Spitzmiller and Lott, *J. Am. Chem. Soc.*, 69, 3072 (1947) describe the preparation of 6,7-dihydro-4-methoxy-5H-cyclopentapyrimidin-2-amine by the following sequence of reactions.

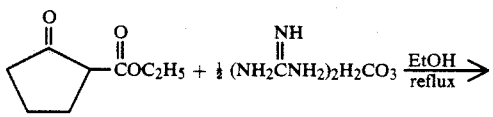

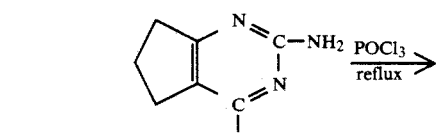

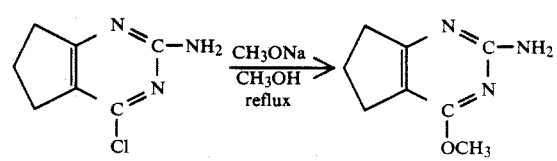

6,7-dihydro-4-methoxy-
5H—cyclopenta-
pyrimidin-2-amine.

An analogous sequence of reactions can be used to prepare 5,6,7,8-tetrahydro-4-methoxy-2-quinazolinamine.

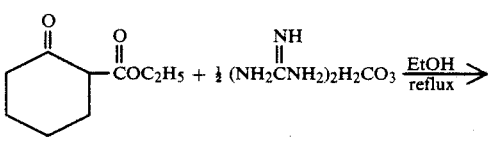

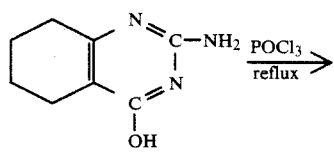

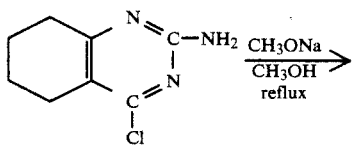

5,6,7,8-tetrahydro-4-
methoxy-2-quinazolinamine.

Mitter and Bhattacharya, *Quart. J. Indian Chem. Soc.*, 4, 152 (1927) describe the preparation of 5,6,7,8-tetrahydro-4-methyl-2-quinazolinamine as follows:

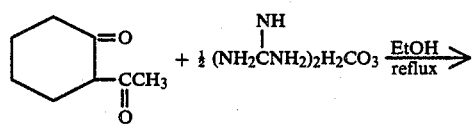

5,6,7,8-tetrahydro-4-methyl-2-quinazolinamine.

Similarly, 6,7-dihydro-4-methyl-5H-cyclopentapyrimidin-2-amine can be prepared by the condensation of 2-acetylcyclopentanone with guanidine carbonate, but preferably under acidic conditions, removing the water formed.

6,7-dihydro-4-methyl-5H—cyclopentapyrimidin-2-amine.

Shrage and Hitchings, *J. Org. Chem.*, 16, 1153 (1951) describe the preparation of 5,6-dihydro-4-methylfuro[2,3-d]pyrimidin-2-amine by the following sequence of reactions An analogous sequence of reactions can be used to prepare 6,7-dihydro-4-methyl-5H-pyrano[2,3-d]pyrimidin-2-amine starting with 2-acetyl-δ valerolactone [Korte and Wusten, *Tetrahedron* 19, 1423 (1963)].

5,6-Dihydro-4-methoxyfuro[2,3-d]pyrimidin-2-amine can be prepared by the method of Braker et al., *J. Am. Chem. Soc.*, 69, 3072 (1947), using 5,6-dihydro-4-hydroxyfuro[2,3-d]pyrimidin-2-amine [Svab, Budesinski and Vavrina, *Collection Czech. Chem. Commun.*, 32, 1582 (1967)].

-continued

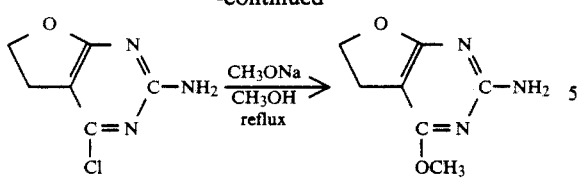

An analogous sequence of reactons can be used to prepare 6,7-dihydro-4-methoxy-5H-pyrano[2,3-d]pyrimidin-2-amine.

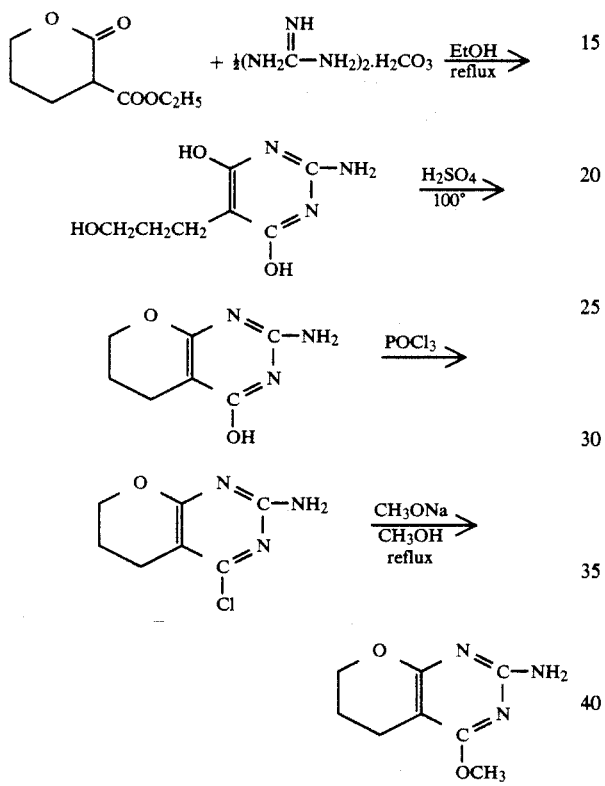

Caldwell, Kornfeld and Donnell, *J. Am. Chem. Soc.*, 63, 2188 (1941), describe the preparation of 6,7-dihydro-5H-cyclopentapyrimidin-2-amine by the following sequence of reactions.

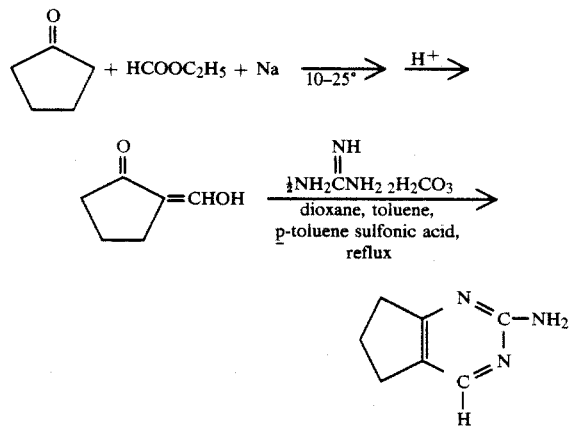

Fissekis, Myles and Brown, *J. Org. Chem.*, 29, 2670 (1964), describe the preparation of 2-amino-4-hydroxy-5-(2-hydroxyethyl)pyrimidine which can be converted to 5,6-dihydrofuro[2,3-d]pyrimidin-2-amine by dehydration.

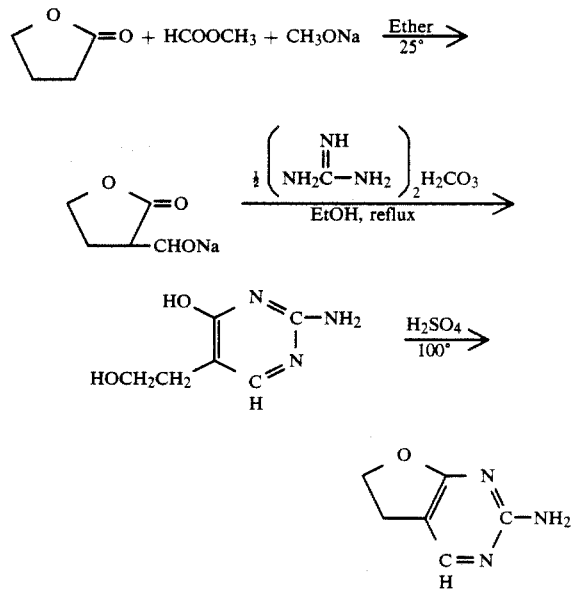

Preparations of 3-amino-1,2,4-triazoles are known in the art and 1,2,4-triazoles are reviewed in *The Chemistry of Heterocyclic Compounds* "Triazoles 1,2,4" (John Wiley and Sons, New York, 1981). Commonly used starting materials containing nitrogen are N-aminoguanidine, hydrazine, alkylhydrazines, cyanamide, ethyl cyanoacetimidate, dimethyl cyanodithioimidocarbonate, dimethyl cyanoimidocarbonate, ethoxymethylenecyanamide, and acylhydrazines. Some literature syntheses are illustrated below. Using these techniques or suitable modifications that would be apparent to one skilled in the art, the 3-amino-1,2,4-triazole intermediates can be readily prepared.

Heating equimolar amounts of ethyl propionimidate hydrochloride and N-aminoguanidine nitrate in pyridine gives 3-amino-5-ethyltriazole; German Pat. No. 1,073,499 (1960); *Berichte*, 96, 1064 (1963).

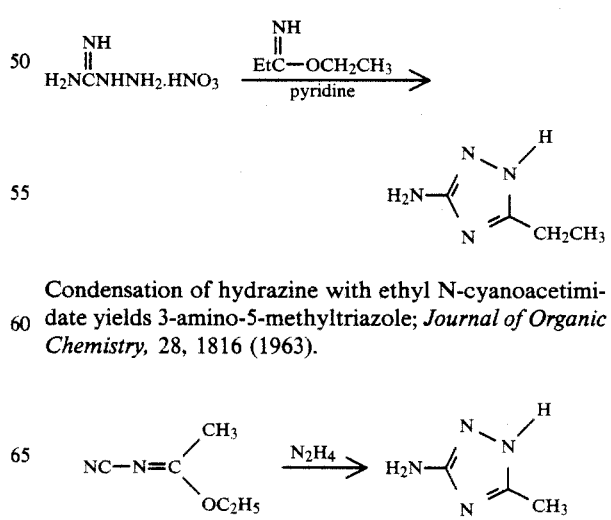

Condensation of hydrazine with ethyl N-cyanoacetimidate yields 3-amino-5-methyltriazole; *Journal of Organic Chemistry*, 28, 1816 (1963).

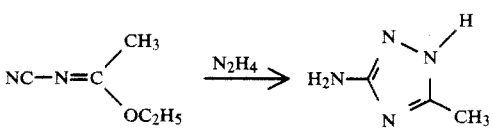

Trifluoromethyl-3-aminotriazole can be obtained by thermal dehydration of the hydrazide of trifluoroacetic acid. *Zh. Obshch. Khim.*, 39, 2525 (1969); *Chemical Abstracts*, 72: 78954v (1970).

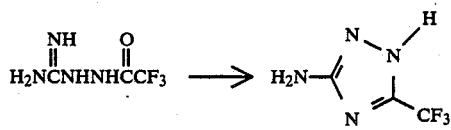

U.S. Pat. No. 2,835,581 (1958) teaches the preparation of 3-amino-5-(hydroxymethyl)triazole from N-aminoguanidine and glycolic acid and British Pat. No. 736,568 (1955) describes the synthesis of 3-amino-5-mercaptotriazole.

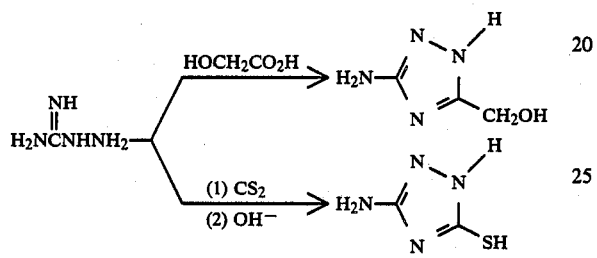

Condensing hydrazine with dimethyl cyanodithioimidocarbonate in acetonitrile gives 3-amino-5-methylthio-1,2,4-triazole while reaction of hydrazine with dimethyl N-cyanoimidocarbonate produces 3-amino-5-methoxy-1,2,4-triazole; *Journal of Organic Chemistry*, 39, 1522 (1974).

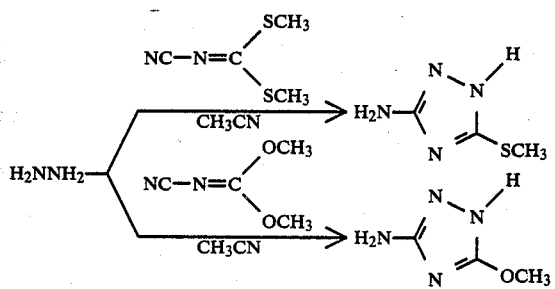

Reaction of substituted hydrazines with N-cyanothioimidocarbonates (prepared according to the procedure given in D. M. Wieland, Ph.D. Thesis, 1971, pp. 123-124) yields disubstituted aminotriazoles as shown below.

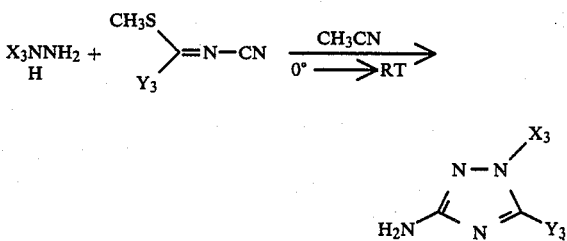

wherein
$X_3$ is $C_1$-$C_3$ alkyl; and
$Y_3$ is $C_1$-$C_2$ alkoxy.

Furo[2,3-d]pyrimidine Intermediates

The pyrimidine intermediates XIV in which Z is hydrogen or methyl and X is methyl have been reported in the literature by E. Bisagni et al., [*Bul. Soc. Chim. Fr.*, 803 (1969)]. An apparently more efficient procedure is depicted in Equation 10 for the case in which Z is hydrogen.

Equation 10

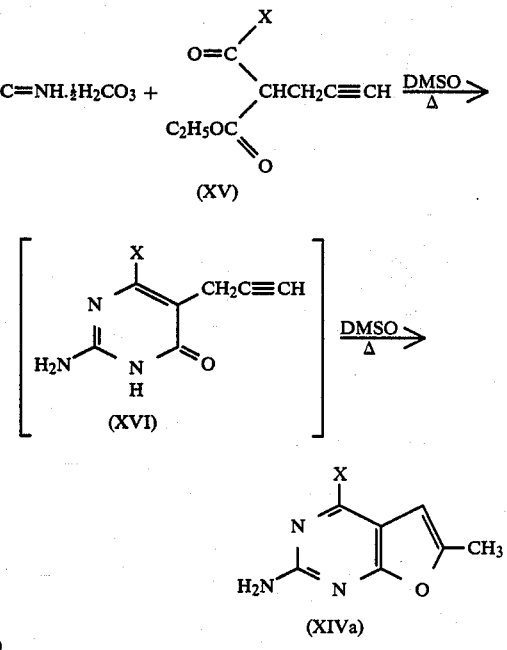

(Z = H)
X = $CH_3$ or $C_2H_5$

The keto-ester precursors XV are prepared by well known literature methods, e.g., J. F. Tinker and T. E. Whatmough, *J. Amer. Chem. Soc.*, 74, 5235 (1952).

Treatment of XIV with an excess of quanidine carbonate in an organic solvent, preferably a polar aprotic solvent such as dimethylsulfoxide (DMSO), dimethylformamide (DMF), or N,N-dimethylacetamide, at a temperature of 80° to 200°, preferably 100° to 160°, ambient pressure and preferably under an inert atmosphere, yields both XIVa and XVI as products. The products are isolated upon dilution of the reaction mixture with, for example, acetone and water successively. Higher reaction temperatures and longer reaction times (e.g., in DMSO at 130°-150° for 2 to 8 hours) favor the production of the furopyrimidine XIV over the uncyclized pyrimidine XVI.

Agriculturally suitable salts of compounds of Formulae (I) and (II) are also useful herbicides and can be prepared in a number of ways known to the art. For example, metal salts can be made by contacting compounds of Formulae (I) and (II) with a solution of an alkali or alkaline earth metal salt having a sufficiently basic anion (e.g. hydroxide, alkoxide, carbonate or hydroxide). Quaternary amine salts can be made by similar techniques.

Salts of compounds of Formula (I) or (II) can also be prepared by exchange of one cation to another. Cationic exchange can be effected by direct treatment of an aqueous solution of a salt of a compound of Formula (I) or (II) (e.g., alkali metal or quaternary amine salt) with a solution containing the cation to be exchanged. This method is most effective when the desired salt containing the exchanged cation is insoluble in water, e.g., a copper salt, and can be separated by filtration.

Exchange may also be effected by passing an aqueous solution of a salt of a compound of Formula (I) or (II) (e.g., an alkali metal or quaternary amine salt) through a column packed with a cation exchange resin containing the cation to be exchanged. In this method, the cation of the resin is exchanged for that of the original salt and the desired product is eluted from the column. This method is particularly useful when the desired salt is water-soluble, e.g., a potassium, sodium or calcium salt.

Acid addition salts, useful in this invention, can be obtained by reacting a compound of Formula (I) or (II) with a suitable acid, e.g., p-toluenesulfonic acid, trichloroacetic acid or the like.

The compounds of this invention and their preparation are further illustrated by the following examples wherein temperatures are given in degrees centigrade and all parts are by weight unless otherwise indicated.

EXAMPLE 1

2,2-Dimethyl-1,3-benzodioxole-4-sulfonamide

To a solution of 25 g 2,2-dimethyl-1,3-benzodioxole [prepared according to the procedure of C. M. Yoder and J. J. Zuckerman, *J. Heterocycl. Chem.*, 1967, 4, 166] in 300 ml ether and 200 ml tetrahydrofuran at ambient temperature under nitrogen was added dropwise, 105 ml n-butyllithium (1.6N in hexane). The temperature was maintained at $\approx 25°$ C. with ice bath cooling during the addition. The reaction mixture was stirred 16 hours at room temperature. Excess sulfur dioxide was bubbled through the reaction mixture, kept at $\approx 25°$ C. with cooling, until no further exotherm was noted. The reaction mixture was stirred at room temperature for 18 hours followed by the addition of 10 ml isopropyl alcohol. The reaction mixture was concentrated and crystallized from ether/tetrahydrofuran to give 20.5 g tan solid. The solid was added to 150 ml acetic acid and the resultant mixture was cooled to 20° C. A slurry of 12.4 g N-chlorosuccinimide in 75 ml acetic acid was added portionwise with cooling to maintain the reaction mixture between 20° and 25° C. The reaction mixture was stirred for three hours at ambient temperature and the solvent was removed under reduced pressure to give an oil. The oil was dissolved in methylene chloride and washed with water. The aqueous phase was washed with methylene chloride. The organic phases were combined, dried and the solvent removed under reduced pressure to give an oil which was dissolved in 250 ml ether and cooled to 10° C. Excess ammonia (anhy.) was bubbled through the reaction mixture using ice bath cooling. The reaction mixture was warmed to ambient temperature, stirred for 1 hour, and 150 ml ether was added. The reaction mixture was washed with water, dried and concentrated under reduced pressure to give 8.1 g tan oily solid, m.p. 100°-112° C. IR (NH) 3240 (NH), 3420 (NH) cm$^{-1}$.

$^1$HNMR (DMSO-d$_6$): 1.7 (s, 6H); and 6.5-7.4 (m, 5H).

EXAMPLE 2

1,3-Benzodioxole-4-sulfonamide

To a solution of 18.8 g 3-bromocatechol (prepared according to the procedure of H. S. Mason, *J. Am. Chem. Soc.*, 1947, 69, 2241) and 10 g methylene chloride in 150 ml dimethyl sulfoxide at ambient temperature under nitrogen is added 8.3 g of sodium hydroxide (powdered). The reaction mixture is heated at 120° C. for 2 hours. Steam distillation gives 13.5 g of the solid, 4-bromo-1,3-benzodioxole. The solid is dissolved in 200 ml of tetrahydrofuran under a nitrogen atmosphere, cooled to −78° C. and treated sequentially with 42.2 ml n-butyllithium (1.6N in hexane) for 16 hours and excess sulfur dioxide until no further exotherm is noted. The reaction mixture is contacted with 10 ml isopropyl alcohol, concentrated in vacuo and crystallized from ether/tetrahydrofuran to give a solid. The solid is added to 150 ml of acetic acid and cooled to 20° C. A slurry of 12 g N-chlorosuccinimide in 75 ml acetic acid is added portionwise with cooling to maintain a reaction temperature of 20°-25° C. The reaction mixture is stirred for three hours at room temperature and the solvent is removed under reduced pressure to give an oil which is dissolved in methylene chloride and washed with water. The organic phase is dried, and the solvent removed under reduced pressure to give an oil which is dissolved in 250 ml ether and cooled to 10° C. Excess ammonia (anhy.) is bubbled through the reaction mixture with external cooling. The reaction mixture is washed with water, dried, and concentrated under reduced pressure to give a solid.

EXAMPLE 3

Methyl (4,6-dimethoxypyrimidin-2-yl)carbamate

2-Amino-4,6-dimethoxypyrimidine (56 g) was added portionwise to 50% sodium hydride (42.8 g) in 1000 ml of dry tetrahydrofuran. After stirring for 0.5 hour, dimethylcarbonate (58.5 g) was added dropwise with cooling. The mixture was stirred under nitrogen for about 16 hours at ambient temperature. Concentrated HCl (80 ml) was added slowly as external cooling was used to maintain a pot temperature of about 25° C. Saturated aqueous sodium chloride (80 ml) was then added. The solvents were decanted from the precipitated solids and dried over sodium sulfate. Filtration and evaporation of the solvents afforded the crude material which was recrystallized from hexane to yield 54 g of the title compound, m.p. 81°-83° C. The IR spectrum showed characteristic absorption bands at 3400 and 1760 cm$^{-1}$.

EXAMPLE 4

N-[(4-Methoxy-6-methylpyrimidin-2-yl)aminocarbonyl]-2,2-dimethyl-1,3-benzodioxole-4-sulfonamide To a solution of 0.55 g 2,2-dimethyl-1,3-benzodioxole-4-sulfonamide, prepared in Example 1, in 30 ml methylene chloride at ambient temperature under nitrogen was added 1.2 ml of trimethylaluminum (2M in toluene). After stirring 15 minutes at ambient temperature, 0.47 g of methyl [4-methoxy-6-methylpyrimidin-2-yl]carbamate, prepared according to the procedure of Example 3, was added and the reaction mixture was heated at reflux 16 hours. The reaction mixture was cooled to ambient temperature and 75 ml H$_2$O, 10 ml glacial acetic acid, and 10 drops hydrochloric acid were sequentially added. The organic phase was separated, dried, and the solvent removed under reduced pressure to give an oil. Crystallization of the oil from a mixture of butyl chloride, hexane and ether gave 0.25 g white solid, m.p. 180°-183° C. The infrared spectrum showed a carbonyl absorption at 1705 cm$^{-1}$ indicative of the title compound.

$^1$HNMR (CDCl$_3$): δ 1.6 (s, 6H); 2.5 (s, 3H); 4.0 (s, 3H); 6.3 (s, 1H); and 6.9–7.6 (m, 3H).

EXAMPLE 5

Methyl(4,6-dimethoxy-1,3,5-triazin-2-yl)carbamate

2-Amino-4,6-dimethoxy-1,3,5-triazine (55.3 g) was added portionwise to 50% sodium hydride (38.0 g) in 1000 ml dry tetrahydrofuran at ambient temperature under nitrogen. After the reaction mixture was stirred for 1.25 hours, dimethylcarbonate (50.0 g) was added dropwise. The reaction mixture was stirred 16 hours at ambient temperature under nitrogen and concentrated hydrochloric acid (68 ml) was slowly added followed by 100 ml tetrahydrofuran. Insoluble material was removed via filtration and discarded. The filtrate was dried and the solvent removed under reduced pressure to give a solid which upon crystallization from ethanol afforded 43.9 g of the title compound, m.p. 118°–122° C.

EXAMPLE 6

N-[(4-Methoxy-6-methyl-1,3,5-triazin-2-yl)aminocarbonyl]-2,2-dimethyl-1,3-benzodioxole-4-sulfonamide To a solution of 1.0 g 2,2-dimethyl-1,3-benzodioxole-4-sulfonamide, prepared in Example 1, in 50 ml methylene chloride at room temperature under nitrogen was added 2.5 ml trimethylaluminum (2M in toluene). After stirring 15 minutes at room temperature, 0.7 g of methyl[4-methoxy-6-methyl-1,3,5-triazin-2-yl]carbamate, prepared according to the procedure of Example 5, was added and the reaction mixture was heated at reflux 72 hours. The reaction mixture was cooled to room temperature and 75 ml ice, 3 ml glacial acetic acid, and 10 drops of hydrochloric acid were sequentially added. The organic phase was separated, dried and the solvent removed under reduced pressure to give an oil. Crystallization of the oil from a mixture of ether, methylene chloride, and hexane gave 0.1 g white solid, m.p. 160°–168° C. The infrared spectrum showed a carbonyl absorption at 1705 cm$^{-1}$ indicative of the title compound.

$^1$HNMR ((CD$_3$)$_2$CO): δ 1.6 (s, 6H); 2.5 (s, 3H); 4.0 (s, 3H); and 6.9–7.6 (m, 3H).

EXAMPLE 7

2,2-Dimethyl-1,3-Benzodithiole-4-Sulfonamide

To a solution of 69 ml s-butyllithium and 15 ml N,N,N',N'-tetramethylethylenediamine in 200 ml THF stirring at −78° C. under nitrogen was added a THF solution of 18.2 g 2,2-dimethyl-1,3-benzodithiole [prepared according to the procedure of Pelter et al., *Tetrahedron Lett.*, 1977, 225]. The temperature was maintained at −78° C. to −65° C. with external dry ice bath cooling during the addition. The reaction mixture was stirred 1 hour at −78° C. Excess sulfur dioxide was bubbled through the reaction mixture, kept at −70° C. to −60° C. with cooling until no further exotherm was noted. The reaction mixture was warmed to ambient temperature, stirred for 18 hours and 10 ml isopropyl alcohol was added. The reaction mixture was concentrated and crystallized from ether/methylene chloride to give a solid. The solid is added to 150 ml of acetic acid and cooled to 20° C. A slurry of 12 g N-chlorosuccinimide in 75 ml acetic acid is added portionwise with cooling to maintain a reaction temperature of 20°–25° C. The reaction mixture is stirred for 2 hours at room temperature and the solvent is removed under reduced pressure to give an oil which is dissolved in methylene chloride and washed with water. The organic phase is dried and the solvent removed under reduced pressure to give an oil which is dissolved in 250 ml ether and cooled to 10° C. Excess ammonia (anhy.) is bubbled through the reaction mixture with external cooling. The reaction mixture is warmed to room temperature, washed with water, dried, and concentrated under reduced pressure to give a tan solid.

EXAMPLE 8

1,3-Benzodithiole-4-sulfonamide

To a solution of 1.7 g dibromomethane and Aliquat 336® in 75 ml toluene was added dropwise a solution of 2.2 g 3-bromothiocatechol (prepared according to the procedures of L. Horner et al., *Phosphorus and Sulfur*, 1982, 2, 353 and A. Ferretti, *Org. Synth.*, 1973, Coll. Vol. V, 419), 2.4 g of 50% sodium hydroxide, and 25 ml water. The reaction mixture was heated at reflux 1.5 hour, cooled to ambient temperature and stirred 16 hours. The organic phase was separated, washed with 1N sodium hydroxide and water, dried and concentrated under reduced pressure to give an oil. The oil was purified via distillation to give 1.4 g 4-bromo-1,3-benzodithiole. The oil was dissolved in 60 ml of tetrahydrofuran under a nitrogen atmosphere, cooled to −70° C. and treated sequentially with 4.5 ml n-butyllithium (1.6N in hexanes) for 0.5 hour at −70° C. and excess sulfur dioxide until no further exotherm was noted. The reaction mixture was contacted with 3 ml isopropyl alcohol, concentrated in vacuo and crystallized from ether/tetrahydrofuran to give a solid. The solid was added to 40 ml acetic acid and cooled to 20° C. A slurry of 0.8 g N-chlorosuccinimide in 20 ml acetic acid was added portionwise with cooling to maintain a reaction temperature of 20°–25° C. The reaction mixture was stirred for three hours at room temperature and the solvent was removed under reduced pressure to give an oil which was dissolved in methylene chloride and washed with water. The organic phase was dried, and the solvent removed under reduced pressure to give an oil which was dissolved in 250 ml ether and cooled to 10° C. Excess ammonia (anhy.) was bubbled through the reaction mixture with external cooling. The reaction mixture was washed with water, dried, and concentrated under reduced pressure to give a solid.

EXAMPLE 2

2,2-Dimethyl-1,3-benzodithiole-4-sulfonamide, 1,1,3,3-tetraoxide

To a solution of 10.0 g 2,2-dimethyl-1,3-benzodithiole, prepared in Example 7, in 150 ml glacial acetic acid was added dropwise with external cooling 34.5 ml 30% hydrogen peroxide. The reaction mixture was stirred at room temperature one hour, heated at reflux 1 hour, cooled to ambient temperature and stirred 16 hours. Aqueous sodium bisulfite and ether were added to the reaction mixture and the resultant mixture washed with sodium bisulfite, solid sodium chloride, dried and concentrated under reduced pressure to give 7.0 g white solid, m.p. 146°–148° C. The solid was dissolved in 40 ml THF at −70° C. under nitrogen and 22 ml of butyllithium (1.6N in hexanes) was added dropwise with external cooling to maintain a maximum temperature of −65° C. The reaction mixture was stirred 1 hour at −70° C. Excess sulfur dioxide was bubbled through the reaction mixture, kept at −70° C. with cooling until no further exotherm was noted. The reaction mixture was warmed to ambient temperature, stirred at −70° C. for 18 hours and 10 ml isopropyl alcohol was added. The reaction mixture was concentrated and crystallized from ether/methylene chloride to give a solid. The solid was added to 150 ml of acetic acid and cooled to 20° C. A slurry of 3.7 g N-chlorosuccinimide in 75 ml acetic acid was added portionwise with cooling to maintain a reaction temperature of 20°–25° C. The reaction mixture was stirred for 2 hours at room temperature and the solvent was removed under reduced pressure to give an oil which is dissolved in methylene chloride and washed with water. The organic phase was dried and the solvent removed under reduced pressure to give an oil which is dissolved in 250 ml ether and cooled to 10° C. Excess ammonia (anhy.) was bubbled through the reaction mixture with external cooling. The reaction mixture was warmed to room temperature, washed with water, dried, and concentrated under reduced pressure to give a solid, m.p. 215°–220° C.

EXAMPLE 10

N-[(4-Methoxy-6-methylpyrimidin-2-yl)aminocarbonyl)]2,2-dimethyl-1,3-benzodithiole-4-sulfonamide To a solution of 2.61 g 2,2-dimethyl-1,3-benzodithiole-4-sulfonamide, prepared in Example 7, in 45 ml methylene chloride at ambient temperature under nitrogen was added 5 ml of trimethylaluminum (2M in toluene). After stirring 15 minutes at ambient temperature, 2.0 g of methyl(4-methoxy-6-methylpyrimidin-2-yl)carbamate, prepared according to the procedure of Example 3, was added and the reaction mixture was heated at reflux 16 hours. The reaction mixture was cooled to ambient temperature and 75 ml H$_2$O, 10 ml glacial acetic acid, and 10 drops hydrochloric acid were sequentially added. The organic phase was separated, dried, and the solvent removed under reduced pressure to give an oil. Crystallization of the oil from an ether solvent gave a solid.

EXAMPLE 11

N-[(4-Methoxy-6-methyl-1,3,5-triazin-2-yl)aminocarbonyl]-2,2-dimethyl-1,3-benzodithiole-4-sulfonamide To a solution of 2.6 g 2,2-dimethyl-1,3-benzodithiole-4-sulfonamide prepared in Example 7, in 60 ml methylene chloride at room temperature under nitrogen is added 5.5 ml trimethylaluminum (2M in toluene). After stirring 15 minutes at room temperature, 2.0 g of methyl [4-methoxy-6-methyl-1,3,5-triazin-2-yl]carbamate, prepared according to the procedure of Example 5, was added and the reaction mixture was heated at reflux for 72 hours. The reaction mixture was cooled to room temperature and 75 ml ice, 3 ml glacial acetic acid, and 10 drops of hydrochloric acid were sequentially added. The organic phase was separated, dried and the solvent removed under reduced pressure to give an oil. Crystallization of the oil from an appropriate solvent gave a solid.

EXAMPLE 12

N-[(4-Methoxy-6-methylpyrimidin-2-yl)aminocarbonyl]-2,2-dimethyl-1,3-benzodithiole-4-sulfonamide 1,1,3,3-tetraoxide To a solution of 3.25 g 2,2-dimethyl-1,3-benzodithiole-4-sulfonamide, 1,1,3,3-tetraoxide, prepared in Example 1, in 50 ml methylene chloride at ambient temperature under nitrogen was added 5.5 ml trimethylaluminum (2M in toluene). After stirring 15 minutes at ambient temperature, 2.0 g of methyl 4-methoxy-6-methylpyrimidin-2-yl)carbamate, prepared according to the procedure of Example 3, was added and the reaction mixture was heated at reflux for 72 hours. The reaction mixture was cooled to ambient temperature and 75 ml water, 10 ml glacial acetic acid, and 10 drops hydrochloric acid were sequentially added. The organic phase was separated, dried, and the solvent removed under reduced pressure to give an oil. Crystallization of the oil from n-butyl chloride/ether gave a solid, m.p. 191°–200° C.

IR(mull): 1690 (c=o) cm$^{-1}$.

NMR ((CD$_3$)$_2$CO): δ 1.6 (s, 3H); 2.1 (s, 6H); 4.0 (s, 3H); 6.5 (s, 1H); and 8.1–9.0 (m, 3H).

EXAMPLE 13

1,3-Benzoxathiole-4-sulfonamide

To a solution of 17 g dibromomethane and Aliquat 336 ® in 200 ml toluene is added dropwise a solution of 21 g 3-bromo-2-mercapto phenol [prepared according to the procedure of S. Cabiddu et al., *Synthesis*, loc. cit. and A. Bashall and J. Collins, *Tetrahed. Lett.*, loc. cit.] 24 g of 50% sodium hydroxide and 50 ml H$_2$O. The reaction mixture is then heated at reflux for 16 hours and cooled to ambient temperature. The organic phase is separated, washed with 1N sodium hydroxide and water, dried and concentrated under reduced pressure to give an oil. The oil is purified via distillation to give 14 g 4-bromo-1,3-benzoxathiole. The oil is dissolved in 60 ml of tetrahydrofuran under a nitrogen atmosphere, cooled to −70° C. and treated sequentially with 45 ml n-butyllithium (1.6N in hexanes) for 1 hour and excess sulfur dioxide until no further exotherm is noted. The reaction mixture is contacted with 2 ml isopropyl alcohol, concentrated in vacuo and crystallized from ether/tetrahydrofuran to give a solid. The solid is added to 150 ml acetic acid and cooled to 20° C. A slurry of 8.0 g N-chlorosuccinimide in 30 ml acetic acid is added portionwise with cooling to maintain a reaction temperature of 20°–25° C. The reaction mixture is stirred for three hours at room temperature and the solvent is removed under reduced pressure to give an oil which is dissolved in methylene chloride and washed with water. The organic phase is dried, and the solvent removed under reduced pressure to give an oil which is dissolved in 250 ml ether and cooled to 10° C. Excess ammonia (anhy.) is bubbled through the reaction mixture with external cooling. The reaction mixture is washed with water, dried, and concentrated under reduced pressure to give a solid.

EXAMPLE 14

N-[(4-Methoxy-6-methylpyrimidin-2-yl)aminocarbonyl]-1,3-benzoxathiole-4-sulfonamide To a solution of 2.2 g 1,3-benzoxathiole-4-sulfonamide, prepared in Example 13, in 50 ml methylene chloride at ambient temperature under nitrogen is added 5.5 ml trimethylaluminum (2M in toluene). After stirring 15 minutes at ambient temperature, 2.0 g of methyl [4-methoxy-6-methylpyrimidin-2-yl]carbamate, prepared according to the procedure of Example 3, is added and the reaction mixture is heated at reflux for 16 hours. The reaction mixture is cooled to ambient temperature and 75 ml water, 10 ml glacial acetic acid, and 10 drops hydrochloric acid are sequentially added. The organic phase is separated, dried, and the solvent removed under reduced pressure to give an oil. Crystallization of the oil from n-butyl chloride/ether gives a solid.

The compounds of Table I can be prepared according to the procedures of Examples 4, 6, 10, 11, 12 and 14 using the appropriate 4-sulfonamide and carbamate.

EXAMPLE 15

1,4-Benzodioxan-5-sulfonamide

To a solution of 43.6 g 5-bromo-1,4-benzodioxan (prepared according to the procedures of S. Cabiddu et al., *Synthesis*, loc. cit.) and in 400 ml tetrahydrofuran −70° under nitrogen was added dropwise 127 ml of n-butyllithium (1.6N in hexane). The temperature was maintained at −70° C. with dry ice/acetone cooling during the addition. The reaction mixture was stirred 0.5 hour at −70° C. Excess sulfur dioxide was bubbled through the reaction mixture, kept at −60° to −70° C. with cooling until no further exotherm was noted. The reaction mixture was stirred at −70° C. for 2.5 hours, warmed to room temperature, stirred overnight, and 10 ml isopropyl alcohol is added. The reaction mixture was concentrated in vacuo and crystallized from ether/tetrahydrofuran to give a solid. The solid was added to 150 ml acetic acid and the resultant mixture was cooled to 20° C. A slurry of 20.5 g of N-chlorosuccinimide in 125 ml acetic acid was added portionwise with cooling to maintain the reaction mixture between 20°–25° C. The reaction mixture was stirred 3 hours at ambient temperature and the solvent was removed under reduced pressure to give an oil. The oil was dissolved in methylene chloride and washed with water. The organic phase was dried and the solvent removed under reduced pressure to give an oil which was dissolved in 300 ml ether and cooled to 10° C. Excess ammonia (anhy.) was bubbled through the reaction mixture using ice bath cooling. The reaction mixture was warmed to ambient temperature, stirred for 1 hour, and 100 ml ether added. The reaction mixture was washed with water, dried, and concentrated in vacuo to give a solid, m.p. 114°–117° C., IR(mull).

$^1$HNMR (DMSO-d$_6$): 4.3 (s, 4H); and 6.7–7.6 (m, 5H).

EXAMPLE 16

N-[(4-Methoxy-6-methylpyrimidin-2-yl)aminocarbonyl]-1,4-benzodioxan-5-sulfonamide To a solution of 1.0 g 1,4-benzodioxan-5-sulfonamide, prepared in Example 15, in 50 ml methylene chloride at ambient temperature under nitrogen was added 2.5 ml trimethylaluminum (2M in toluene). After stirring 15 minutes at ambient temperature, 1.0 g of methyl [4-methoxy-6-methylpyrimidin-2-yl]carbamate, prepared according to the procedure of Example 3, was added and the reaction mixture was heated at reflux for 72 hours. The reaction mixture was cooled to ambient temperature and 75 ml water, 10 ml glacial acetic acid and 10 drops hydrochloric acid were sequentially added. The organic phase was separated, dried, and the solvent removed under reduced pressure to give an oil. Crystallization of the oil from n-butyl chloride/ether gave a solid, m.p. 203°–205° C.

IR(mull) 1700 (c=o) cm$^{-1}$.

$^1$HNMR ((CD$_3$)$_2$CO): 2.5 (s, 3H), 4.0 (s, 3H); 4.4 (s, 3H); 6.4 (s, 1H); 7.1 (m, 3H); and 7.7 (m, 2H).

EXAMPLE 17

N-[(4,6-Dimethoxy-1,3,5-triazin-2-yl)aminocarbonyl]-1,4-benzodioxan-5-sulfonamide To a solution of 1.0 g 1,4-benzodioxan-5-sulfonamide, prepared in Example 15, in 50 ml methylene chloride at ambient temperature under nitrogen, is added 2.5 ml trimethylaluminum (2M in toluene). After stirring 15 minutes at ambient temperature, 1.1 g of methyl [4,6-dimethoxytriazin-2-yl]carbamate, prepared in Example 5, is added and the reaction mixture is heated at reflux 16 hours. The reaction mixture is cooled to ambient temperature and 75 ml water, 10 ml glacial acetic acid, and 10 drops hydrochloric acid are sequentially added. The organic phase is separated, dried and the solvent removed under reduced pressure to give an oil. Crystallization of the oil from an appropriate organic solvent gives a solid.

EXAMPLE 18

1,4-Benzodithian-5-sulfonamide

To a solution of 17 g dibromo ethane and Aliquat 336 ® in 200 ml toluene is added dropwise a solution of 22 g 3-bromothiocatechol [prepared according to the procedures of L. Horner et al., loc. cit. and A. Ferretti, loc. cit., 24 g of 50% sodium hydroxide, and 50 ml H$_2$O. The reaction mixture was then treated at reflux for 1.5 hour, cooled to ambient temperature and stirred 16 hours. The organic phase was separated, washed in 1N sodium hydroxide and water, dried and concentrated under reduced pressure to give an oil. The oil was purified via distillation to give 15 g 4-bromo-1,3-benzodithiole. The oil was dissolved in 60 ml of tetrahydrofuran under a nitrogen atmosphere, cooled to −70° C. and treated sequentially with 50 ml n-butyllithium (1.6N in hexanes) for 1 hour and excess sulfur dioxide until no further exotherm was noted. The reaction mixture was contacted with 3 ml isopropyl alcohol, concentrated in vacuo and crystallized from ether/tetrahydrofuran to give a solid. The solid was added to 150 ml acetic acid and cooled to 20° C. A slurry of 8.0 g N-chlorosuccinimide in 30 ml acetic acid was added portionwise with cooling to maintain a reaction temperature of 20°–25° C. The reaction mixture was stirred for three hours at room temperature and the solvent was removed under reduced pressure to give an oil which was dissolved in methylene chloride and washed with water. The organic phase was dried, and the solvent removed under reduced pressure to give an oil which was dissolved in 250 ml ether and cooled to 10° C. Excess ammonia (anhy.) was bubbled through the reaction mixture with external cooling. The reaction mixture was washed with water, dried, and concentrated under reduced pressure to give a solid.

EXAMPLE 19

N-[(4-methoxy-6-methylpyrimidin-2-yl)aminocarbonyl]-1,4-benzodithian-5-sulfonamide To a solution of 2.5 g 1,4-benzodithian-5-sulfonamide, prepared in Example 18, in 50 ml methylene chloride at ambient temperature under nitrogen is added 5.5 ml trimethylaluminum (2M in toluene). After stirring 15 minutes at ambient temperature 2.0 g of methyl [4-methoxy-6-methylpyrimidin-2-yl]carbamate, prepared according to the procedure of Example 3, is added and the reaction mixture is heated at reflux for 16 hours. The reaction mixture is cooled to ambient temperature and 75 ml water, 10 ml glacial acetic acid, and 10 drops hydrochloric acid are sequentially added. The organic phase is separated, dried, and the solvent removed under reduced pressure to give an oil. Crystallization of the oil from n-butyl chloride/ether gives a solid.

EXAMPLE 20

N-[(4,6-Dimethoxy-1,3,5-triazin-2-yl)aminocarbonyl]-1,4-benzodithian-5-sulfonamide To a solution of 2.5 g 1,4-benzodithian-5-sulfonamide, prepared in Example 16, in 50 ml methylene chloride at ambient temperature under nitrogen is added 5.5 ml trimethylaluminum (2M in toluene). After stirring 15 minutes at ambient temperature 2.0 g of methyl [4,6-Dimethoxy-1,3,5-triazin-2-yl]carbamate, prepared according to the procedure of Example 3 is added and the reaction mixture is heated at reflux for 16 hours. The reaction mixture is cooled to ambient temperature and 75 ml water, 10 ml glacial acetic acid, and 10 drops hydrochloric acid are sequentially added. The organic phase is separated, dried and the solvent removed under reduced pressure to give an oil. Crystallization of the oil from an appropriate organic solvent gives a solid.

The compounds of Table II can be prepared according to the procedures of Examples 16, 17, 19 and 20 using the appropriate 5-sulfonamide and heterocyclic carbamate.

TABLE Ia

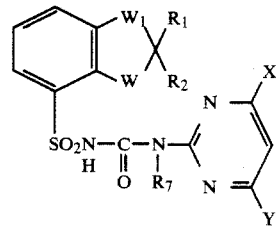

| $W_1$ | W | $R_1$ | $R_2$ | $R_7$ | X | Y | m.p.(°C.) |
|---|---|---|---|---|---|---|---|
| O | O | H | H | H | $CH_3$ | $CH_3$ | |
| O | O | H | H | H | $CH_3$ | $OCH_3$ | |
| O | O | H | H | H | $CH_3$ | $OC_2H_5$ | |
| O | O | H | H | H | $OCH_3$ | $OCH_3$ | |
| O | O | H | H | H | $OCH_3$ | $OC_2H_5$ | |
| O | O | H | H | H | $OCH_3$ | $SCH_3$ | |
| O | O | H | H | H | $OCH_3$ | $CH(OCH_3)_2$ | |
| O | O | H | H | H | Cl | $NH_2$ | |
| O | O | H | H | H | Cl | $NHCH_3$ | |
| O | O | H | H | H | Cl | $N(CH_3)$ | |
| O | O | H | H | H | Cl | $OCH_3$ | |
| O | O | H | H | $CH_3$ | $CH_3$ | $CH_3$ | |
| O | O | H | H | $CH_3$ | $CH_3$ | $OCH_3$ | |
| O | O | H | $CH_3$ | H | $CH_3$ | $CH_3$ | |
| O | O | H | $CH_3$ | H | $CH_3$ | $OCH_3$ | |
| O | O | H | $CH_3$ | H | $CH_3$ | $SCH_3$ | |
| O | O | H | $CH_3$ | H | $CH_3$ | $CH(OCH_3)_2$ | |
| O | O | H | $CH_3$ | H | $OCH_3$ | $CH_3$ | |
| O | O | H | $CH_3$ | H | $OCH_3$ | $OCH_3$ | |
| O | O | H | $CH_3$ | H | $OCH_3$ | $-CH\begin{smallmatrix}O\\ \\O\end{smallmatrix}\Big]$ | |
| O | O | H | $CH_3$ | H | Cl | $N(CH_3)_2$ | |
| O | O | H | $C_2H_5$ | H | $CH_3$ | $NH_2$ | |
| O | O | H | $C_2H_5$ | H | $CH_3$ | $OC_2H_5$ | |
| O | O | H | $C_2H_5$ | H | $CH_3$ | $SCH_3$ | |
| O | O | H | $C_2H_5$ | H | $OCH_3$ | $CH_2OCH_3$ | |
| O | O | H | $C_2H_5$ | H | $OCH_3$ | $OCH_3$ | |
| O | O | H | $CH_3CH_2CH_2$ | H | $CH_3$ | $N(CH_3)_2$ | |
| O | O | H | $CH_3CH_2CH_2$ | H | $CH_3$ | $OCH_3$ | |
| O | O | H | $CH_3CH_2CH_2$ | H | $OCH_3$ | $NH_2$ | |
| O | O | H | $CH(CH_3)_2$ | H | $OCH_3$ | $OCH_3$ | |
| O | O | H | $CH_3CH_2CH_2CH_2$ | H | $CH_3$ | $OCH_3$ | |
| O | O | H | $CH_3CH(CH_3)CH_2$ | H | $CH_3$ | $NH(CH_3)$ | |
| O | O | H | $CH_3CH_2CH(CH_3)$ | H | $OCH_3$ | $OC_2H_5$ | |
| O | O | H | $(CH_3)_3C$ | H | $CH_3$ | $OCH_3$ | |
| O | O | H | $(CH_3)_3C$ | H | $OCH_3$ | $OCH_3$ | |
| O | O | $CH_3$ | $CH_3$ | H | $CH_3$ | H | |
| O | O | $CH_3$ | $CH_3$ | H | $CH_3$ | $CH_3$ | 168–171° |
| O | O | $CH_3$ | $CH_3$ | H | $CH_3$ | $OCH_3$ | 180–183° |
| O | O | $CH_3$ | $CH_3$ | H | $CH_3$ | $OC_2H_5$ | |
| O | O | $CH_3$ | $CH_3$ | H | $CH_3$ | $CH_2OCH_3$ | |
| O | O | $CH_3$ | $CH_3$ | H | $CH_3$ | $SCH_3$ | |
| O | O | $CH_3$ | $CH_3$ | H | $OCH_3$ | $OCH_3$ | 194–203° |
| O | O | $CH_3$ | $CH_3$ | H | Cl | $OCH_3$ | |
| O | O | $CH_3$ | $CH_3$ | H | Cl | $NH_2$ | |
| O | O | $CH_3$ | $CH_3$ | H | Cl | $NH(CH_3)$ | |

TABLE Ia-continued

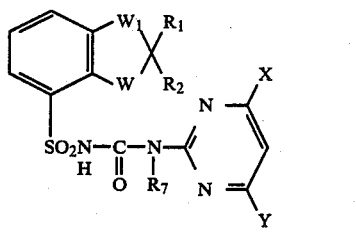

| $W_1$ | W | $R_1$ | $R_2$ | $R_7$ | X | Y | m.p.(°C.) |
|---|---|---|---|---|---|---|---|
| O | O | CH₃ | CH₃ | H | Cl | N(CH₃)₂ | |
| O | O | CH₃ | CH₃ | CH₃ | CH₃ | CH₃ | |
| O | O | CH₃ | CH₃ | CH₃ | CH₃ | OCH₃ | |
| O | O | CH₃ | CH₃ | CH₃ | OCH₃ | OCH₃ | |
| O | O | CH₃ | CH₃CH₂ | H | CH₃ | CH₃ | |
| O | O | CH₃ | CH₃CH₂ | H | CH₃ | -CH(O-CH₂-CH₂-O) | |
| O | O | CH₃ | CH₃CH₂ | H | OCH₃ | OCH₃ | |
| O | O | CH₃ | CH₃CH₂CH₂ | H | CH₃ | OCH₃ | |
| O | O | CH₃ | CH₃CH₂CH₂ | H | OCH₃ | OCH₃ | |
| O | O | CH₃ | CH₃CH₂CH₂ | H | OCH₃ | OC₂H₅ | |
| O | O | CH₃ | (CH₃)₂CH | H | OCH₃ | OCH₃ | |
| O | O | CH₃ | CH₃CH₂CH₂CH₂— | H | CH₃ | CH₃ | |
| O | O | CH₃ | CH₃CH₂CH₂CH₂— | H | CH₃ | N(CH₃)₂ | |
| O | O | CH₃ | CH₃CH₂CH₂CH₂— | H | Cl | N(CH₃)₂ | |
| O | O | CH₃ | CH₃CH(CH₃)CH₂ | H | CH₃ | OCH₃ | |
| O | O | CH₃ | CH₃CH(CH₃)CH₂ | H | CH₃ | NHCH₃ | |
| O | O | CH₃ | CH₃CH₂CH(CH₃) | H | CH₃ | OCH₃ | |
| O | O | CH₃ | (CH₃)₃C | H | CH₃ | CH(OCH₃)₂ | |
| S | S | H | H | H | CH₃ | CH₃ | |
| S | S | H | H | H | CH₃ | OCH₃ | |
| S | S | H | H | H | CH₃ | OC₂H₅ | |
| S | S | H | H | H | OCH₃ | OCH₃ | |
| S | S | H | H | H | OCH₃ | OC₂H₅ | |
| S | S | H | H | H | OCH₃ | SCH₃ | |
| S | S | H | H | H | OCH₃ | CH(OCH₃)₂ | |
| S | S | H | H | H | Cl | NH₂ | |
| S | S | H | H | H | Cl | NHCH₃ | |
| S | S | H | H | H | Cl | N(CH₃)₂ | |
| S | S | H | H | H | Cl | OCH₃ | |
| S | S | H | H | CH₃ | CH₃ | CH₃ | |
| S | S | H | H | CH₃ | CH₃ | OCH₃ | |
| S | S | H | CH₃ | H | CH₃ | CH₃ | |
| S | S | H | CH₃ | H | CH₃ | OCH₃ | |
| S | S | H | CH₃ | H | CH₃ | N(CH₃)₂ | |
| S | S | H | CH₃ | H | OCH₃ | OCH₃ | |
| S | S | H | CH₃ | H | OCH₃ | -CH(O-CH₂-CH₂-O) | |
| S | S | H | CH₃ | H | Cl | N(CH₃)₂ | |
| S | S | H | C₂H₅ | H | CH₃ | CH₃ | |
| S | S | H | C₂H₅ | H | CH₃ | OCH₃ | |
| S | S | H | C₂H₅ | H | CH₃ | SCH₃ | |
| S | S | H | C₂H₅ | H | OCH₃ | OCH₃ | |
| S | S | H | CH₃CH₂CH₂ | H | CH₃ | CH₃ | |
| S | S | H | CH₃CH₂CH₂ | H | CH₃ | OCH₃ | |
| S | S | H | CH(CH₃)₂ | H | OCH₃ | OCH₃ | |
| S | S | H | CH₃CH₂CH₂CH₂ | H | CH₃ | OCH₃ | |
| S | S | H | CH₃CH(CH₃)CH₂ | H | CH₃ | CH₃ | |
| S | S | H | CH₃CH₂CH(CH₃) | H | OCH₃ | OCH₃ | |
| S | S | H | (CH₃)₃C | H | CH₃ | OCH₃ | |
| S | S | H | (CH₃)₃C | H | OCH₃ | OCH₃ | |
| S | S | CH₃ | CH₃ | H | CH₃ | H | |
| S | S | CH₃ | CH₃ | H | CH₃ | CH₃ | |
| S | S | CH₃ | CH₃ | H | CH₃ | OCH₃ | |
| S | S | CH₃ | CH₃ | H | CH₃ | OC₂H₅ | |
| S | S | CH₃ | CH₃ | H | CH₃ | CH₂OCH₃ | |
| S | S | CH₃ | CH₃ | H | CH₃ | SCH₃ | |
| S | S | CH₃ | CH₃ | H | OCH₃ | OCH₃ | |

TABLE Ia-continued

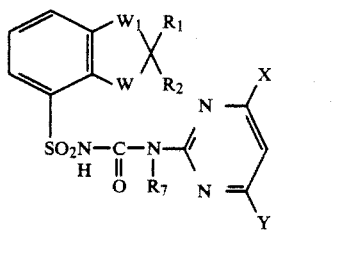

| W₁ | W | R₁ | R₂ | R₇ | X | Y | m.p.(°C.) |
|---|---|---|---|---|---|---|---|
| S | S | CH₃ | CH₃ | H | OCH₃ | ![cyclic OCH(OCH₂CH₂O)] | |
| S | S | CH₃ | CH₃ | H | Cl | OCH₃ | |
| S | S | CH₃ | CH₃ | H | Cl | NH₂ | |
| S | S | CH₃ | CH₃ | H | Cl | NH(CH₃) | |
| S | S | CH₃ | CH₃ | H | Cl | N(CH₃)₂ | |
| S | S | CH₃ | CH₃ | CH₃ | CH₃ | OCH₃ | |
| S | S | CH₃ | CH₃ | CH₃ | OCH₃ | OCH₃ | |
| S | S | CH₃ | CH₃CH₂ | H | CH₃ | CH₃ | |
| S | S | CH₃ | CH₃CH₂ | H | CH₃ | OCH₃ | |
| S | S | CH₃ | CH₃CH₂ | H | OCH₃ | OCH₃ | |
| S | S | CH₃ | CH₃CH₂ | H | OCH₃ | CH(OCH₃)₂ | |
| S | S | CH₃ | CH₃CH₂CH₂ | H | CH₃ | CH₃ | |
| S | S | CH₃ | CH₃CH₂CH₂ | H | CH₃ | CH(OCH₃)₂ | |
| S | S | CH₃ | CH₃CH₂CH₂ | H | OCH₃ | OCH₃ | |
| S | S | CH₃ | CH₃CH₂CH₂ | H | OCH₃ | OC₂H₅ | |
| S | S | CH₃ | (CH₃)₂CH | H | OCH₃ | OCH₃ | |
| S | S | CH₃ | CH₃CH₂CH₂CH₂— | H | CH₃ | SCH₃ | |
| S | S | CH₃ | CH₃CH₂CH₂CH₂— | H | OCH₃ | OCH₃ | |
| S | S | CH₃ | CH₃CH(CH₃)CH₂ | H | CH₃ | OCH₃ | |
| S | S | CH₃ | CH₃CH(CH₃)CH₂ | H | Cl | N(CH₃)₂ | |
| S | S | CH₃ | CH₃CH₂CH(CH₃) | H | CH₃ | OCH₃ | |
| S | S | CH₃ | (CH₃)₃C | H | CH₃ | OCH₃ | |
| SO₂ | SO₂ | H | H | H | CH₃ | CH₃ | |
| SO₂ | SO₂ | H | H | H | CH₃ | OCH₃ | |
| SO₂ | SO₂ | H | H | H | CH₃ | OC₂H₅ | |
| SO₂ | SO₂ | H | H | H | OCH₃ | OCH₃ | |
| SO₂ | SO₂ | H | H | H | OCH₃ | OC₂H₅ | |
| SO₂ | SO₂ | H | H | H | OCH₃ | SCH₃ | |
| SO₂ | SO₂ | H | H | H | OCH₃ | CH(OCH₃)₂ | |
| SO₂ | SO₂ | H | H | H | Cl | N(CH₃)₂ | |
| SO₂ | SO₂ | H | H | H | Cl | OCH₃ | |
| SO₂ | SO₂ | H | H | CH₃ | CH₃ | CH₃ | |
| SO₂ | SO₂ | H | H | CH₃ | CH₃ | OCH₃ | |
| SO₂ | SO₂ | H | CH₃ | H | CH₃ | CH₃ | |
| SO₂ | SO₂ | H | CH₃ | H | CH₃ | SCH₃ | |
| SO₂ | SO₂ | H | CH₃ | H | OCH₃ | OCH₃ | |
| SO₂ | SO₂ | CH₃ | CH₃ | H | CH₃ | H | |
| SO₂ | SO₂ | CH₃ | CH₃ | H | CH₃ | CH₃ | |
| SO₂ | SO₂ | CH₃ | CH₃ | H | CH₃ | OCH₃ | 191–200° |
| SO₂ | SO₂ | CH₃ | CH₃ | H | CH₃ | OC₂H₅ | |
| SO₂ | SO₂ | CH₃ | CH₃ | H | OCH₃ | SCH₃ | |
| SO₂ | SO₂ | CH₃ | CH₃ | H | OCH₃ | OCH₃ | |
| SO₂ | SO₂ | CH₃ | CH₃ | H | Cl | OCH₃ | |
| SO₂ | SO₂ | CH₃ | CH₃ | H | Cl | NH₂ | |
| SO₂ | SO₂ | CH₃ | CH₃ | H | Cl | NH(CH₃) | |
| SO₂ | SO₂ | CH₃ | CH₃ | H | Cl | N(CH₃)₂ | |
| SO₂ | SO₂ | CH₃ | CH₃ | CH₃ | CH₃ | OCH₃ | |
| SO₂ | SO₂ | CH₃ | CH₃ | CH₃ | OCH₃ | OCH₃ | |
| SO₂ | SO₂ | CH₃ | CH₃CH₂ | H | CH₃ | CH₃ | |
| SO₂ | SO₂ | CH₃ | CH₃CH₂ | H | CH₃ | OCH₃ | |
| SO₂ | SO₂ | CH₃ | CH₃CH₂ | H | OCH₃ | OCH₃ | |
| SO₂ | SO₂ | CH₃ | CH₃CH₂ | H | OCH₃ | CH(OCH₃)₂ | |
| SO₂ | SO₂ | CH₃ | CH₃CH₂CH₂ | H | CH₃ | CH₃ | |
| SO₂ | SO₂ | CH₃ | CH₃CH₂CH₂ | H | CH₃ | OCH₃ | |
| SO₂ | SO₂ | CH₃ | CH₃CH₂CH₂ | H | OCH₃ | H | |
| SO₂ | SO₂ | CH₃ | CH₃CH₂CH₂ | H | OCH₃ | OCH₃ | |
| SO₂ | SO₂ | CH₃ | CH₃CH₂CH₂ | H | OCH₃ | OC₂H₅ | |
| SO₂ | SO₂ | CH₃ | (CH₃)₂CH | H | OCH₃ | OCH₃ | |
| SO₂ | SO₂ | CH₃ | CH₃CH₂CH₂CH₂— | H | CH₃ | CH₃ | |
| SO₂ | SO₂ | CH₃ | CH₃CH₂CH₂CH₂— | H | CH₃ | SCH₃ | |
| SO₂ | SO₂ | CH₃ | CH₃CH₂CH₂CH₂— | H | OCH₃ | H | |
| SO₂ | SO₂ | CH₃ | CH₃CH₂CH₂CH₂— | H | OCH₃ | OCH₃ | |

TABLE Ia-continued

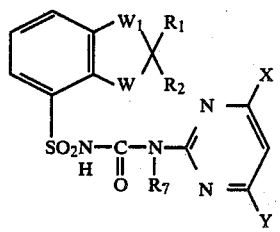

| W₁ | W | R₁ | R₂ | R₇ | X | Y | m.p.(°C.) |
|---|---|---|---|---|---|---|---|
| SO₂ | SO₂ | CH₃ | CH₃CH₂CH₂CH₂— | H | Cl | N(CH₃)₂ | |
| SO₂ | SO₂ | CH₃ | CH₃CH(CH₃)CH₂ | H | CH₃ | OCH₃ | |
| SO₂ | SO₂ | CH₃ | CH₃CH(CH₃)CH₂ | H | OCH₃ | OCH₃ | |
| SO₂ | SO₂ | CH₃ | CH₃CH(CH₃)CH₂ | H | Cl | N(CH₃)₂ | |
| SO₂ | SO₂ | CH₃ | CH₃CH₂CH(CH₃) | H | CH₃ | CH₃ | |
| SO₂ | SO₂ | CH₃ | CH₃CH₂CH(CH₃) | H | CH₃ | OCH₃ | |
| SO₂ | SO₂ | CH₃ | (CH₃)₃C | H | CH₃ | OCH₃ | |
| SO₂ | SO₂ | H | CH₃ | H | Cl | N(CH₃)₂ | |
| SO₂ | SO₂ | H | C₂H₅ | H | CH₃ | CH₃ | |
| SO₂ | SO₂ | H | C₂H₅ | H | CH₃ | OCH₃ | |
| SO₂ | SO₂ | H | C₂H₅ | H | CH₃ | SCH₃ | |
| SO₂ | SO₂ | H | C₂H₅ | H | OCH₃ | OCH₃ | |
| SO₂ | SO₂ | H | CH₃CH₂CH₂ | H | CH₃ | CH₃ | |
| SO₂ | SO₂ | H | CH₃CH₂CH₂ | H | CH₃ | OCH₃ | |
| SO₂ | SO₂ | H | CH(CH₃)₂ | H | OCH₃ | OCH₃ | |
| SO₂ | SO₂ | H | CH₃CH₂CH₂CH₂ | H | CH₃ | OCH₃ | |
| SO₂ | SO₂ | H | CH₃CH(CH₃)CH₂ | H | CH₃ | CH₃ | |
| SO₂ | SO₂ | H | CH₃CH₂CH(CH₃) | H | OCH₃ | OCH₃ | |
| SO₂ | SO₂ | H | (CH₃)₃C | H | CH₃ | OCH₃ | |
| SO₂ | SO₂ | H | (CH₃)₃C | H | OCH₃ | OCH₃ | |
| SO₂ | SO₂ | H | CH₃ | H | CH₃ | OCH₃ | |
| SO | SO | H | H | H | CH₃ | CH₃ | |
| SO | SO | H | H | H | CH₃ | OCH₃ | |
| SO | SO | H | H | H | OCH₃ | SCH₃ | |
| SO | SO | H | H | CH₃ | CH₃ | CH₃ | |
| SO | SO | H | H | CH₃ | CH₃ | OCH₃ | |
| SO | SO | H | CH₃ | H | CH₃ | OCH₃ | |
| SO | SO | CH₃ | CH₃ | H | CH₃ | CH₃ | |
| SO | SO | CH₃ | CH₃ | H | CH₃ | OCH₃ | |
| SO | SO | CH₃ | CH₃ | CH₃ | OCH₃ | OCH₃ | |
| SO | SO | CH₃ | CH₃ | CH₃ | CH₃ | OCH₃ | |
| SO | SO | H | CH₃CH₂CH₂CH₂ | H | CH₃ | OCH₃ | |
| SO | SO | H | CH₃CH₂CH₂CH₂ | H | OCH₃ | OCH₃ | |
| O | S | H | H | H | CH₃ | CH₃ | |
| O | S | H | H | H | CH₃ | OCH₃ | |
| O | S | H | CH₃ | H | CH₃ | OCH₃ | |
| O | S | CH₃ | CH₃ | H | CH₃ | OCH₃ | |
| O | S | CH₃ | CH₃CH₂ | H | CH₃ | OCH₃ | |
| O | SO | H | H | H | CH₃ | CH₃ | |
| O | SO | H | H | H | CH₃ | OCH₃ | |
| O | SO | H | CH₃ | H | CH₃ | SCH₃ | |
| O | SO | CH₃ | CH₃ | H | CH₃ | CH₃ | |
| O | SO | CH₃ | CH₃ | H | OCH₃ | OCH₃ | |
| O | SO | CH₃ | CH₃ | H | Cl | N(CH₃)₂ | |
| O | SO₂ | H | H | H | CH₃ | CH₃ | |
| O | SO₂ | H | H | H | CH₃ | OCH₃ | |
| O | SO₂ | H | H | H | Cl | N(CH₃)₂ | |
| O | SO₂ | H | CH₃ | H | CH₃ | CH₃ | |
| O | SO₂ | H | CH₃ | H | CH₃ | OCH₃ | |
| O | SO₂ | H | CH₃ | H | CH₃ | CH(OCH₃)₂ | |
| O | SO₂ | H | CH₃CH₂CH₂CH₂ | H | CH₃ | OCH₃ | |
| O | SO₂ | CH₃ | CH₃ | H | CH₃ | CH₃ | |
| O | SO₂ | CH₃ | CH₃ | H | CH₃ | OCH₃ | |
| O | SO₂ | CH₃ | CH₃ | H | OCH₃ | SCH₃ | |
| O | SO₂ | CH₃ | CH₃CH₂CH₂ | H | CH₃ | OCH₃ | |
| S | O | H | H | H | CH₃ | OCH₃ | |
| S | O | CH₃ | CH₃ | H | CH₃ | OCH₃ | |
| SO | O | H | H | H | CH₃ | OCH₃ | |
| SO | O | CH₃ | CH₃ | H | CH₃ | OCH₃ | |
| SO₂ | O | H | H | H | CH₃ | CH₃ | |
| SO₂ | O | CH₃ | CH₃ | H | CH₃ | OCH₃ | |
| SO | S | H | H | H | CH₃ | OCH₃ | |
| SO | S | CH₃ | CH₃ | H | CH₃ | OCH₃ | |
| SO₂ | S | H | H | H | CH₃ | OCH₃ | |
| SO₂ | S | CH₃ | CH₃ | H | CH₃ | OCH₃ | |
| S | SO | H | H | H | CH₃ | OCH₃ | |
| S | SO | H | CH₃ | H | CH₃ | OCH₃ | |
| S | SO | CH₃ | CH₃ | H | CH₃ | OCH₃ | |
| S | SO₂ | H | H | H | CH₃ | CH₃ | |

TABLE Ia-continued

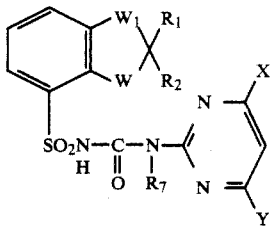

| W₁ | W | R₁ | R₂ | R₇ | X | Y | m.p.(°C.) |
|---|---|---|---|---|---|---|---|
| S | SO₂ | H | H | H | CH₃ | OCH₃ | |
| S | SO₂ | H | CH₃CH₂ | H | CH₃ | OCH₃ | |
| S | SO₂ | CH₃ | CH₃ | H | OCH₃ | OCH₃ | |
| SO | SO₂ | H | H | H | CH₃ | OCH₃ | |
| SO | SO₂ | H | CH₃ | H | CH₃ | OCH₃ | |
| SO | SO₂ | CH₃ | CH₃ | H | CH₃ | CH₃ | |
| SO | SO₂ | CH₃ | CH₃ | H | CH₃ | OCH₃ | |
| SO | SO₂ | CH₃ | CH₃ | H | Cl | N(CH₃)₂ | |
| SO₂ | SO | H | H | H | CH₃ | OCH₃ | |
| SO₂ | SO | H | CH₃ | H | CH₃ | OCH₃ | |
| SO₂ | SO | H | CH₃CH₂ | H | CH₃ | OCH₃ | |
| SO₂ | SO | CH₃ | CH₃ | H | CH₃ | OCH₃ | |
| O | SO₂ | CH₃ | CH₃ | H | OCH₃ | OCH₃ | |
| S | SO₂ | H | H | H | OCH₃ | OCH₃ | |

TABLE Ib

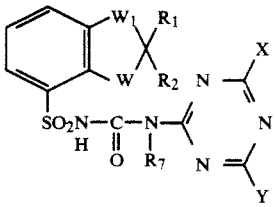

| W₁ | W | R₁ | R₂ | R₇ | X | Y | m.p. (°C.) |
|---|---|---|---|---|---|---|---|
| O | O | H | H | H | CH₃ | CH₃ | |
| O | O | H | H | H | CH₃ | OCH₃ | |
| O | O | H | H | H | CH₃ | SCH₃ | |
| O | O | H | H | H | CH₃ | OC₂H₅ | |
| O | O | H | H | H | CH₃ | CH₂OCH₃ | |
| O | O | H | H | H | OCH₃ | OCH₃ | |
| O | O | H | H | H | OCH₃ | N(CH₃)₂ | |
| O | O | H | H | H | OCH₃ | SCH₃ | |
| O | O | H | H | CH₃ | CH₃ | OCH₃ | |
| O | O | H | H | CH₃ | OCH₃ | OCH₃ | |
| O | O | H | CH₃ | H | CH₃ | CH₃ | |
| O | O | H | CH₃ | H | CH₃ | OCH₃ | |
| O | O | H | CH₃ | H | OCH₃ | OCH₃ | |
| O | O | H | CH₃ | H | OCH₃ | NH(CH₃) | |
| O | O | H | CH₃CH₂ | H | CH₃ | OCH₃ | |
| O | O | H | CH₃CH₂ | H | OCH₃ | OCH₃ | |
| O | O | H | CH₃CH₂ | H | OCH₃ | CH(OCH₂CH₂O) | |
| O | O | H | CH₃CH₂CH₂ | H | CH₃ | CH₃ | |
| O | O | H | CH₃CH₂CH₂ | H | CH₃ | OCH₃ | |
| O | O | H | CH₃CH₂CH₂ | H | OCH₃ | CH₂OCH₃ | |
| O | O | H | (CH₃)₂CH | H | CH₃ | OCH₃ | |
| O | O | H | CH₃CH₂CH₂CH₂ | H | CH₃ | CH₃ | |
| O | O | H | CH₃CH₂CH₂CH₂ | H | OCH₃ | OCH₃ | |
| O | O | H | CH₃CH(CH₃)CH₂ | H | OCH₃ | OCH₃ | |
| O | O | H | CH₃CH₂CH(CH₃) | H | CH₃ | OCH₃ | |
| O | O | H | (CH₃)₃C | H | CH₃ | OCH₃ | |
| O | O | CH₃ | CH₃ | H | CH₃ | CH₃ | 168–171° |
| O | O | CH₃ | CH₃ | H | CH₃ | OCH₃ | 160–168° |
| O | O | CH₃ | CH₃ | H | CH₃ | SCH₃ | |
| O | O | CH₃ | CH₃ | H | CH₃ | CH₂OCH₃ | |
| O | O | CH₃ | CH₃ | H | OCH₃ | OCH₃ | 194–202° |
| O | O | CH₃ | CH₃CH₂ | H | CH₂ | OC₂H₅ | |

TABLE Ib-continued

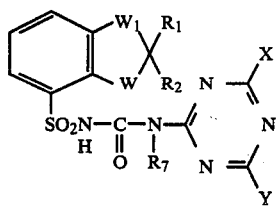

| W₁ | W | R₁ | R₂ | R₇ | X | Y | m.p. (°C.) |
|---|---|---|---|---|---|---|---|
| O | O | CH₃ | CH₃CH₂ | H | OCH₃ | OCH₃ | |
| O | O | CH₃ | CH₃CH₂CH₂ | H | CH₃ | SCH₃ | |
| O | O | CH₃ | CH₃CH₂CH₂ | H | CH₃ | OCH₃ | |
| O | O | CH₃ | (CH₃)₂CH | H | CH₃ | OCH₃ | |
| O | O | CH₃ | CH₃CH₂CH₂CH₂— | H | CH₃ | CH₃ | |
| O | O | CH₃ | CH₃CH₂CH₂CH₂— | H | CH₃ | SCH₃ | |
| O | O | CH₃ | CH₃CH₂CH₂CH₂— | H | CH₃ | OCH₃ | |
| O | O | CH₃ | CH₃(CH₃)CH₂ | H | OCH₃ | OCH₃ | |
| O | O | CH₃ | CH₃CH₂CH(CH₃) | H | CH₃ | OCH₃ | |
| O | O | CH₃ | (CH₃)₃C | H | CH₃ | OCH₃ | |
| S | S | H | H | H | CH₃ | CH₃ | |
| S | S | H | H | H | CH₃ | OCH₃ | |
| S | S | H | H | H | CH₃ | OC₂H₅ | |
| S | S | H | H | H | CH₃ | CH₂OCH₃ | |
| S | S | H | H | H | OCH₃ | OCH₃ | |
| S | S | H | H | H | OCH₃ | SCH₃ | |
| S | S | H | H | H | OCH₃ | CH(OCH₃)₂ | |
| S | S | H | H | CH₃ | CH₃ | OCH₃ | |
| S | S | H | H | CH₃ | OCH₃ | OCH₃ | |
| S | S | H | CH₃ | H | CH₃ | CH₃ | |
| S | S | H | CH₃ | H | CH₃ | OCH₃ | |
| S | S | H | CH₃ | H | OCH₃ | OCH₃ | |
| S | S | H | CH₃ | H | OCH₃ | OC₂H₅ | |
| S | S | H | CH₃CH₂ | H | CH₃ | OCH₃ | |
| S | S | H | CH₃CH₂ | H | OCH₃ | OC₂H₅ | |
| S | S | H | CH₃CH₂ | H | OCH₃ | O—CH(—O—CH₂CH₂—) | |
| S | S | H | CH₃CH₂CH₂ | H | CH₃ | CH₃ | |
| S | S | H | CH₃CH₂CH₂ | H | CH₃ | O—CH(—O—CH₂CH₂—) | |
| S | S | H | CH₃CH₂CH₂ | H | OCH₃ | OCH₃ | |
| S | S | H | (CH₃)₂CH | H | CH₃ | OCH₃ | |
| S | S | H | CH₃CH₂CH₂CH₂ | H | CH₃ | CH₃ | |
| S | S | H | CH₃CH₂CH₂CH₂ | H | CH₃ | OCH₃ | |
| S | S | H | CH₃CH₂CH₂CH₂ | H | OCH₃ | OCH₃ | |
| S | S | H | CH₃CH₂CH(CH₃) | H | CH₃ | OCH₃ | |
| S | S | H | (CH₃)₃C | H | CH₃ | OCH₃ | |
| S | S | CH₃ | CH₃ | H | CH₃ | CH₃ | |
| S | S | CH₃ | CH₃ | H | CH₃ | OCH₃ | |
| S | S | CH₃ | CH₃ | H | CH₃ | OC₂H₅ | |
| S | S | CH₃ | CH₃ | H | CH₃ | CH₂OCH₃ | |
| S | S | CH₃ | CH₃ | H | OCH₃ | OCH₃ | |
| S | S | CH₃ | CH₃ | CH₃ | CH₃ | CH₃ | |
| S | S | CH₃ | CH₃ | CH₃ | CH₃ | OCH₃ | |
| S | S | CH₃ | CH₃CH₂ | H | CH₃ | OCH₃ | |
| S | S | CH₃ | CH₃CH₂ | H | OCH₃ | OCH₃ | |
| S | S | CH₃ | CH₃CH₂CH₂ | H | CH₃ | CH₃ | |
| S | S | CH₃ | CH₃CH₂CH₂ | H | CH₃ | SCH₃ | |
| S | S | CH₃ | CH₃CH₂CH₂ | H | OCH₃ | OCH₃ | |
| S | S | CH₃ | (CH₃)₂CH | H | CH₃ | OCH₃ | |
| S | S | CH₃ | CH₃CH₂CH₂CH₂— | H | CH₃ | CH₃ | |
| S | S | CH₃ | CH₃CH₂CH₂CH₂— | H | CH₃ | OCH₃ | |
| S | S | CH₃ | CH₃CH(CH₃)CH₂ | H | OCH₃ | OCH₃ | |
| S | S | CH₃ | CH₃CH₂CH(CH₃) | H | OCH₃ | OCH₃ | |
| S | S | CH₃ | (CH₃)₃C | H | CH₃ | OCH₃ | |
| SO₂ | SO₂ | H | H | H | CH₃ | CH₃ | |
| SO₂ | SO₂ | H | H | H | CH₃ | OCH₃ | |
| SO₂ | SO₂ | H | H | H | CH₃ | OC₂H₅ | |
| SO₂ | SO₂ | H | H | H | CH₃ | CH₂OCH₃ | |

TABLE Ib-continued

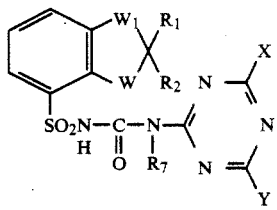

| $W_1$ | W | $R_1$ | $R_2$ | $R_7$ | X | Y | m.p. (°C.) |
|---|---|---|---|---|---|---|---|
| $SO_2$ | $SO_2$ | H | H | H | $OCH_3$ | $OCH_3$ | |
| $SO_2$ | $SO_2$ | H | H | H | $OCH_3$ | $SCH_3$ | |
| $SO_2$ | $SO_2$ | H | H | H | $OCH_3$ | $CH(OCH_3)_2$ | |
| $SO_2$ | $SO_2$ | H | H | $CH_3$ | $CH_3$ | $OCH_3$ | |
| $SO_2$ | $SO_2$ | H | H | $CH_3$ | $OCH_3$ | $OCH_3$ | |
| $SO_2$ | $SO_2$ | H | $CH_3$ | H | $CH_3$ | $CH_3$ | |
| $SO_2$ | $SO_2$ | H | $CH_3$ | H | $CH_3$ | $OCH_3$ | |
| $SO_2$ | $SO_2$ | H | $CH_3$ | H | $OCH_3$ | $OCH_3$ | |
| $SO_2$ | $SO_2$ | H | $CH_3$ | H | $OCH_3$ | $OC_2H_5$ | |
| $SO_2$ | $SO_2$ | H | $CH_3CH_2$ | H | $CH_3$ | $OCH_3$ | |
| $SO_2$ | $SO_2$ | H | $CH_3CH_2$ | H | $OCH_3$ | $OCH_3$ | |
| $SO_2$ | $SO_2$ | H | $CH_3CH_2$ | H | $OCH_3$ | $OCH_2H_5$ | |
| $SO_2$ | $SO_2$ | H | $CH_3CH_2$ | H | $OCH_3$ | $\begin{array}{c}O\\/\\CH\\\backslash\\O\end{array}\Bigg]$ | |
| $SO_2$ | $SO_2$ | H | $CH_3CH_2CH_2$ | H | $CH_3$ | $CH_3$ | |
| $SO_2$ | $SO_2$ | H | $CH_3CH_2CH_2$ | H | $CH_3$ | $OCH_3$ | |
| $SO_2$ | $SO_2$ | H | $(CH_3)_2CH$ | H | $CH_3$ | $OCH_3$ | |
| $SO_2$ | $SO_2$ | H | $CH_3CH_2CH_2CH_2$ | H | $CH_3$ | $CH_3$ | |
| $SO_2$ | $SO_2$ | H | $CH_3CH_2CH_2CH_2$ | H | $CH_3$ | $OCH_3$ | |
| $SO_2$ | $SO_2$ | H | $CH_3CH_2CH_2CH_2$ | H | $OCH_3$ | $OCH_3$ | |
| $SO_2$ | $SO_2$ | H | $CH_3CH(CH_3)CH_2$ | H | $OCH_3$ | $OCH_3$ | |
| $SO_2$ | $SO_2$ | H | $CH_3CH_2CH(CH_3)$ | H | $CH_3$ | $OCH_3$ | |
| $SO_2$ | $SO_2$ | H | $(CH_3)_3C$ | H | $CH_3$ | $OCH_3$ | |
| $SO_2$ | $SO_2$ | $CH_3$ | $CH_3$ | H | $CH_3$ | $CH_3$ | |
| $SO_2$ | $SO_2$ | $CH_3$ | $CH_3$ | H | $CH_3$ | $OCH_3$ | |
| $SO_2$ | $SO_2$ | $CH_3$ | $CH_3$ | H | $CH_3$ | $OC_2H_5$ | |
| $SO_2$ | $SO_2$ | $CH_3$ | $CH_3$ | H | $CH_3$ | $CH_2OCH_3$ | |
| $SO_2$ | $SO_2$ | $CH_3$ | $CH_3$ | H | $OCH_3$ | $OCH_3$ | |
| $SO_2$ | $SO_2$ | $CH_3$ | $CH_3$ | $CH_3$ | $CH_3$ | $CH_3$ | |
| $SO_2$ | $SO_2$ | $CH_3$ | $CH_3$ | $CH_3$ | $CH_3$ | $OCH_3$ | |
| $SO_2$ | $SO_2$ | $CH_3$ | $CH_3CH_2$ | H | $CH_2$ | $OCH_3$ | |
| $SO_2$ | $SO_2$ | $CH_3$ | $CH_3CH_2$ | H | $OCH_3$ | $OCH_3$ | |
| $SO_2$ | $SO_2$ | $CH_3$ | $CH_3CH_2CH_2$ | H | $CH_3$ | $CH_3$ | |
| $SO_2$ | $SO_2$ | $CH_3$ | $CH_3CH_2CH_2$ | H | $CH_3$ | $SCH_3$ | |
| $SO_2$ | $SO_2$ | $CH_3$ | $CH_3CH_2CH_2$ | H | $OCH_3$ | $OCH_3$ | |
| $SO_2$ | $SO_2$ | $CH_3$ | $(CH_3)_2CH$ | H | $CH_2$ | $OCH_3$ | |
| $SO_2$ | $SO_2$ | $CH_3$ | $CH_3CH_2CH_2CH_2-$ | H | $CH_3$ | $CH_3$ | |
| $SO_2$ | $SO_2$ | $CH_3$ | $CH_3CH_2CH_2CH_2-$ | H | $CH_3$ | $OCH_3$ | |
| $SO_2$ | $SO_2$ | $CH_3$ | $CH_3CH_2CH_2CH_2-$ | H | $CH_3$ | $OCH_3$ | |
| $SO_2$ | $SO_2$ | $CH_3$ | $CH_3CH(CH_3)CH_2$ | H | $OCH_3$ | $OCH_3$ | |
| $SO_2$ | $SO_2$ | $CH_3$ | $CH_3CH_2CH(CH_3)$ | H | $CH_3$ | $OCH_3$ | |
| $SO_2$ | $SO_2$ | $CH_3$ | $(CH_3)_3C$ | H | $CH_3$ | $OCH_3$ | |
| SO | SO | H | H | H | $CH_3$ | $CH_3$ | |
| SO | SO | H | H | H | $CH_3$ | $OCH_3$ | |
| SO | SO | H | $CH_3$ | H | $CH_3$ | $OCH_3$ | |
| SO | SO | H | $CH_3$ | H | $CH_3$ | $SCH_3$ | |
| SO | SO | $CH_3$ | $CH_3$ | H | $CH_3$ | $CH_3$ | |
| SO | SO | $CH_3$ | $CH_3$ | H | $CH_3$ | $OCH_3$ | |
| SO | SO | $CH_3$ | $CH_3$ | H | $CH_3$ | $SCH_3$ | |
| SO | SO | $CH_3$ | $CH_3$ | H | $OCH_3$ | $OCH_3$ | |
| SO | SO | $CH_3$ | $CH_3$ | H | $OCH_3$ | $OC_2H_5$ | |
| O | S | H | H | H | $CH_3$ | $CH_3$ | |
| O | S | H | H | H | $CH_3$ | $OCH_3$ | |
| O | S | H | H | H | $OCH_3$ | $OCH_3$ | |
| O | S | H | $CH_3$ | H | $CH_3$ | $OCH_3$ | |
| O | S | $CH_3$ | $CH_3$ | H | $CH_3$ | $CH_3$ | |
| O | S | $CH_3$ | $CH_3$ | H | $CH_3$ | $OCH_3$ | |
| O | S | $CH_3$ | $CH_3$ | H | $OCH_3$ | $OCH_3$ | |
| O | SO | H | H | H | $CH_3$ | $OCH_3$ | |
| O | SO | H | $CH_3$ | H | $CH_3$ | $OCH_3$ | |
| O | SO | $CH_3$ | $CH_3$ | H | $CH_3$ | $OCH_3$ | |
| O | $SO_2$ | H | H | H | $CH_3$ | $CH_3$ | |
| O | $SO_2$ | H | H | H | $CH_3$ | $OCH_3$ | |
| O | $SO_2$ | H | $CH_3$ | H | $CH_3$ | $OCH_3$ | |

TABLE Ib-continued

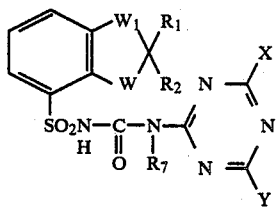

| W₁ | W | R₁ | R₂ | R₇ | X | Y | m.p. (°C.) |
|---|---|---|---|---|---|---|---|
| O | SO₂ | CH₃ | CH₃ | H | CH₃ | OCH₃ | |
| O | SO₂ | CH₃ | CH₃ | H | OCH₃ | OCH₃ | |
| S | O | CH₃ | CH₃ | H | CH₃ | CH₃ | |
| S | O | CH₃ | CH₃ | H | CH₃ | OCH₃ | |
| SO | S | CH₃ | CH₃ | H | CH₃ | OCH₃ | |
| SO₂ | O | H | H | H | CH₃ | OCH₃ | |
| SO₂ | O | CH₃ | H | H | CH₃ | OCH₃ | |
| SO | S | CH₃ | CH₃ | H | CH₃ | OCH₃ | |
| SO₂ | S | H | H | H | CH₃ | OCH₃ | |
| SO₂ | S | CH₃ | CH₃ | H | CH₃ | OCH₃ | |
| S | SO | H | H | H | CH₃ | OCH₃ | |
| S | SO | CH₃ | CH₃ | H | CH₃ | OCH₃ | |
| S | SO₂ | H | H | H | CH₃ | OCH₃ | |
| S | SO₂ | H | CH₃ | H | CH₃ | OCH₃ | |
| S | SO₂ | CH₃ | CH₃ | H | CH₃ | OCH₃ | |
| SO₂ | SO | CH₃ | CH₃ | H | CH₃ | OCH₃ | |
| SO | SO₂ | H | H | H | CH₃ | OCH₃ | |
| SO | SO₂ | CH₃ | CH₃ | H | CH₃ | OCH₃ | |

TABLE Ic

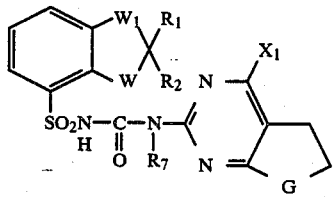

| W₁ | W | R₁ | R₂ | R₇ | G | X₁ | m.p. (°C.) |
|---|---|---|---|---|---|---|---|
| O | O | H | H | H | O | CH₃ | |
| O | O | H | H | H | O | OCH₃ | |
| O | O | H | H | H | CH₂ | CH₃ | |
| O | O | H | H | CH₃ | CH₂ | CH₃ | |
| O | O | H | H | CH₃ | O | CH₃ | |
| O | O | H | H | CH₃ | O | OCH₃ | |
| O | O | H | CH₃ | H | O | CH₃ | |
| O | O | H | CH₃ | H | O | OCH₃ | |
| O | O | H | CH₃CH₂ | H | O | OCH₃ | |
| O | O | H | CH₃CH₂CH₂ | H | O | OCH₃ | |
| O | O | H | (CH₃)₂CH | H | O | OCH₃ | |
| O | O | H | CH₃CH₂CH₂CH₂ | H | O | OCH₃ | |
| O | O | H | CH₃CH(CH₃)CH₃ | H | CH₂ | CH₃ | |
| O | O | H | (CH₃)₃C | H | O | CH₃ | |
| O | O | CH₃ | CH₃ | H | O | CH₃ | |
| O | O | CH₃ | CH₃ | H | O | OCH₃ | |
| O | O | CH₃ | CH₃ | H | CH₂ | CH₃ | |
| O | O | CH₃ | CH₃ | H | CH₂ | OCH₃ | |
| O | O | CH₃ | CH₃ | CH₃ | CH₂ | CH₃ | |
| O | O | CH₃ | CH₃ | CH₃ | O | CH₃ | |
| O | O | CH₃ | CH₃ | CH₃ | O | OCH₃ | |
| O | O | CH₃ | CH₃CH₂ | H | O | CH₃ | |
| O | O | CH₃ | CH₃CH₂CH₂ | H | O | CH₃ | |
| O | O | CH₃ | (CH₃)₂CH | H | O | CH₃ | |
| O | O | CH₃ | CH₃CH₂CH₂CH₂ | H | O | CH₃ | |
| O | O | CH₃ | CH₃CH(CH₃)CH₃ | H | O | CH₃ | |
| O | O | CH₃ | (CH₃)₃C | H | O | CH₃ | |
| S | S | H | H | H | O | CH₃ | |
| S | S | H | H | H | O | OCH₃ | |
| S | S | H | H | H | CH₂ | CH₃ | |
| S | S | H | H | CH₃ | CH₂ | CH₃ | |
| S | S | H | H | CH₃ | O | CH₃ | |
| S | S | H | H | CH₃ | O | OCH₃ | |
| S | S | H | CH₃ | H | O | CH₃ | |

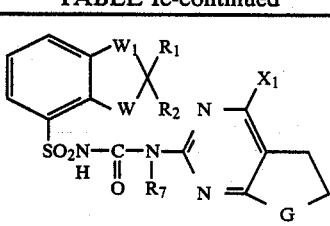

| W₁ | W | R₁ | R₂ | R₇ | G | X₁ | m.p. (°C.) |
|---|---|---|---|---|---|---|---|
| S | S | H | CH₃ | H | O | OCH₃ | |
| S | S | H | CH₃CH₂ | H | CH₂ | CH₃ | |
| S | S | H | CH₃CH₂CH₂ | H | O | OCH₃ | |
| S | S | H | CH₃CH₂CH₂CH₂ | H | O | OCH₃ | |
| S | S | CH₃ | CH₃ | H | O | CH₃ | |
| S | S | CH₃ | CH₃ | H | O | OCH₃ | |
| S | S | CH₃ | CH₃ | H | OCH₃ | CH₃ | |
| S | S | CH₃ | CH₃ | H | OCH₃ | OCH₃ | |
| S | S | CH₃ | CH₃ | CH₃ | CH₂ | CH₃ | |
| S | S | CH₃ | CH₃ | CH₃ | O | CH₃ | |
| S | S | CH₃ | CH₃ | CH₃ | O | OCH₃ | |
| S | S | CH₃ | CH₃CH₂ | H | O | CH₃ | |
| S | S | CH₃ | CH₃CH₂CH₂ | H | O | CH₃ | |
| S | S | CH₃ | (CH₃)₂CH | H | O | CH₃ | |
| S | S | CH₃ | CH₃CH₂CH₂CH₂ | H | O | CH₃ | |
| S | S | CH₃ | CH₃CH(CH₃)CH₂ | H | O | CH₃ | |
| S | S | CH₃ | (CH₃)₃C | H | O | CH₃ | |
| SO₂ | SO₂ | H | H | H | O | CH₃ | |
| SO₂ | SO₂ | H | H | H | O | OCH₃ | |
| SO₂ | SO₂ | H | H | H | CH₂ | CH₃ | |
| SO₂ | SO₂ | H | H | H | CH₂ | OCH₃ | |
| SO₂ | SO₂ | H | H | CH₃ | CH₂ | CH₃ | |
| SO₂ | SO₂ | H | H | CH₃ | O | CH₃ | |
| SO₂ | SO₂ | H | H | CH₃ | O | OCH₃ | |
| SO₂ | SO₂ | H | CH₃ | H | O | CH₃ | |
| SO₂ | SO₂ | H | CH₃ | H | O | OCH₃ | |
| SO₂ | SO₂ | H | CH₃CH₂ | H | CH₂ | OCH₃ | |
| SO₂ | SO₂ | H | CH₃CH₂CH₃ | H | CH₂ | OCH₃ | |
| SO₂ | SO₂ | H | CH₃CH₂CH₃ | H | O | OCH₃ | |
| SO₂ | SO₂ | CH₃ | CH₃ | H | O | CH₃ | |
| SO₂ | SO₂ | CH₃ | CH₃ | H | O | OCH₃ | |
| SO₂ | SO₂ | CH₃ | CH₃ | H | CH₂ | CH₃ | |
| SO₂ | SO₂ | CH₃ | CH₃ | H | CH₂ | OCH₃ | |
| SO₂ | SO₂ | CH₃ | CH₃ | CH₃ | CH₂ | CH₃ | |

TABLE Ic-continued

| $W_1$ | W | $R_1$ | $R_2$ | $R_7$ | G | $X_1$ | m.p. (°C.) |
|---|---|---|---|---|---|---|---|
| $SO_2$ | $SO_2$ | $CH_3$ | $CH_3$ | $CH_3$ | O | $CH_3$ | |
| $SO_2$ | $SO_2$ | $CH_3$ | $CH_3$ | $CH_3$ | O | $OCH_3$ | |
| $SO_2$ | $SO_2$ | $CH_3$ | $CH_3CH_2$ | H | O | $CH_3$ | |
| $SO_2$ | $SO_2$ | $CH_3$ | $CH_3CH_2CH_2$ | H | O | $CH_3$ | |
| $SO_2$ | $SO_2$ | $CH_3$ | $(CH_3)_2CH$ | H | O | $CH_3$ | |
| $SO_2$ | $SO_2$ | $CH_3$ | $CH_3CH_2CH_2CH_2$ | H | O | $CH_3$ | |
| $SO_2$ | $SO_2$ | $CH_3$ | $CH_3CH(CH_3)CH_2$ | H | O | $CH_3$ | |
| $SO_2$ | $SO_2$ | $CH_3$ | $(CH_3)_3C$ | H | O | $CH_3$ | |
| SO | SO | H | H | H | $CH_2$ | $CH_3$ | |
| SO | SO | H | H | H | O | $OCH_3$ | |
| SO | SO | $CH_3$ | $CH_3$ | H | $CH_2$ | $CH_3$ | |
| SO | SO | $CH_3$ | $CH_3$ | H | O | $CH_3$ | |
| O | S | H | H | H | O | $CH_3$ | |
| O | S | $CH_3$ | $CH_3$ | H | O | $CH_3$ | |
| O | SO | H | H | H | O | $CH_3$ | |
| O | SO | $CH_3$ | $CH_3$ | H | O | $CH_3$ | |
| O | $SO_2$ | H | H | H | O | $CH_3$ | |
| O | $SO_2$ | $CH_3$ | $CH_3$ | H | O | $CH_3$ | |
| S | O | H | H | H | O | $CH_3$ | |
| SO | O | H | H | H | O | $CH_3$ | |
| $SO_2$ | O | H | H | H | O | $CH_3$ | |
| SO | S | $CH_3$ | $CH_3$ | H | O | $CH_3$ | |
| $SO_2$ | S | H | H | H | O | $CH_3$ | |
| $SO_2$ | S | $CH_3$ | $CH_3$ | H | O | $CH_3$ | |
| S | SO | $CH_3$ | $CH_3$ | H | O | $CH_3$ | |
| S | $SO_2$ | $CH_3$ | $CH_3$ | H | O | $CH_3$ | |
| $SO_2$ | SO | H | H | H | O | $CH_3$ | |
| SO | $SO_2$ | H | H | H | O | $CH_3$ | |

TABLE Id

| $W_1$ | W | $R_1$ | $R_2$ | $R_7$ | $X_1$ | m.p. (°C.) |
|---|---|---|---|---|---|---|
| O | O | H | H | H | $CH_3$ | |
| O | O | H | H | H | $OCH_3$ | |
| O | O | H | H | $CH_3$ | $CH_3$ | |
| O | O | H | H | $CH_3$ | $OCH_3$ | |
| O | O | H | $CH_3$ | H | $CH_3$ | |
| O | O | H | $CH_3CH_2$ | H | $CH_3$ | |
| O | O | H | $CH_3CH_2CH_2$ | H | $CH_3$ | |
| O | O | H | $(CH_3)_2CH$ | H | $CH_3$ | |
| O | O | H | $CH_3CH_2CH_2CH_2$ | H | $CH_3$ | |
| O | O | H | $CH_3CH(CH_3)CH_3$ | H | $CH_3$ | |
| O | O | H | $(CH_3)_3C$ | H | $CH_3$ | |
| O | O | $CH_3$ | $CH_3$ | H | $OCH_3$ | |
| O | O | $CH_3$ | $CH_3$ | H | $CH_3$ | |
| O | O | $CH_3$ | $CH_3$ | $CH_3$ | $CH_3$ | |
| O | O | $CH_3$ | $CH_3$ | $CH_3$ | $OCH_3$ | |
| O | O | $CH_3$ | $CH_3CH_2$ | H | $CH_3$ | |
| O | O | $CH_3$ | $CH_3CH_2CH_2$ | H | $CH_3$ | |
| O | O | $CH_3$ | $(CH_3)_2CH$ | H | CH | |
| O | O | $CH_3$ | $CH_3CH_2CH_2CH_2$ | H | $CH_3$ | |
| O | O | $CH_3$ | $CH_3CH(CH_3)CH_3$ | H | $CH_3$ | |
| O | O | $CH_3$ | $(CH_3)_3C$ | H | $CH_3$ | |
| S | S | H | H | H | $CH_3$ | |
| S | S | H | H | H | $OCH_3$ | |
| S | S | H | H | $CH_3$ | $CH_3$ | |

TABLE Id-continued

| $W_1$ | W | $R_1$ | $R_2$ | $R_7$ | $X_1$ | m.p.(°C.) |
|---|---|---|---|---|---|---|
| S | S | H | H | $CH_3$ | $OCH_3$ | |
| S | S | H | $CH_3$ | H | $CH_3$ | |
| S | S | H | $CH_3CH_2$ | H | $CH_3$ | |
| S | S | H | $CH_3CH_2CH_2$ | H | $CH_3$ | |
| S | S | H | $(CH_3)_2CH$ | H | $CH_3$ | |
| S | S | H | $CH_3CH_2CH_2CH_2$ | H | $CH_3$ | |
| S | S | H | $CH_3CH(CH_3)CH_3$ | H | $CH_3$ | |
| S | S | H | $(CH_3)_3C$ | H | $CH_3$ | |
| S | S | $CH_3$ | $CH_3$ | H | $OCH_3$ | |
| S | S | $CH_3$ | $CH_3$ | H | $CH_3$ | |
| S | S | $CH_3$ | $CH_3$ | $CH_3$ | $CH_3$ | |
| S | S | $CH_3$ | $CH_3$ | $CH_3$ | $OCH_3$ | |
| S | S | $CH_3$ | $CH_3CH_2$ | H | $CH_3$ | |
| S | S | $CH_3$ | $CH_3CH_2CH_2$ | H | $CH_3$ | |
| S | S | $CH_3$ | $(CH_3)_2CH$ | H | $CH_3$ | |
| S | S | $CH_3$ | $CH_3CH_2CH_2CH_2$ | H | $CH_3$ | |
| S | S | $CH_3$ | $CH_3CH(CH_3)CH_3$ | H | $CH_3$ | |
| S | S | $CH_3$ | $(CH_3)_3C$ | H | $CH_3$ | |
| $SO_2$ | $SO_2$ | H | H | H | $CH_3$ | |
| $SO_2$ | $SO_2$ | H | H | H | $OCH_3$ | |
| $SO_2$ | $SO_2$ | H | H | $CH_3$ | $CH_3$ | |
| $SO_2$ | $SO_2$ | H | H | $CH_3$ | $OCH_3$ | |
| $SO_2$ | $SO_2$ | H | $CH_3$ | H | $CH_3$ | |
| $SO_2$ | $SO_2$ | H | $CH_3$ | H | $CH_3$ | |
| $SO_2$ | $SO_2$ | H | $CH_3CH_2$ | H | $CH_3$ | |
| $SO_2$ | $SO_2$ | H | $CH_3CH_2CH_2$ | H | $CH_3$ | |
| $SO_2$ | $SO_2$ | H | $(CH_3)_2CH$ | H | $CH_3$ | |
| $SO_2$ | $SO_2$ | H | $CH_3CH_2CH_2CH_2$ | H | $CH_3$ | |
| $SO_2$ | $SO_2$ | H | $CH_3CH(CH_3)CH_3$ | H | $CH_3$ | |
| $SO_2$ | $SO_2$ | H | $(CH_3)_3C$ | H | $CH_3$ | |
| $SO_2$ | $SO_2$ | $CH_3$ | $CH_3$ | H | $OCH_3$ | |
| $SO_2$ | $SO_2$ | $CH_3$ | $CH_3$ | H | $CH_3$ | |
| $SO_2$ | $SO_2$ | $CH_3$ | $CH_3$ | $CH_3$ | $CH_3$ | |
| $SO_2$ | $SO_2$ | $CH_3$ | $CH_3$ | $CH_3$ | $OCH_3$ | |
| $SO_2$ | $SO_2$ | $CH_3$ | $CH_3CH_2$ | H | $CH_3$ | |
| $SO_2$ | $SO_2$ | $CH_3$ | $CH_3CH_2CH_2$ | H | $CH_3$ | |
| $SO_2$ | $SO_2$ | $CH_3$ | $(CH_3)_2CH$ | H | $CH_3$ | |
| $SO_2$ | $SO_2$ | $CH_3$ | $CH_3CH_2CH_2CH_2$ | H | $CH_3$ | |
| $SO_2$ | $SO_2$ | $CH_3$ | $CH_3(CH_3)CH_3$ | H | $CH_3$ | |
| $SO_2$ | $SO_2$ | $CH_3$ | $(CH_3)_3C$ | H | $CH_3$ | |
| SO | SO | $CH_3$ | $CH_3$ | H | $CH_3$ | |
| SO | SO | $CH_3$ | $CH_3$ | H | $OCH_3$ | |
| O | S | H | H | H | $CH_3$ | |
| O | SO | $CH_3$ | $CH_3$ | H | $CH_3$ | |
| O | $SO_2$ | $CH_3$ | $CH_3$ | H | $CH_3$ | |
| S | O | H | H | H | $CH_3$ | |
| SO | O | H | H | H | $CH_3$ | |
| $SO_2$ | O | H | H | H | $CH_3$ | |
| SO | S | H | H | H | $CH_3$ | |
| S | $SO_2$ | H | H | H | $CH_3$ | |
| S | SO | H | H | H | $CH_3$ | |
| S | $SO_2$ | $CH_3$ | $CH_3$ | H | $CH_3$ | |
| $SO_2$ | SO | H | H | H | $CH_3$ | |
| SO | $SO_2$ | H | H | H | $CH_3$ | |

TABLE Ie

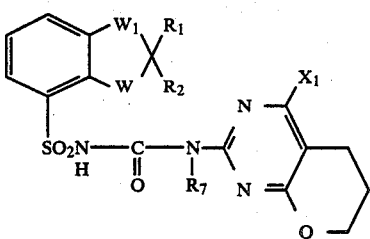

| W₁ | W | R₁ | R₂ | R₇ | X₁ | m.p.(°C.) |
|---|---|---|---|---|---|---|
| O | O | H | H | H | CH₃ | |
| O | O | H | H | H | OCH₃ | |
| O | O | H | H | CH₃ | CH₃ | |
| O | O | H | H | CH₃ | OCH₃ | |
| O | O | H | CH₃ | H | CH₃ | |
| O | O | H | CH₃CH₂ | H | CH₃ | |
| O | O | H | CH₃CH₂CH₂ | H | CH₃ | |
| O | O | H | (CH₃)₂CH | H | CH₃ | |
| O | O | H | CH₃CH₂CH₂CH₂ | H | CH₃ | |
| O | O | H | CH₃CH(CH₃)CH₃ | H | CH₃ | |
| O | O | H | (CH₃)₃C | H | CH₃ | |
| O | O | CH₃ | CH₃ | H | OCH₃ | |
| O | O | CH₃ | CH₃ | CH₃ | CH₃ | |
| O | O | CH₃ | CH₃ | CH₃ | OCH₃ | |
| O | O | CH₃ | CH₃CH₂ | H | CH₃ | |
| O | O | CH₃ | CH₃CH₂CH₂ | H | CH₃ | |
| O | O | CH₃ | (CH₃)₂CH | H | CH₃ | |
| O | O | CH₃ | CH₃CH₂CH₂CH₂ | H | CH₃ | |
| O | O | CH₃ | CH₃CH(CH₃)CH₃ | H | CH₃ | |
| O | O | CH₃ | (CH₃)₃C | H | CH₃ | |
| S | S | H | H | H | CH₃ | |
| S | S | H | H | H | OCH₃ | |
| S | S | H | H | CH₃ | CH₃ | |
| S | S | H | H | CH₃ | OCH₃ | |
| S | S | H | CH₃ | H | CH₃ | |
| S | S | H | CH₃CH₂ | H | CH₃ | |
| S | S | H | CH₃CH₂CH₂ | H | CH₃ | |
| S | S | H | (CH₃)₂CH | H | CH₃ | |
| S | S | H | CH₃CH₂CH₂CH₂ | H | CH₃ | |
| S | S | H | CH₃CH(CH₃)CH₃ | H | CH₃ | |
| S | S | H | (CH₃)₃C | H | CH₃ | |
| S | S | CH₃ | CH₃ | H | OCH₃ | |
| S | S | CH₃ | CH₃ | CH₃ | CH₃ | |
| S | S | CH₃ | CH₃ | CH₃ | OCH₃ | |
| S | S | CH₃ | CH₃CH₂ | H | CH₃ | |
| S | S | CH₃ | CH₃CH₂CH₂ | H | CH₃ | |
| S | S | CH₃ | (CH₃)₂CH | H | CH₃ | |
| S | S | CH₃ | CH₃CH₂CH₂CH₂ | H | CH₃ | |
| S | S | CH₃ | CH₃CH(CH₃)CH₃ | H | CH₃ | |
| S | S | CH₃ | (CH₃)₃C | H | CH₃ | |
| SO₂ | SO₂ | H | H | H | CH₃ | |
| SO₂ | SO₂ | H | H | H | OCH₃ | |
| SO₂ | SO₂ | H | H | CH₃ | CH₃ | |
| SO₂ | SO₂ | H | H | CH₃ | OCH₃ | |
| SO₂ | SO₂ | H | CH₃ | H | CH₃ | |
| SO₂ | SO₂ | H | CH₃CH₂ | H | CH₃ | |
| SO₂ | SO₂ | H | CH₃CH₂CH₂ | H | CH₃ | |
| SO₂ | SO₂ | H | (CH₃)₂CH | H | CH₃ | |
| SO₂ | SO₂ | H | CH₃CH₂CH₂CH₂ | H | CH₃ | |
| SO₂ | SO₂ | H | CH₃CH(CH₃)CH₃ | H | CH₃ | |
| SO₂ | SO₂ | H | (CH₃)₃C | H | CH₃ | |
| SO₂ | SO₂ | CH₃ | CH₃ | H | OCH₃ | |
| SO₂ | SO₂ | CH₃ | CH₃ | CH₃ | CH₃ | |
| SO₂ | SO₂ | CH₃ | CH₃ | CH₃ | OCH₃ | |
| SO₂ | SO₂ | CH₃ | CH₃CH₂ | H | CH₃ | |
| SO₂ | SO₂ | CH₃ | CH₃CH₂CH₂ | H | CH₃ | |
| SO₂ | SO₂ | CH₃ | (CH₃)₂CH | H | CH₃ | |
| SO₂ | SO₂ | CH₃ | CH₃CH₂CH₂CH₂ | H | CH₃ | |
| SO₂ | SO₂ | CH₃ | CH₃CH(CH₃)CH₃ | H | CH₃ | |
| SO₂ | SO₂ | CH₃ | (CH₃)₃C | H | CH₃ | |
| SO | SO | CH₃ | CH₃ | H | CH₃ | |
| SO | SO | CH₃ | CH₃ | H | OCH₃ | |
| O | S | H | H | H | CH₃ | |
| O | SO | CH₃ | CH₃ | H | CH₃ | |
| O | SO₂ | CH₃ | CH₃ | H | CH₃ | |
| S | O | H | H | H | CH₃ | |
| SO | O | H | H | H | CH₃ | |
| SO₂ | O | H | H | H | CH₃ | |
| SO | S | H | H | H | CH₃ | |
| S | SO₂ | H | H | H | CH₃ | |
| S | SO | H | H | H | CH₃ | |
| S | SO₂ | CH₃ | CH₃ | H | CH₃ | |
| SO₂ | SO | H | H | H | CH₃ | |
| SO | SO₂ | H | H | H | CH₃ | |

TABLE If

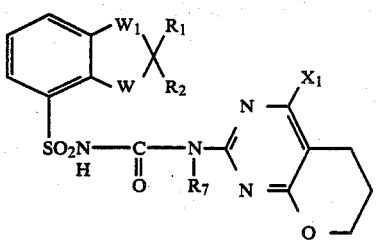

| W₁ | W | R₁ | R₂ | R₇ | X₂ | Y₂ | m.p. (°C.) |
|---|---|---|---|---|---|---|---|
| O | O | H | H | H | CH₃ | OCH₃ | |
| O | O | H | H | H | CH₃CH₂ | SCH₃ | |
| O | O | H | H | H | CH₂CF₃ | OCH₃ | |
| O | O | H | H | CH₃ | CH₃ | OCH₃ | |
| O | O | H | CH₃ | H | CH₃CH₂CH₂ | OC₂H₅ | |
| O | O | H | CH₃CH₂ | H | (CH₃)₂CH | SC₂H₅ | |
| O | O | H | CH₃CH₂CH₂ | H | CH₃ | OCH₃ | |
| O | O | H | (CH₃)₂CH | H | CH₃ | OCH₃ | |
| O | O | H | CH₃CH₂CH₂CH₂ | H | CH₃ | OCH₃ | |
| O | O | H | CH₃CH(CH₃)CH₂ | H | CH₃ | OCH₃ | |
| O | O | H | (CH₃)₃C | H | CH₃ | OCH₃ | |
| O | O | CH₃ | CH₃ | H | CH₃ | OCH₃ | |
| O | O | CH₃ | CH₃ | H | CH₃ | SCH₃ | |
| O | O | CH₃ | CH₃ | H | CH₃CH₂ | OCH₃ | |
| O | O | CH₃ | CH₃ | H | CH₂CF₃ | OCH₃ | |
| O | O | CH₃ | CH₃ | H | CH₂CF₃ | SCH₃ | |
| O | O | CH₃ | CH₃ | CH₃ | CH₃ | OCH₃ | |
| O | O | CH₃ | CH₃CH₂ | H | CH₃ | OCH₃ | |
| O | O | CH₃ | CH₃CH₂CH₂ | H | CH₃ | OCH₃ | |
| O | O | CH₃ | (CH₃)₂CH | H | CH₃ | OCH₃ | |
| O | O | CH₃ | CH₃CH₂CH₂CH₂ | H | CH₃ | OCH₃ | |
| O | O | CH₃ | CH₃CH(CH₃)CH₂ | H | CH₃ | OCH₃ | |
| O | O | CH₃ | (CH₃)₃C | H | CH₃ | OCH₃ | |
| S | S | H | H | H | CH₃ | OCH₃ | |
| S | S | H | H | H | CH₃CH₂ | SCH₃ | |
| S | S | H | H | H | CH₂CF₃ | OCH₃ | |
| S | S | H | H | CH₃ | CH₃ | OCH₃ | |
| S | S | H | CH₃ | H | CH₃CH₂CH₂ | OC₂H₅ | |
| S | S | H | CH₃CH₂ | H | (CH₃)₂CH | SC₂H₅ | |
| S | S | H | CH₃CH₂CH₂ | H | CH₃ | OCH₃ | |
| S | S | H | (CH₃)₂CH | H | CH₃ | OCH₃ | |
| S | S | H | CH₃CH₂CH₂CH₂ | H | CH₃ | OCH₃ | |
| S | S | H | CH₃CH(CH₃)CH₂ | H | CH₃ | OCH₃ | |
| S | S | H | (CH₃)₃C | H | CH₃ | OCH₃ | |
| S | S | CH₃ | CH₃ | H | CH₃ | OCH₃ | |
| S | S | CH₃ | CH₃ | H | CH₃ | SCH₃ | |
| S | S | CH₃ | CH₃ | H | CH₃CH₂ | OCH₃ | |
| S | S | CH₃ | CH₃ | H | CH₂CF₃ | OCH₃ | |
| S | S | CH₃ | CH₃ | H | CH₂CF₃ | SCH₃ | |
| S | S | CH₃ | CH₃ | CH₃ | CH₃ | OCH₃ | |
| S | S | CH₃ | CH₃CH₂ | H | CH₃ | OCH₃ | |
| S | S | CH₃ | CH₃CH₂CH₂ | H | CH₃ | OCH₃ | |
| S | S | CH₃ | (CH₃)₂CH | H | CH₃ | OCH₃ | |
| S | S | CH₃ | CH₃CH₂CH₂CH₂ | H | CH₃ | OCH₃ | |

TABLE If-continued

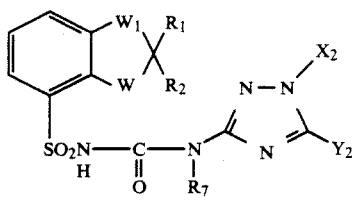

| $W_1$ | W | $R_1$ | $R_2$ | $R_7$ | $X_2$ | $Y_2$ | m.p. (°C.) |
|---|---|---|---|---|---|---|---|
| S | S | CH₃ | CH₃CH(CH₃)CH₂ | H | CH₃ | OCH₃ | |
| S | S | CH₃ | (CH₃)₃C | H | CH₃ | OCH₃ | |
| SO₂ | SO₂ | H | H | H | CH₃ | OCH₃ | |
| SO₂ | SO₂ | H | H | H | CH₃CF₂ | SCH₃ | |
| SO₂ | SO₂ | H | H | H | CH₂CH₃ | OCH₃ | |
| SO₂ | SO₂ | H | H | CH₃ | CH₃ | OCH₃ | |
| SO₂ | SO₂ | H | CH₃ | H | CH₃CH₂CH₂ | OC₂H₅ | |
| SO₂ | SO₂ | H | CH₃CH₂ | H | (CH₃)₂CH | SC₂H₅ | |
| SO₂ | SO₂ | H | CH₃CH₂CH₂ | H | CH₃ | OCH₃ | |
| SO₂ | SO₂ | H | (CH₃)₂CH | H | CH₃ | OCH₃ | |
| SO₂ | SO₂ | H | CH₃CH₂CH₂CH₂ | H | CH₃ | OCH₃ | |
| SO₂ | SO₂ | H | CH₃CH(CH₃)CH₂ | H | CH₃ | OCH₃ | |
| SO₂ | SO₂ | H | (CH₃)₃C | H | CH₃ | OCH₃ | |
| SO₂ | SO₂ | CH₃ | CH₃ | H | CH₃ | OCH₃ | |
| SO₂ | SO₂ | CH₃ | CH₃ | H | CH₃ | SCH₃ | |
| SO₂ | SO₂ | CH₃ | CH₃ | H | CH₃CH₂ | OCH₃ | |
| SO₂ | SO₂ | CH₃ | CH₃ | H | CH₂CF₃ | SCH₃ | |
| SO₂ | SO₂ | CH₃ | CH₃ | H | CH₂CF₃ | OCH₃ | |
| SO₂ | SO₂ | CH₃ | CH₃ | CH₃ | CH₃ | OCH₃ | |
| SO₂ | SO₂ | CH₃ | CH₃CH₂ | H | CH₃ | OCH₃ | |

TABLE If-continued

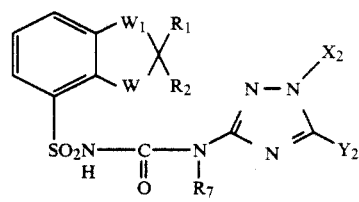

| $W_1$ | W | $R_1$ | $R_2$ | $R_7$ | $X_2$ | $Y_2$ | m.p. (°C.) |
|---|---|---|---|---|---|---|---|
| SO₂ | SO₂ | CH₃ | CH₃CH₂CH₂ | H | CH₃ | OCH₃ | |
| SO₂ | SO₂ | CH₃ | (CH₃)₂CH | H | CH₃ | OCH₃ | |
| SO₂ | SO₂ | CH₃ | CH₃CH₂CH₂CH₂ | H | CH₃ | OCH₃ | |
| SO₂ | SO₂ | CH₃ | CH₃CH(CH₃)CH₂ | H | CH₃ | OCH₃ | |
| SO₂ | SO₂ | CH₃ | (CH₃)₃C | H | CH₃ | OCH₃ | |
| SO | SO | H | H | H | CH₃ | OCH₃ | |
| SO | SO | CH₃ | CH₃ | H | CH₃ | SCH₃ | |
| O | S | H | H | H | CH₃ | OCH₃ | |
| O | SO | CH₃ | CH₃ | H | CH₃ | OCH₃ | |
| O | SO₂ | CH₃ | CH₃ | H | CH₃ | OCH₃ | |
| S | O | H | H | H | CH₃ | OCH₃ | |
| SO | O | H | H | H | CH₃ | OCH₃ | |
| SO₂ | O | H | H | H | CH₃ | OCH₃ | |
| S | SO | H | H | H | CH₃ | OCH₃ | |
| S | SO₂ | H | H | H | CH₃ | OCH₃ | |
| S | SO | H | H | H | CH₃ | OCH₃ | |
| S | SO₂ | CH₃ | CH₃ | H | CH₃ | OCH₃ | |
| SO₂ | SO | H | H | H | CH₃ | OCH₃ | |
| SO | SO₂ | H | H | H | CH₃ | OCH₃ | |

TABLE IIa

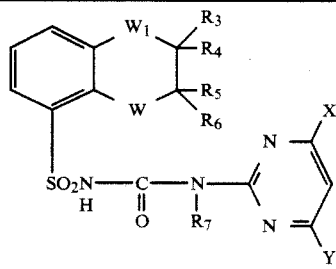

| $W_1$ | W | $R_3$ | $R_4$ | $R_5$ | $R_6$ | $R_7$ | X | Y | m.p.(°C.) |
|---|---|---|---|---|---|---|---|---|---|
| O | O | H | H | H | H | H | CH₃ | CH₃ | |
| O | O | H | H | H | H | H | CH₃ | OCH₃ | 203–205° |
| O | O | H | H | H | H | H | CH₃ | SCH₃ | |
| O | O | H | H | H | H | H | CH₃ | NH₂ | |
| O | O | H | H | H | H | H | OCH₃ | OCH₃ | |
| O | O | H | H | H | H | H | OCH₃ | CH₂OCH₃ | |
| O | O | H | H | H | H | H | OCH₃ | CH(OCH₃)₂ | |
| O | O | H | H | H | H | H | Cl | OCH₃ | |
| O | O | H | H | H | H | H | Cl | NH₂ | |
| O | O | H | H | H | H | H | Cl | NH(CH₃) | |
| O | O | H | H | H | H | H | Cl | N(CH₃)₂ | |
| O | O | H | H | H | H | CH₃ | CH₃ | CH₃ | |
| O | O | H | H | H | H | CH₃ | CH₃ | OCH₃ | |
| O | O | CH₃ | H | H | H | H | CH₃ | CH₃ | |
| O | O | CH₃ | H | H | H | H | CH₃ | OCH₃ | |
| O | O | CH₃ | H | H | H | H | OCH₃ | OCH₃ | |
| O | O | CH₃ | H | H | H | H | OCH₃ | CH₂(OCH₃) | |
| O | O | CH₃ | H | H | H | H | Cl | N(CH₃)₂ | |
| O | O | CH₃ | H | CH₃ | H | H | CH₃ | CH₃ | |
| O | O | CH₃ | H | CH₃ | H | H | CH₃ | OC₂H₅ | |
| O | O | CH₃ | H | CH₃ | H | H | CH₃ | CH₃(OCH₃) | |
| O | O | CH₃ | H | CH₃ | H | H | OCH₃ | OCH₃ | |
| O | O | CH₃ | CH₃ | H | H | H | CH₃ | CH₃ | |
| O | O | CH₃ | CH₃ | H | H | H | CH₃ | OCH₃ | |
| O | O | CH₃ | CH₃ | H | H | H | OCH₃ | OC₂H₅ | |
| O | O | CH₃ | CH₃ | H | H | H | Cl | N(CH₃)₂ | |
| O | O | CH₃ | CH₃ | CH₃ | H | H | CH₃ | CH₃ | |
| O | O | CH₃ | CH₃ | CH₃ | H | H | OCH₃ | SCH₃ | |
| O | O | CH₃ | CH₃ | CH₃ | CH₃ | H | OCH₃ | OCH₃ | |
| O | O | CH₃ | CH₃ | CH₃ | CH₃ | H | CH₃ | CH(OCH₃)₂ | |

TABLE IIa-continued

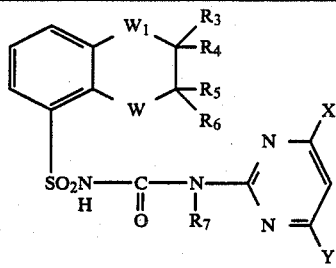

| W₁ | W | R₃ | R₄ | R₅ | R₆ | R₇ | X | Y | m.p.(°C.) |
|---|---|---|---|---|---|---|---|---|---|
| O | O | CH₃ | CH₃ | CH₃ | CH₃ | H | H | -CH(O-CH₂-CH₂-O) | |
| O | O | CH₃ | CH₃ | CH₃ | CH₃ | H | OCH₃ | SCH₃ | |
| O | O | CH₃ | CH₃ | CH₃ | CH₃ | CH₃ | CH₃ | CH₃ | |
| O | O | CH₃ | CH₃ | CH₃ | CH₃ | CH₃ | CH₃ | OCH₃ | |
| O | O | CH₃ | CH₃ | CH₃ | CH₃ | CH₃ | OCH₃ | OCH₃ | |
| S | S | H | H | H | H | H | CH₃ | CH₃ | |
| S | S | H | H | H | H | H | CH₃ | OCH₃ | |
| S | S | H | H | H | H | H | CH₃ | N(CH₃)₂ | |
| S | S | H | H | H | H | H | OCH₃ | H | |
| S | S | H | H | H | H | H | OCH₃ | OCH₃ | |
| S | S | H | H | H | H | H | OCH₃ | CH₃(OCH₃)₂ | |
| S | S | H | H | H | H | H | Cl | OCH₃ | |
| S | S | H | H | H | H | H | Cl | NH₂ | |
| S | S | H | H | H | H | H | Cl | N(CH₃)₂ | |
| S | S | H | H | H | H | CH₃ | CH₃ | OCH₃ | |
| S | S | H | H | H | H | CH₃ | OCH₃ | OCH₃ | |
| S | S | CH₃ | H | H | H | H | CH₃ | -CH(O-CH₂-CH₂-O) | |
| S | S | CH₃ | H | H | H | H | CH₃ | OCH₃ | |
| S | S | CH₃ | H | H | H | H | OCH₃ | OCH₃ | |
| S | S | CH₃ | H | H | H | H | Cl | OCH₃ | |
| S | S | CH₃ | H | H | H | H | Cl | N(CH₃)₂ | |
| S | S | CH₃ | H | CH₃ | H | H | CH₃ | CH₃ | |
| S | S | CH₃ | H | CH₃ | H | H | CH₃ | OCH₃ | |
| S | S | CH₃ | H | CH₃ | H | H | CH₃ | OCH₃ | |
| S | S | CH₃ | H | CH₃ | H | H | OCH₃ | -CH(O-CH₂-CH₂-O) | |
| S | S | CH₃ | CH₃ | H | H | H | CH₃ | CH₃ | |
| S | S | CH₃ | CH₃ | H | H | H | CH₃ | OCH₃ | |
| S | S | CH₃ | CH₃ | H | H | H | OCH₃ | OCH₃ | |
| S | S | CH₃ | CH₃ | H | H | H | OCH₃ | N(CH₃)₂ | |
| S | S | CH₃ | CH₃ | CH₃ | H | H | CH₃ | CH₃ | |
| S | S | CH₃ | CH₃ | CH₃ | H | H | OCH₃ | NH₂ | |
| S | S | CH₃ | CH₃ | CH₃ | CH₃ | H | OCH₃ | OCH₃ | |
| S | S | CH₃ | CH₃ | CH₃ | CH₃ | H | CH₃ | CH(OCH₃)₂ | |
| S | S | CH₃ | CH₃ | CH₃ | CH₃ | H | CH₃ | -CH(O-CH₂-CH₂-O) | |
| S | S | CH₃ | CH₃ | CH₃ | CH₃ | H | OCH₃ | SCH₃ | |
| S | S | CH₃ | CH₃ | CH₃ | CH₃ | CH₃ | CH₃ | CH₃ | |
| S | S | CH₃ | CH₃ | CH₃ | CH₃ | CH₃ | CH₃ | OCH₃ | |
| SO₂ | SO₂ | H | H | H | H | H | CH₃ | CH₃ | |
| SO₂ | SO₂ | H | H | H | H | H | CH₃ | NHCH₃ | |
| SO₂ | SO₂ | H | H | H | H | H | CH₃ | OCH₃ | |
| SO₂ | SO₂ | H | H | H | H | H | CH₃ | SCH₃ | |
| SO₂ | SO₂ | H | H | H | H | H | OCH₃ | H | |
| SO₂ | SO₂ | H | H | H | H | H | OCH₃ | OCH₃ | |

TABLE IIa-continued

| W₁ | W | R₃ | R₄ | R₅ | R₆ | R₇ | X | Y | m.p.(°C.) |
|---|---|---|---|---|---|---|---|---|---|
| SO₂ | SO₂ | H | H | H | H | H | OCH₃ | CH₂(OCH₃)₂ | |
| SO₂ | SO₂ | H | H | H | H | H | OCH₃ | NH(CH₃)₂ | |
| SO₂ | SO₂ | H | H | H | H | H | Cl | OCH₃ | |
| SO₂ | SO₂ | H | H | H | H | H | Cl | NH₂ | |
| SO₂ | SO₂ | H | H | H | H | H | Cl | N(CH₃)₂ | |
| SO₂ | SO₂ | H | H | H | H | CH₃ | CH₃ | OCH₃ | |
| SO₂ | SO₂ | H | H | H | H | CH₃ | OCH₃ | OCH₃ | |
| SO₂ | SO₂ | CH₃ | H | H | H | H | CH₃ | CH₃ | |
| SO₂ | SO₂ | CH₃ | H | H | H | H | CH₃ | OCH₃ | |
| SO₂ | SO₂ | CH₃ | H | H | H | H | OCH₃ | OCH₃ | |
| SO₂ | SO₂ | CH₃ | H | H | H | H | Cl | OCH₃ | |
| SO₂ | SO₂ | CH₃ | H | H | H | H | Cl | N(CH₃)₂ | |
| SO₂ | SO₂ | CH₃ | H | CH₃ | H | H | CH₃ | CH₃ | |
| SO₂ | SO₂ | CH₃ | H | CH₃ | H | H | CH₃ | OCH₃ | |
| SO₂ | SO₂ | CH₃ | H | CH₃ | H | H | OCH₃ | OCH₃ | |
| SO₂ | SO₂ | CH₃ | CH₃ | H | H | H | CH₃ | CH₃ | |
| SO₂ | SO₂ | CH₃ | CH₃ | H | H | H | CH₃ | NH(CH₃) | |
| SO₂ | SO₂ | CH₃ | CH₃ | H | H | H | OCH₃ | OCH₃ | |
| SO₂ | SO₂ | CH₃ | CH₃ | H | H | H | OCH₃ | N(CH₃)₂ | |
| SO₂ | SO₂ | CH₃ | CH₃ | CH₃ | H | H | CH₃ | CH₃ | |
| SO₂ | SO₂ | CH₃ | CH₃ | CH₃ | H | H | OCH₃ | OCH₃ | |
| SO₂ | SO₂ | CH₃ | CH₃ | CH₃ | CH₃ | H | OCH₃ | OCH₃ | |
| SO₂ | SO₂ | CH₃ | CH₃ | CH₃ | CH₃ | H | CH₃ | CH(OCH₃)₂ | |
| SO₂ | SO₂ | CH₃ | CH | CH₃ | CH₃ | H | CH₃ | -CH(OCH₂CH₂O) cyclic | |
| SO₂ | SO₂ | CH₃ | CH₃ | CH₃ | CH₃ | H | OCH₃ | SCH₃ | |
| SO₂ | SO₂ | CH₃ | CH₃ | CH₃ | CH₃ | CH₃ | CH₃ | CH₃ | |
| SO₂ | SO₂ | CH₃ | CH₃ | CH₃ | CH₃ | CH₃ | CH₃ | OCH₃ | |
| SO | SO | H | H | H | H | H | CH₃ | CH₃ | |
| SO | SO | H | H | H | H | H | OCH₃ | OCH₃ | |
| SO | SO | H | H | H | H | H | OCH₃ | SCH₃ | |
| SO | SO | H | H | H | H | H | CH₃ | N(CH₃)₂ | |
| SO | SO | CH₃ | H | H | H | H | CH₃ | OCH₃ | |
| SO | SO | CH₃ | CH₃ | CH₃ | CH₃ | H | CH₃ | OCH₃ | |
| O | S | H | H | H | H | H | CH₃ | OCH₃ | |
| O | S | CH₃ | CH₃ | CH₃ | CH₃ | H | CH₃ | CH₃ | |
| O | SO | H | H | H | H | H | CH₃ | OCH₃ | |
| O | SO₂ | H | H | H | H | H | CH₃ | OCH₃ | |
| O | SO₂ | CH₃ | H | CH₃ | H | H | CH₃ | OCH₃ | |
| S | O | H | H | H | H | H | CH₃ | OCH₃ | |
| SO | O | H | H | H | H | H | CH₃ | OCH₃ | |
| SO₂ | O | H | H | H | H | H | CH₃ | OCH₃ | |
| SO₂ | S | H | H | H | H | H | CH₃ | OCH₃ | |
| SO₂ | S | H | H | H | H | H | CH₃ | OCH₃ | |
| S | SO | H | H | H | H | H | CH₃ | OCH₃ | |
| S | SO₂ | H | H | H | H | H | CH₃ | OCH₃ | |
| S | SO₂ | CH₃ | H | CH₃ | H | H | CH₃ | OCH₃ | |
| SO₂ | SO | H | H | H | H | H | CH₃ | OCH₃ | |
| SO | SO₂ | H | H | H | H | H | CH₃ | OCH₃ | |

TABLE IIb

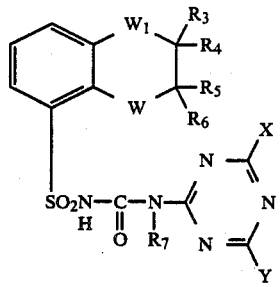

| W1 | W | R3 | R4 | R5 | R6 | R7 | X | Y | m.p. (°C.) |
|---|---|---|---|---|---|---|---|---|---|
| O | O | H | H | H | H | H | CH3 | CH3 | |
| O | O | H | H | H | H | H | CH3 | OCH3 | |
| O | O | H | H | H | H | H | CH3 | OC2H5 | |
| O | O | H | H | H | H | H | CH3 | N(CH3)2 | |
| O | O | H | H | H | H | H | CH3 | CH2OCH3 | |
| O | O | H | H | H | H | H | CH3 | SCH3 | |
| O | O | H | H | H | H | H | OCH3 | SCH3 | |
| O | O | H | H | H | H | H | OCH3 | OCH3 | |
| O | O | H | H | H | H | H | OCH3 | OC2H5 | |
| O | O | H | H | H | H | H | OCH3 | CH2OCH3 | |
| O | O | H | H | H | H | H | OCH3 | NH2 | |
| O | O | H | H | H | H | H | OCH3 | NHCH3 | |
| O | O | H | H | H | H | H | OCH3 | N(CH3)2 | |
| O | O | H | H | H | H | CH3 | CH3 | OCH3 | |
| O | O | H | H | H | H | CH3 | OCH3 | OCH3 | |
| O | O | CH3 | H | H | H | H | CH3 | CH3 | |
| O | O | CH3 | H | H | H | H | CH3 | OCH3 | |
| O | O | CH3 | H | H | H | H | CH3 | CH(OCH3)2 | |
| O | O | CH3 | H | H | H | H | CH3 | CH2OCH3 | |
| O | O | CH3 | H | H | H | H | OCH3 | OCH3 | |
| O | O | CH3 | H | H | H | H | OCH3 | —CH(OCH2CH2O) | |
| O | O | CH3 | H | H | H | H | OCH3 | CH2OCH3 | |
| O | O | CH3 | H | H | H | H | OCH3 | SCH3 | |
| O | O | CH3 | H | CH3 | H | H | CH3 | OCH3 | |
| O | O | CH3 | H | CH3 | H | H | CH3 | OC2H5 | |
| O | O | CH3 | H | CH3 | H | H | OCH3 | H | |
| O | O | CH3 | H | CH3 | H | H | OCH3 | OCH3 | |
| O | O | CH3 | CH3 | H | H | H | CH3 | CH3 | |
| O | O | CH3 | CH3 | H | H | H | CH3 | OCH3 | |
| O | O | CH3 | CH3 | H | H | H | OCH3 | OCH3 | |
| O | O | CH3 | CH3 | CH3 | H | H | CH3 | CH3 | |
| O | O | CH3 | CH3 | CH3 | H | H | CH3 | OCH3 | |
| O | O | CH3 | CH3 | CH3 | H | H | OCH3 | OCH3 | |
| O | O | CH3 | CH3 | CH3 | CH3 | H | CH3 | N(CH3)2 | |
| O | O | CH3 | CH3 | CH3 | CH3 | H | CH3 | —CH(OCH2CH2O) | |
| O | O | CH3 | CH3 | CH3 | CH3 | H | OCH3 | OCH3 | |
| O | O | CH3 | CH3 | CH3 | CH3 | H | OCH3 | SCH3 | |
| O | O | CH3 | CH3 | CH3 | CH3 | H | OCH3 | N(CH3)2 | |
| O | O | CH3 | CH3 | CH3 | CH3 | CH3 | CH3 | CH3 | |
| O | O | CH3 | CH3 | CH3 | CH3 | CH3 | CH3 | OCH3 | |
| S | S | H | H | H | H | H | CH3 | CH3 | |
| S | S | H | H | H | H | H | CH3 | OCH3 | |
| S | S | H | H | H | H | H | CH3 | OC2H5 | |
| S | S | H | H | H | H | H | CH3 | CH2OCH3 | |
| S | S | H | H | H | H | H | OCH3 | H | |
| S | S | H | H | H | H | H | OCH3 | OCH3 | |
| S | S | H | H | H | H | H | OCH3 | OC2H5 | |
| S | S | H | H | H | H | H | OCH3 | CH2OCH3 | |
| S | S | H | H | H | H | H | OCH3 | SCH3 | |
| S | S | H | H | H | H | CH3 | CH3 | CH3 | |
| S | S | H | H | H | H | CH3 | CH3 | OCH3 | |
| S | S | CH3 | H | H | H | H | CH3 | CH3 | |

TABLE IIb-continued

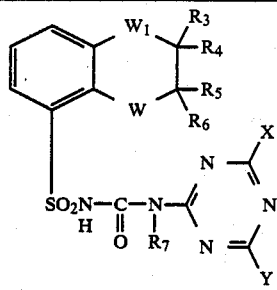

| W1 | W | R3 | R4 | R5 | R6 | R7 | X | Y | m.p. (°C.) |
|---|---|---|---|---|---|---|---|---|---|
| S | S | CH3 | H | H | H | H | CH3 | OCH3 | |
| S | S | CH3 | H | H | H | H | CH3 | OC2H5 | |
| S | S | CH3 | H | H | H | H | CH3 | CH2OCH3 | |
| S | S | CH3 | H | H | H | H | OCH3 | OCH3 | |
| S | S | CH3 | H | H | H | H | OCH3 | OC2H5 | |
| S | S | CH3 | H | H | H | H | OCH3 | CH2OCH3 | |
| S | S | CH3 | H | CH3 | H | H | CH3 | OC2H5 | |
| S | S | CH3 | H | CH3 | H | H | OCH3 | H | |
| S | S | CH3 | H | CH3 | H | H | OCH3 | OCH3 | |
| S | S | CH3 | CH3 | H | H | H | CH3 | CH3 | |
| S | S | CH3 | CH3 | H | H | H | CH3 | OCH3 | |
| S | S | CH3 | CH3 | H | H | H | OCH3 | OCH3 | |
| S | S | CH3 | CH3 | CH3 | H | H | CH3 | CH3 | |
| S | S | CH3 | CH3 | CH3 | H | H | CH3 | OCH3 | |
| S | S | CH3 | CH3 | CH3 | H | H | OCH3 | OCH3 | |
| S | S | CH3 | CH3 | CH3 | CH3 | H | CH3 | OCH3 | |
| S | S | CH3 | CH3 | CH3 | CH3 | H | CH3 | NH2 | |
| S | S | CH3 | CH3 | CH3 | CH3 | H | CH3 | NHCH3 | |
| S | S | CH3 | CH3 | CH3 | CH3 | H | CH3 | N(CH3)2 | |
| S | S | CH3 | CH3 | CH3 | CH3 | H | OCH3 | OCH3 | |
| S | S | CH3 | CH3 | CH3 | CH3 | H | OCH3 | SCH3 | |
| S | S | CH3 | CH3 | CH3 | CH3 | CH3 | CH3 | CH3 | |
| S | S | CH3 | CH3 | CH3 | CH3 | CH3 | OCH3 | OCH3 | |
| SO2 | SO2 | H | H | H | H | H | CH3 | CH3 | |
| SO2 | SO2 | H | H | H | H | H | CH3 | OCH3 | |
| SO2 | SO2 | H | H | H | H | H | CH3 | OC2H5 | |
| SO2 | SO2 | H | H | H | H | H | CH3 | CH2OCH3 | |
| SO2 | SO2 | H | H | H | H | H | CH3 | N(CH3)2 | |
| SO2 | SO2 | H | H | H | H | H | OCH3 | OCH3 | |
| SO2 | SO2 | H | H | H | H | H | OCH3 | OC2H5 | |
| SO2 | SO2 | H | H | H | H | H | OCH3 | CH2OCH3 | |
| SO2 | SO2 | H | H | H | H | CH3 | CH3 | OCH3 | |
| SO2 | SO2 | H | H | H | H | CH3 | OCH3 | OCH3 | |
| SO2 | SO2 | CH3 | H | H | H | H | CH3 | CH3 | |
| SO2 | SO2 | CH3 | H | H | H | H | CH3 | OCH3 | |
| SO2 | SO2 | CH3 | H | H | H | H | CH3 | OC2H5 | |
| SO2 | SO2 | CH3 | H | H | H | H | CH3 | CH2OCH3 | |
| SO2 | SO2 | CH3 | H | H | H | H | OCH3 | OCH3 | |
| SO2 | SO2 | CH3 | H | H | H | H | OCH3 | OC2H5 | |
| SO2 | SO2 | CH3 | H | H | H | H | OCH3 | CH2OCH3 | |
| SO2 | SO2 | CH3 | H | CH3 | H | H | CH3 | OCH3 | |
| SO2 | SO2 | CH3 | H | CH3 | H | H | CH3 | OC2H5 | |
| SO2 | SO2 | CH3 | H | CH3 | H | H | OCH3 | H | |
| SO2 | SO2 | CH3 | H | CH3 | H | H | OCH3 | OCH3 | |
| SO2 | SO2 | CH3 | CH3 | H | H | H | CH3 | CH3 | |
| SO2 | SO2 | CH3 | CH3 | H | H | H | CH3 | OCH3 | |
| SO2 | SO2 | CH3 | CH3 | H | H | H | OCH3 | OCH3 | |
| SO2 | SO2 | CH3 | CH3 | CH3 | H | H | CH3 | CH3 | |
| SO2 | SO2 | CH3 | CH3 | CH3 | H | H | CH3 | OCH3 | |
| SO2 | SO2 | CH3 | CH3 | CH3 | H | H | OCH3 | OCH3 | |
| SO2 | SO2 | CH3 | CH3 | CH3 | CH3 | H | OCH3 | OCH3 | |
| SO2 | SO2 | CH3 | CH3 | CH3 | CH3 | H | OCH3 | NHCH3 | |
| SO2 | SO2 | CH3 | CH3 | CH3 | CH3 | CH3 | OCH3 | OCH3 | |
| SO | SO | H | H | H | H | H | CH3 | CH3 | |
| SO | SO | H | H | H | H | H | CH3 | SCH3 | |
| SO | SO | H | H | H | H | H | OCH3 | OCH3 | |
| SO | SO | CH3 | CH3 | CH3 | H | H | CH3 | OCH3 | |
| SO | SO | CH3 | CH3 | CH3 | CH3 | H | CH3 | OCH3 | |
| O | S | H | H | H | H | H | CH3 | OCH3 | |
| O | S | CH3 | CH3 | CH3 | CH3 | H | OCH3 | SCH3 | |
| O | SO | H | H | H | H | H | CH3 | OCH3 | |
| O | SO2 | H | H | H | H | H | CH3 | OCH3 | |

TABLE IIb-continued

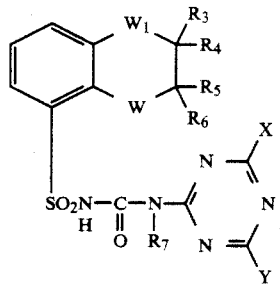

| W₁ | W | R₃ | R₄ | R₅ | R₆ | R₇ | X | Y | m.p. (°C.) |
|---|---|---|---|---|---|---|---|---|---|
| O | SO₂ | CH₃ | H | CH₃ | H | H | CH₃ | OCH₃ | |
| S | O | H | H | H | H | H | CH₃ | OCH₃ | |
| SO | O | H | H | H | H | H | CH₃ | OCH₃ | |
| SO₂ | O | H | H | H | H | H | CH₃ | OCH₃ | |
| SO | S | H | H | H | H | H | CH₃ | OCH₃ | |
| SO₂ | S | H | H | H | H | H | CH₃ | OCH₃ | |
| S | SO | H | H | H | H | H | CH₃ | OCH₃ | |
| S | SO₂ | H | H | H | H | H | CH₃ | OCH₃ | |
| S | SO₂ | CH₃ | H | CH₃ | H | H | CH₃ | OCH₃ | |
| SO₂ | SO | H | H | H | H | H | CH₃ | OCH₃ | |
| SO | SO₂ | H | H | H | H | H | CH₃ | OCH₃ | |

TABLE IIc

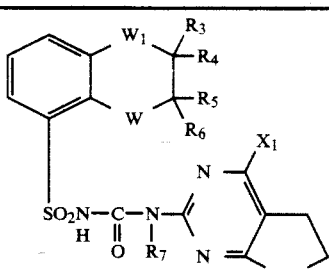

| W₁ | W | R₃ | R₄ | R₅ | R₆ | R₇ | G | X₁ |
|---|---|---|---|---|---|---|---|---|
| O | O | H | H | H | H | H | CH₂ | CH₃ |
| O | O | H | H | H | H | H | CH₂ | OCH₃ |
| O | O | H | H | H | H | H | O | CH₃ |
| O | O | H | H | H | H | H | O | OCH₃ |
| O | O | H | H | H | H | CH₃ | CH₂ | CH₃ |
| O | O | H | H | H | H | CH₃ | O | OCH₃ |
| O | O | CH₃ | H | H | H | H | O | CH₃ |
| O | O | CH₃ | H | H | H | H | CH₂ | OCH₃ |
| O | O | CH₃ | H | CH₃ | H | H | O | CH₃ |
| O | O | CH₃ | H | CH₃ | H | O | O | OCH₃ |
| O | O | CH₃ | CH₃ | CH₃ | H | H | O | OCH₃ |
| O | O | CH₃ | CH₃ | CH₃ | H | H | CH₂ | CH₃ |
| O | O | CH₃ | CH₃ | CH₃ | CH₃ | H | O | CH₃ |
| O | O | CH₃ | CH₃ | CH₃ | CH₃ | H | O | OCH₃ |
| O | O | CH₃ | CH₃ | CH₃ | CH₃ | CH₃ | CH₂ | CH₃ |
| O | O | CH₃ | CH₃ | CH₃ | CH₃ | CH₃ | O | OCH₃ |
| S | S | H | H | H | H | H | CH₂ | CH₃ |
| S | S | H | H | H | H | H | CH₂ | OCH₃ |
| S | S | H | H | H | H | H | O | CH₃ |
| S | S | H | H | H | H | H | O | OCH₃ |
| S | S | H | H | H | H | CH₃ | CH₂ | CH₃ |
| S | S | H | H | H | H | CH₃ | O | OCH₃ |
| S | S | CH₃ | H | H | H | H | O | CH₃ |
| S | S | CH₃ | H | CH₃ | H | H | CH₂ | CH₃ |
| S | S | CH₃ | H | CH₃ | H | H | O | CH₃ |
| S | S | CH₃ | H | CH₃ | H | O | O | OCH₃ |
| S | S | CH₃ | CH₃ | CH₃ | H | H | O | OCH₃ |
| S | S | CH₃ | CH₃ | CH₃ | CH₃ | H | CH₂ | CH₃ |
| S | S | CH₃ | CH₃ | CH₃ | CH₃ | H | O | OCH₃ |
| S | S | CH₃ | CH₃ | CH₃ | CH₃ | CH₃ | CH₂ | CH₃ |
| S | S | CH₃ | CH₃ | CH₃ | CH₃ | CH₃ | O | OCH₃ |
| SO₂ | SO₂ | H | H | H | H | H | CH₂ | CH₃ |
| SO₂ | SO₂ | H | H | H | H | H | CH₂ | OCH₃ |
| SO₂ | SO₂ | H | H | H | H | H | O | CH₃ |

TABLE IIc-continued

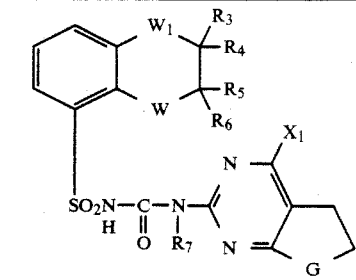

| W₁ | W | R₃ | R₄ | R₅ | R₆ | R₇ | G | X₁ |
|---|---|---|---|---|---|---|---|---|
| SO₂ | SO₂ | H | H | H | H | H | O | OCH₃ |
| SO₂ | SO₂ | H | H | H | H | CH₃ | CH₂ | CH₃ |
| SO₂ | SO₂ | H | H | H | H | CH₃ | O | CH₃ |
| SO₂ | SO₂ | H | H | H | H | CH₃ | O | OCH₃ |
| SO₂ | SO₂ | CH₃ | H | H | H | H | O | CH₃ |
| SO₂ | SO₂ | CH₃ | H | CH₃ | H | H | CH₂ | OCH₃ |
| SO₂ | SO₂ | CH₃ | H | CH₃ | H | H | O | CH₃ |
| SO₂ | SO₂ | CH₃ | H | CH₃ | H | O | O | OCH₃ |
| SO₂ | SO₂ | CH₃ | CH₃ | CH₃ | H | H | O | OCH₃ |
| SO₂ | SO₂ | CH₃ | CH₃ | CH₃ | CH₃ | H | CH₂ | CH₃ |
| SO₂ | SO₂ | CH₃ | CH₃ | CH₃ | CH₃ | H | O | CH₃ |
| SO₂ | SO₂ | CH₃ | CH₃ | CH₃ | CH₃ | H | O | OCH₃ |
| SO₂ | SO₂ | CH₃ | CH₃ | CH₃ | CH₃ | CH₃ | CH₂ | CH₃ |
| SO₂ | SO₂ | CH₃ | CH₃ | CH₃ | CH₃ | CH₃ | O | OCH₃ |
| SO | SO | H | H | H | H | H | CH₂ | CH₃ |
| SO | SO | H | H | H | H | H | O | OCH₃ |
| SO | SO | H | H | H | H | H | O | CH₃ |
| SO | SO | CH₃ | H | H | H | H | O | CH₃ |
| SO | SO | CH₃ | CH₃ | CH₃ | CH₃ | H | O | CH₃ |
| O | S | H | H | H | H | H | O | CH₃ |
| O | SO | H | H | H | H | H | O | CH₃ |
| O | SO₂ | H | H | H | H | H | O | CH₃ |
| O | SO₂ | CH₃ | H | H | H | H | O | CH₃ |
| O | SO₂ | CH₃ | CH₃ | CH₃ | CH₃ | H | O | CH₃ |
| S | O | H | H | H | H | H | O | CH₃ |
| SO | O | H | H | H | H | H | O | CH₃ |
| SO₂ | O | H | H | H | H | H | O | CH₃ |
| SO | S | H | H | H | H | H | O | CH₃ |
| SO₂ | S | H | H | H | H | H | O | CH₃ |
| S | SO | H | H | H | H | H | O | CH₃ |
| S | SO₂ | H | H | H | H | H | O | CH₃ |
| S | SO₂ | CH₃ | H | CH₃ | H | H | O | CH₃ |
| SO₂ | SO | H | H | H | H | H | O | CH₃ |
| SO | SO₂ | H | H | H | H | H | O | CH₃ |

TABLE IId

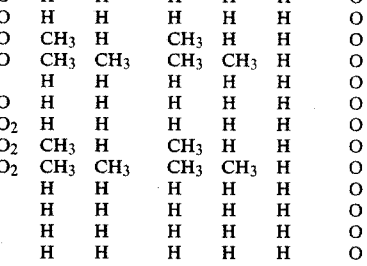

| W₁ | W | R₃ | R₄ | R₅ | R₆ | R₇ | X₁ |
|---|---|---|---|---|---|---|---|
| O | O | H | H | H | H | H | CH₃ |
| O | O | H | H | H | H | H | OCH₃ |
| O | O | H | H | H | H | CH₃ | CH₃ |
| O | O | H | H | H | H | CH₃ | OCH₃ |
| O | O | CH₃ | H | H | H | H | CH₃ |
| O | O | CH₃ | H | H | H | H | OCH₃ |
| O | O | CH₃ | H | CH₃ | H | H | OCH₃ |
| O | O | CH₃ | H | CH₃ | H | H | CH₃ |
| O | O | CH₃ | CH₃ | H | H | H | CH₃ |
| O | O | CH₃ | CH₃ | CH₃ | H | H | CH₃ |
| O | O | CH₃ | CH₃ | CH₃ | CH₃ | H | CH₃ |
| O | O | CH₃ | CH₃ | CH₃ | CH₃ | H | OCH₃ |
| O | O | CH₃ | CH₃ | CH₃ | CH₃ | CH₃ | CH₃ |

TABLE IId-continued

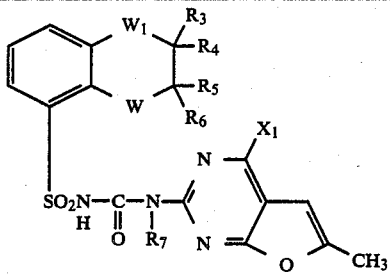

| W₁ | W | R₃ | R₄ | R₅ | R₆ | R₇ | X₁ |
|---|---|---|---|---|---|---|---|
| O | O | CH₃ | CH₃ | CH₃ | CH₃ | CH₃ | OCH₃ |
| S | S | H | H | H | H | H | CH₃ |
| S | S | CH₃ | H | CH₃ | H | H | CH₃ |
| S | S | CH₃ | H | CH₃ | H | H | OCH₃ |
| S | S | CH₃ | CH₃ | CH₃ | CH₃ | H | CH₃ |
| S | S | CH₃ | CH₃ | CH₃ | CH₃ | H | OCH₃ |
| S | S | CH₃ | CH₃ | CH₃ | CH₃ | CH₃ | CH₃ |
| S | S | CH₃ | CH₃ | CH₃ | CH₃ | CH₃ | OCH₃ |
| SO₂ | SO₂ | H | H | H | H | H | CH₃ |
| SO₂ | SO₂ | H | H | H | H | H | OCH₃ |
| SO₂ | SO₂ | CH₃ | H | CH₃ | H | H | CH₃ |
| SO₂ | SO₂ | CH₃ | H | CH₃ | H | H | OCH₃ |
| SO₂ | SO₂ | CH₃ | CH₃ | CH₃ | CH₃ | H | OCH₃ |
| SO | SO | H | H | H | H | H | CH₃ |
| SO | SO | H | H | H | H | H | OCH₃ |
| SO | SO | CH₃ | H | CH₃ | H | H | CH₃ |
| SO | SO | CH₃ | H | CH₃ | H | H | OCH₃ |
| O | S | H | H | H | H | H | OCH₃ |
| O | SO | H | H | H | H | H | OCH₃ |
| O | SO₂ | H | H | H | H | H | OCH₃ |
| O | SO₂ | H | CH₃ | H | CH₃ | H | CH₃ |
| O | SO₂ | H | CH₃ | H | CH₃ | H | OCH₃ |
| O | SO₂ | CH₃ | CH₃ | CH₃ | CH₃ | H | OCH₃ |
| S | O | H | H | H | H | H | CH₃ |
| SO | O | H | H | H | H | H | CH₃ |
| SO₂ | O | H | H | H | H | H | CH₃ |
| SO | S | H | H | H | H | H | CH₃ |
| SO₂ | S | H | H | H | H | H | CH₃ |
| S | SO | H | H | H | H | H | CH₃ |
| S | SO₂ | H | H | H | H | H | CH₃ |
| S | SO₂ | CH₃ | H | CH₃ | H | H | CH₃ |
| S | SO₂ | CH₃ | CH₃ | CH₃ | H | H | CH₃ |
| SO₂ | SO | H | H | H | H | H | CH₃ |
| SO | SO₂ | H | H | H | H | H | CH₃ |

TABLE IIe

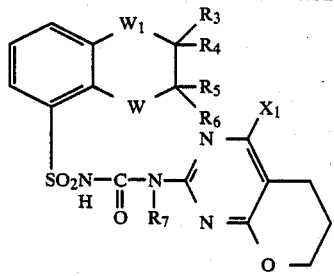

| W₁ | W | R₃ | R₄ | R₅ | R₆ | R₇ | X₁ |
|---|---|---|---|---|---|---|---|
| O | O | H | H | H | H | H | CH₃ |
| O | O | H | H | H | H | H | OCH₃ |
| O | O | H | H | H | H | CH₃ | CH₃ |
| O | O | H | H | H | H | CH₃ | OCH₃ |
| O | O | CH₃ | H | H | H | H | CH₃ |
| O | O | CH₃ | H | H | H | H | OCH₃ |
| O | O | CH₃ | H | CH₃ | H | H | CH₃ |
| O | O | CH₃ | H | CH₃ | H | H | OCH₃ |
| O | O | CH₃ | CH₃ | H | H | H | CH₃ |
| O | O | CH₃ | CH₃ | H | H | H | OCH₃ |
| O | O | CH₃ | CH₃ | CH₃ | H | H | CH₃ |
| O | O | CH₃ | CH₃ | CH₃ | H | H | OCH₃ |
| O | O | CH₃ | CH₃ | CH₃ | CH₃ | H | CH₃ |
| O | O | CH₃ | CH₃ | CH₃ | CH₃ | H | OCH₃ |
| O | O | CH₃ | CH₃ | CH₃ | CH₃ | CH₃ | CH₃ |
| O | O | CH₃ | CH₃ | CH₃ | CH₃ | CH₃ | OCH₃ |

TABLE IIe-continued

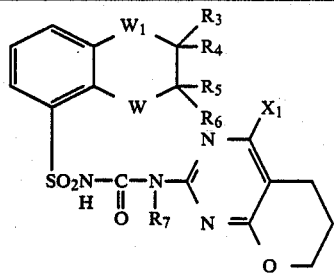

| W₁ | W | R₃ | R₄ | R₅ | R₆ | R₇ | X₁ |
|---|---|---|---|---|---|---|---|
| S | S | H | H | H | H | H | CH₃ |
| S | S | H | H | H | H | H | OCH₃ |
| S | S | CH₃ | H | CH₃ | H | H | CH₃ |
| S | S | CH₃ | H | CH₃ | H | H | OCH₃ |
| S | S | CH₃ | CH₃ | CH₃ | CH₃ | H | CH₃ |
| S | S | CH₃ | CH₃ | CH₃ | CH₃ | H | OCH₃ |
| S | S | CH₃ | CH₃ | CH₃ | CH₃ | CH₃ | CH₃ |
| SO₂ | SO₂ | H | H | H | H | H | CH₃ |
| SO₂ | SO₂ | H | H | H | H | H | OCH₃ |
| SO₂ | SO₂ | H | H | H | H | CH₃ | OCH₃ |
| SO₂ | SO₂ | CH₃ | H | CH₃ | H | H | CH₃ |
| SO₂ | SO₂ | CH₃ | H | CH₃ | H | H | OCH₃ |
| SO₂ | SO₂ | CH₃ | CH₃ | CH₃ | CH₃ | H | CH₃ |
| SO₂ | SO₂ | CH₃ | CH₃ | CH₃ | CH₃ | H | OCH₃ |
| SO₂ | SO₂ | CH₃ | CH₃ | CH₃ | CH₃ | CH₃ | CH₃ |
| SO₂ | SO₂ | CH₃ | CH₃ | CH₃ | CH₃ | CH₃ | OCH₃ |
| SO | SO | H | H | H | H | H | CH₃ |
| SO | SO | H | H | H | H | H | OCH₃ |
| SO | SO | CH₃ | H | CH₃ | H | H | CH₃ |
| SO | SO | CH₃ | H | CH₃ | H | H | OCH₃ |
| O | S | H | H | H | H | H | OCH₃ |
| O | SO | H | H | H | H | H | OCH₃ |
| O | SO₂ | H | H | H | H | H | OCH₃ |
| O | SO₂ | H | CH₃ | H | CH₃ | H | CH₃ |
| O | SO₂ | H | CH₃ | H | CH₃ | H | OCH₃ |
| O | SO₂ | CH₃ | CH₃ | CH₃ | CH₃ | H | OCH₃ |
| S | O | H | H | H | H | H | CH₃ |
| SO | O | H | H | H | H | H | CH₃ |
| SO₂ | O | H | H | H | H | H | CH₃ |
| SO | S | H | H | H | H | H | CH₃ |
| SO₂ | S | H | H | H | H | H | CH₃ |
| S | SO | H | H | H | H | H | CH₃ |
| S | SO₂ | H | H | H | H | H | CH₃ |
| S | SO₂ | CH₃ | H | CH₃ | H | H | CH₃ |
| S | SO₂ | CH₃ | CH₃ | H | CH₃ | H | CH₃ |
| SO₂ | SO | H | H | H | H | H | CH₃ |
| SO | SO₂ | H | H | H | H | H | CH₃ |

TABLE IIf

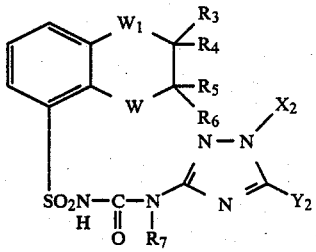

| W₁ | W | R₃ | R₄ | R₅ | R₆ | R₇ | X₂ | Y₂ |
|---|---|---|---|---|---|---|---|---|
| O | O | H | H | H | H | H | CH₃ | OCH₃ |
| O | O | H | H | H | H | H | CH₂CF₃ | SCH₃ |
| O | O | H | H | H | H | H | CH₂CF₃ | OCH₂CH₃ |
| O | O | H | H | H | H | CH₃ | CH₃ | OCH₃ |
| O | O | H | H | H | H | CH₃ | CH₃ | SCH₃ |
| O | O | CH₃ | H | H | H | H | C₂H₅ | OCH₃ |
| O | O | CH₃ | H | CH₃ | H | H | CH₃ | OC₂H₅ |
| O | O | CH₃ | H | CH₃ | H | H | CH₂CF₃ | SCH₃ |
| O | O | CH₃ | CH₃ | CH₃ | H | H | CH₃CH₂CH₂ | OCH₃ |
| O | O | CH₃ | CH₃ | CH₃ | CH₃ | H | CH₃ | OCH₃ |
| O | O | CH₃ | CH₃ | CH₃ | CH₃ | H | CH₃ | SCH₃ |
| O | O | CH₃ | CH₃ | CH₃ | CH₃ | H | CH₃CH₂CH₂ | SCH₃ |

TABLE IIf-continued

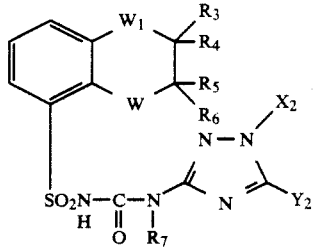

| W₁ | W | R₃ | R₄ | R₅ | R₆ | R₇ | X₂ | Y₂ |
|----|----|----|----|----|----|----|----|----|
| O | O | CH₃ | CH₃ | CH₃ | CH₃ | H | (CH₃)₂CH | SC₂H₅ |
| O | O | CH₃ | CH₃ | CH₃ | CH₃ | CH₃ | CH₃ | OCH₃ |
| S | S | H | H | H | H | H | CH₃ | OCH₃ |
| S | S | H | H | H | H | H | CH₃ | SCH₃ |
| S | S | H | H | H | H | CH₃ | CH₃ | OCH₃ |
| S | S | CH₃ | H | H | H | H | CH₃ | OCH₃ |
| S | S | CH₃ | H | CH₃ | H | H | CH₃ | OCH₃ |
| S | S | CH₃ | CH₃ | CH₃ | CH₃ | H | CH₃ | OCH₃ |
| SO₂ | SO₂ | H | H | H | H | H | CH₃ | OCH₃ |
| SO₂ | SO₂ | H | H | H | H | H | CH₃ | SCH₃ |
| SO₂ | SO₂ | H | H | H | H | H | CH₂CF₃ | OCH₃ |
| SO₂ | SO₂ | H | H | H | H | CH₃ | CH₃ | OCH₃ |
| SO₂ | SO₂ | CH₃ | CH₃ | CH₃ | CH₃ | H | CH₃ | OCH₃ |
| SO₂ | SO₂ | CH₃ | CH₃ | CH₃ | CH₃ | CH₃ | CH₃ | OCH₃ |
| SO | SO | H | H | H | H | H | CH₃ | OCH₃ |
| SO | SO | CH₃ | H | CH₃ | H | H | CH₃ | OCH₃ |
| SO | SO | CH₃ | CH₃ | CH₃ | CH₃ | H | CH₃ | OCH₃ |
| O | S | H | H | H | H | H | CH₃ | OCH₃ |
| O | SO | H | H | H | H | H | CH₃ | OCH₃ |
| O | SO₂ | H | H | H | H | H | CH₃ | OCH₃ |
| O | SO₂ | CH₃ | H | CH₃ | H | H | CH₃ | OCH₃ |
| O | SO₂ | CH₃ | CH₃ | CH₃ | CH₃ | H | CH₃ | OCH₃ |
| S | O | H | H | H | H | H | CH₃ | OCH₃ |
| SO | O | H | H | H | H | H | CH₃ | OCH₃ |
| SO₂ | O | H | H | H | H | H | CH₃ | OCH₃ |
| SO | S | H | H | H | H | H | CH₃ | OCH₃ |
| SO₂ | S | H | H | H | H | H | CH₃ | OCH₃ |
| S | SO | H | H | H | H | H | CH₃ | OCH₃ |
| S | SO₂ | H | H | H | H | H | CH₃ | OCH₃ |
| SO₂ | SO | H | H | H | H | H | CH₃ | OCH₃ |
| SO | SO₂ | H | H | H | H | H | CH₃ | OCH₃ |

Formulations

Useful formulations of the compounds of Formulae I and II can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE 12

| | Weight Percent* | | |
|---|---|---|---|
| | Active Ingredient | Diluent(s) | Surfactant(s) |
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |

TABLE 12-continued

| | Weight Percent* | | |
|---|---|---|---|
| | Active Ingredient | Diluent(s) | Surfactant(s) |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, N.Y., 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, March 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 21

Wettable Powder

| | |
|---|---|
| N—[(4,6-dimethylpyrimidin-2-yl)aminocarbonyl]-2,2-dimethyl-1,3-benzodioxole-4-sulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 22

Wettable Powder

| | |
|---|---|
| N—[(4-methoxy-6-methlpyrimidin-2-yl)aminocarbonyl]-2,2-dimethyl-1,3-benzodioxole-4-sulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 23

Granule

| | |
|---|---|
| Wettable Powder of Example 22 | 5% |
| attapulgite granules (U.S.S. 20–40 mesh; 0.84–0.42 mm) | 95% |

A slurry of wettable powder containing ≈25% solids is sprayed on the surface of attapulgite granules in a double-cone blender. The granules are dried and packaged.

EXAMPLE 24

Extruded Pellet

| | |
|---|---|
| N—[(4,6-dimethoxypyrimidin-2-yl)aminocarbonyl]-2,2-dimethyl-1,3-benzodioxole-4-sulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 25

Oil Suspension

| | |
|---|---|
| N—[(4-methoxy-6-methyl-1,3,5-triazin-2-yl)aminocarbonyl]-2,2-dimethyl-1,3-benzodioxole-4-sulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 26

Wettable Powder

| | |
|---|---|
| N—[(4,6-dimethoxy-1,3,5-triazin-2-yl)aminocarbonyl]-2,2-dimethyl-1,3-benzodioxole-4-sulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 27

Low Strength Granule

| | |
|---|---|
| N—[4,6-dimethyl-1,3,5-triazin-2-yl)aminocarbonyl]-1,4-benzodioxan-4-sulfonamide | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 28

Aqueous Suspension

| | |
|---|---|
| N—[(4-methoxy-6-methlpyrimidin-2-yl)aminocarbonyl]-2,2-dimethyl-1,3-benzodioxole-4-sulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 29

Solution

| | |
|---|---|
| N—[(4,6-dimethylpyrimidin-2-yl)aminocarbonyl]-2,2-dimethyl-1,3-benzodioxole-4-sulfonamide, sodium salt | 5% |
| water | 95% |

The salt is added directly to the water with stirring to produce the solution, which may then be packaged for use.

EXAMPLE 30

Low Strength Granule

| | |
|---|---|
| N—[(4,6-dimethyl-1,3,5-triazin-2-yl)aminocarbonyl]-2,2-dimethyl-1,3-benzodioxole-4-sulfonamide | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 31

Granule

| | |
|---|---|
| N—[(4,6-dimethoxypyrimidin-2-yl)aminocarbonyl]-2,2-dimethyl-1,3-benzodioxole-4-sulfonamide | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 32

High Strength Concentrate

| | |
|---|---|
| N—[(4,6-dimethoxy-1,3,5-triazin-2-yl)aminocarbonyl]-2,2-dimethyl-1,3-benzodioxole-4-sulfonamide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 33

Wettable Powder

| | |
|---|---|
| N—[(4-methoxy-6-methyl-1,3,5-triazin-2-yl)aminocarbonyl]-2,2-dimethyl-1,3-benzodioxole-4-sulfonamide | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 34

Wettable Powder

| | |
|---|---|
| N—[(4-methoxy-6-methylpyrimidin-2-yl)aminocarbonyl]-2,2-dimethyl-1,3-benzodioxole-4-sulfonamide | 40% |
| sodium ligninsulfonate | 20% |
| montmorillonite clay | 40% |

The ingredients are thoroughly blended, coarsely hammer-milled and then-air milled to produce particles essentially all below 10 microns in size. The material is reblended and then packaged.

EXAMPLE 35

Oil Suspension

| | |
|---|---|
| N—[(4,6 dimethlpyrimidin-2-yl)aminocarbonyl]-2,2-dimethyl-1,3-benzodioxole-4-sulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 36

Dust

| | |
|---|---|
| N—[(4,6-dimethoxypyrimidin-2-yl)aminocarbonyl]-2,2-dimethyl-1,3-benzodioxole-4-sulfonamide | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

Utility

The compounds of the present invention are powerful herbicides. They have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Alternatively, the subject compounds are useful for selective pre- or post-emergence weed control in crops, such as wheat, barley and rice.

The rates of application for the compounds of the invention are determined by a number of factors, including their use as selective or general herbicides, the crop species involved, the types of weeds to be controlled, weather and climate, formulations selected, mode of application, amount of foliage present, etc. In general terms, the subject compounds should be applied at levels of around 0.125 to 10 kg/ha, the lower rates being suggested for use on lighter soils and/or those having a low organic matter content, for selective weed control or for situations where only short-term persistence is required.

The compounds of the invention may be used in combination with any other commercial herbicide examples, of which are those of the triazine, triazole, uracil, urea, amide, diphenylether, carbamate and bipyridylium types.

The herbicidal properties of the subject compounds were discovered in a number of greenhouse tests. The test procedures and results follow.

Test A

Seeds of crabgrass (Digitaria sp.), barnyardgrass (*Echinochloa crusgalli*), wild oats (*Avena fatua*), sicklepod (*Cassia obtusifolia*), morningglory (Ipomoea sp.), cocklebur (Xanthium sp.), sorghum, corn, soybean, rice, wheat and nutsedge tubers (*Cyperus rotundus*) were planted in a growth medium and treated pre-emergence with a non-phytotoxic solvent solution of the compounds of Table A. At the same time, cotton having five leaves, bush beans with the third trifoliate leaf expanding, crabgrass and barnyardgrass with two leaves, wild oats with two leaves, sicklepod with three leaves, morningglory and cocklebur with four leaves, sorghum with four leaves, corn with four leaves, soybean with two leaves, rice with three leaves, wheat with one leaf, and nutsedge with three to five leaves were sprayed with a non-phytotoxic solvent solution of the compounds of Table A. Other containers of the above mentioned weeds and crops were treated pre- or post-emergence with the same non-phytotoxic solvent so as to provide a solvent control. A set of untreated control plants was also included for comparison. Pre-emergence and post-emergence treated plants and controls were maintained in a greenhouse for sixteen days, then all treated plants were compared with their respective controls and rated visually for response to treatment.

The following rating system was used:
0=no effect;
10=maximum effect;
C=chlorosis or necrosis;
D=defoliation;
E=emergence inhibition;
G=growth retardation;
H=formative effects;
U=unusual pigmentation;
I=increased chlorophyl; and
6Y=abscised buds or flowers.

Considering the low rates of application, the data clearly demonstrate the high herbicidal activity of the compounds tested.

Compounds

Compound 1
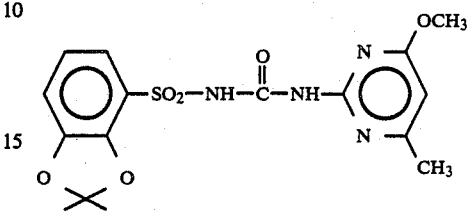

Compound 2
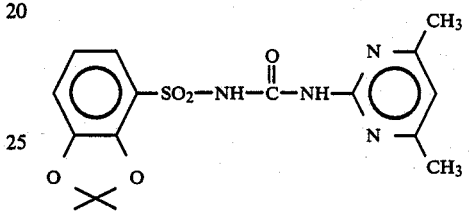

Compound 3
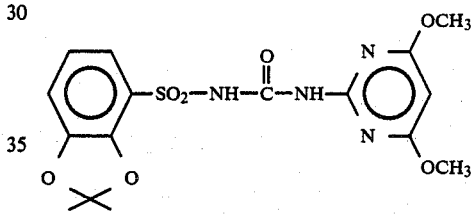

Compound 4
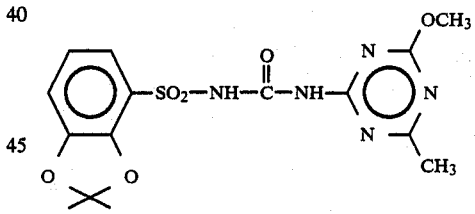

Compound 5
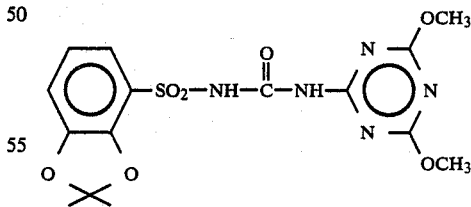

Compound 6
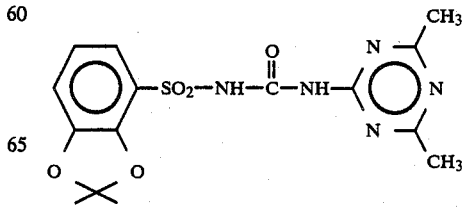

TABLE A

| Rate kg/ha | Cmpd. 1<br>0.4 | Cmpd. 1<br>0.1 | Cmpd. 2<br>0.05 | Cmpd. 2<br>0.4 | Cmpd. 3<br>0.05 | Cmpd. 3<br>0.4 | Cmpd. 4<br>0.05 | Cmpd. 5<br>0.05 | Cmpd. 6<br>.05 |
|---|---|---|---|---|---|---|---|---|---|
| POST-EMERGENCE | | | | | | | | | |
| Bush bean | 9C | 8D,9G,6Y | 3C,9G,6Y | 5C,9G,6Y | 7C,9G,6Y | 9C | 5C,9G,6Y | 9C | 0 |
| Cotton | 9C | 6C,9G | 3C,3H,8G | 4C,9G | 4C,3H,9G | 6C,9G | 4C,8G | 5C,9G | 0 |
| Morningglory | 10C | 9C | 2C,4G | 6C,9G | 5G | 5G | 10C | 10C | 2C,2H |
| Cocklebur | 9C | 9C | 2C,6G | 5C,9G | 5C,9G | 9C | 10C | 9C | 1C |
| Sicklepod | 9C | 6C,9G | 4C | 4C,6H | 5C,9G | 9C | 4C,9G | 9C | 0 |
| Nutsedge | 4C,9G | 9G,5X | 4G | 2C,9G | 2C,9G | 3C,9G | 6G | 0 | 0 |
| Crabgrass | 1C,9G | 2H,8G | 0 | 4G | 4G | 5G | 2C,8G | 6G | 0 |
| Barnyardgrass | 9C | 5C,9H | 2C,8H | 9H | 3C,9H | 9C | 4C,9H | 9H | 0 |
| Wild Oats | 3C,9G | 2C,9G | 2G | 2C,5G | 1C,6G | 2C,9G | 9G | 2C,9G | 0 |
| Wheat | 3C,9G | 0 | 0 | 0 | 3G | 1C,8G | 9G | 2G | 0 |
| Corn | 5U,9C | 3U,9G | 2C,8H | 2C,9H | 3C,9H | 1C,9H | 5U,9C | 3C,9G | 0 |
| Soybean | 9C | 9C | 2C,5G | 3C,8G | 5C,8H | 9C | 9C | 9C | 0 |
| Rice | 9C | 3C,9G | 0 | 5G | 1G | 1C,6G | 6C,9G | 2C,8G | 0 |
| Sorghum | 4U,9G | 9G | 2C,8H | 2C,9H | 2C,9G | 2C,9G | 5C,9G | 5C,9G | 0 |
| Sugar beet | | | | | | | | | 2C,7G |
| PRE-EMERGENCE | | | | | | | | | |
| Morningglory | 9H | 2C,9H | 5G | 9G | 2G | 7G | 10C | 8H | 0 |
| Cocklebur | 9H | 9H | 5H | — | 8H | 9H | 9H | 9H | 0 |
| Sicklepod | 9C | 9G | 4H | 7G | 8G | 9G | 2C,9G | 2C,9G | 0 |
| Nutsedge | 9G | 8G | 0 | 9G | 10E | 10E | 0 | 5G | 0 |
| Crabgrass | 3C,8G | 1C,6G | 0 | 0 | 0 | 2C,4G | 2C | 3G | 0 |
| Barnyardgrass | 5C,9H | 9H | 2C,4G | 2C,8H | 3C,9H | 9H | 3C,9H | 2C,8H | 0 |
| Wild Oats | 3C,9H | 2C,9G | 1C,3G | 2C,7G | 2C,6G | 3C,8H | 3C,9G | 2C,6G | 0 |
| Wheat | 2C,9G | 2C,9G | 0 | 7G | 2C,5G | 2C,8G | 1C,9G | 1C,6G | 0 |
| Corn | 10E | 5C,9H | 2C,6G | 2C,9H | 2C,9G | 5C,9H | 5C,9H | 8G | 0 |
| Soybean | 9H | 8H | 1C,1H | 2C | 7H | 9H | 9H | 3C,5H | 0 |
| Rice | 4C,9H | 3C,8H | 2C,3G | 2G | 2G | 6G | 5C,7H | 0 | 0 |
| Sorghum | 10E | 9H | 1C | 2C,7H | 10H | 6C,9H | 10H | 4C,9H | 0 |
| Sugar beet | | | | | | | | | 0 |

It is noted that Compound 6 has demonstrated low activity at a rate of 0.05 kg/ha. It is thought that at higher rates, activity would be improved.

Test B

Two plastic bulb pans were filled with fertilized and limed Fallsington silt loam soil. One pan was planted with corn, sorghum, Kentucky bluegrass and several grassy weeds. The other pan was planted with cotton, soybeans, purple nutsedge (*Cyperus rotundus*), and several broadleaf weeds. The following grassy and broadleaf weeds were planted: crabgrass (*Digitaria sanguinalis*), barnyardgrass (*Echinochloa crusgalli*), wild oats (*Avena fatua*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pensylvanicum*), pigweed (*Amaranthus retroflexus*), morningglory (*Ipomoea hederacea*), sicklepod (*Cassia obtusifolia*), teaweed (*Sida spinosa*), velvetleaf (*Abutilon theophrasti*), and jimsonweed (*Datura stramonium*). A 12.5 cm diameter plastic pot was also filled with prepared soil and planted with rice and wheat. Another 12.5 cm pot was planted with sugar beets. The above four containers were treated pre-emergence with several test compounds within the scope of the invention.

Twenty-eight days after treatment, the plants were evaluated and visually rated for response to the chemical treatments utilizing the rating system described previously for Test A. The data are summarized in Table B.

TABLE B

PRE-EMERGENCE ON FALLSINGTON SILT LOAM

| | Compound 1 | | Compound 2 | | | Compound 3 | | | | Compound 4 | | Compound 5 | |
|---|---|---|---|---|---|---|---|---|---|---|---|---|---|
| Rate kg/ha | .030 | .120 | .030 | 0.060 | .250 | .030 | .120 | 0.060 | 0.250 | 0.060 | 0.250 | 0.030 | 0.120 |
| Crabgrass | 0 | 0 | 0 | 0 | 0 | 0 | 2G | 2G | 2G | 2G | 2G | 2G | 5G |
| Barnyardgrass | 6G,3H | 9G,5H | 2G | 4G | 5G | 3G | 7G | 5G | 6G,5H | 6G | 8G | 6G | 8C |
| Sorghum | 6G,3H | 9G,5H | 3G | 3G | 6G | 8G | 8G,8C | 10C | 10C | 9G | 10C | 9G | 10C |
| Wild Oats | 3G | 6G,2C | 0 | 2G | 4G | 0 | 4G | 3G | 5G | 4G | 6G | 6G | 8G |
| Johnsongrass | 2H | 8G,5H | 2G | 2G | 5G,3H | 5G | 8G | 7G,5H | 8G,3C | 6G | 6G | 8G | 9G |
| Dallisgrass | 0 | 3G | 0 | 2G | 2G | 2G | 4G | 4G | 7G | 0 | 3G | 2G | 8G |
| Giant foxtail | 0 | 0 | 0 | 0 | 0 | 0 | 4G | 5G | 6G,2C | 0 | 2G | 5G | 9G |
| Ky. bluegrass | 0 | 4G | 0 | 4G | 5G | 3G | 9G | 7G | 8G | 4G | 8G | 5G | 8G |
| Cheatgrass | 3G | 6G,6C | 0 | 2G | 4G | 9G | 9G,9C | 9G,9C | 10C | 6G | 10C | 7G | 9G |
| Sugar beets | 6G | 7G,5C | 2G | 2G | 5G | 3G | 8G | 9G | 9G | 9G | 9G | 9G | 10C |
| Corn | 3G | 7G,5H | 0 | 0 | 7G,5H | 5G,5H | 10C | 8G,7H | 8G,8H | 9G,9C | 10C | 9G | 10C |
| Mustard | 9G,9C | 9G,9C | 5G | 8G | 9G,9C | 8G | 8G,8C | 10C | 10C | 9G,9C | 10C | 10C | 10C |
| Cocklebur | 6G,3H | 7G,5H | 0 | 0 | 7G,3H | 5G,3C | 7G,5C | 6G,5H | 7G,5H | 8G,7H | 8G,7H | 8G | 9G |
| Pigweed | 0 | 5G | — | — | — | — | — | 10C | — | — | — | — | — |
| Nutsedge | 5G | 7G | 0 | 0 | 4G | 10C | 10C | 10C | 10C | 5G | 5G | 2G | 6G |
| Cotton | 3G | 8G,5H | 2G | 6G | 6G | 0 | 3G | 0 | 3G,3H | 8G | 9G | 7G | 9G |
| Morningglory | 3G | 5G,3C | 0 | 0 | 3G | 3G | 3G | 0 | 2G | 7G | 8G | 7G | 8G |
| Sicklepod | 0 | 4G,3C | 0 | 0 | 0 | 3G | 7G | 2G | 5G | 3G | 6G | 0 | 6G |
| Teaweed | 2C | 5G,5H | 0 | 0 | 7G | 6G | 8G | 5G | 6G | 2G | 2G | 5G | 8G |
| Velvetleaf | 3G | 4G,3H | — | — | — | — | — | 3G | 8G | 2G | 3G | 7G | 9G |
| Jimsonweed | 3G | 5G | 0 | 0 | 2G | 2G | 5G | 0 | 2G | 2G | 6G | 8G | 9G |
| Soybean | 2H | 6G,5H | 0 | 0 | 0 | 0 | 0 | 2G,2C | 4G,5H | 7G,5C | 8G | 5G,3H | 9G |

TABLE B-continued

| | PRE-EMERGENCE ON FALLSINGTON SILT LOAM | | | | | | | | | | | |
|---|---|---|---|---|---|---|---|---|---|---|---|---|
| | Compound 1 | | Compound 2 | | | Compound 3 | | | Compound 4 | | Compound 5 | |
| Rate kg/ha | .030 | .120 | .030 | .060 | .250 | .030 | .120 | 0.060 | 0.250 | 0.060 | 0.250 | 0.030 | 0.120 |
| Rice | 5G | 6G | 2G | 4G | 5G | 2G | 6G | 3G | 7G | 7G | 8G | 6G | 8G |
| Wheat | 0 | 3G | 0 | 0 | 0 | 0 | 0 | 5G | 6G | 3G | 4G | 2G | 4G |

Test C

Two ten-inch in diameter plastic pans lined with polyethylene liners were filled with the prepared Fallsington silt loam soil. One pan was planted with seeds of wheat (*Triticum aestivum*), barley (*Hordeum vulgare*), wild oats (*Avena fatua*), downy brome (*Bromus tectorum*), cheatgrass (*Bromus secalinus*), blackgrass (*Alopecurus myosuroides*), annual bluegrass (*Poa annua*), green foxtail (*Setaria viridis*), quackgrass (*Agropyron repens*), Italian ryegrass (*Lolium multiflorum*) and ripgut brome (*Bromus rigidus*). The other pan was planted with seeds of Russian thistle (*Salsola kali*), tansy mustard (*Descuraina pinnata*), Galium aparine, tumble mustard (*Sisymbrium altissium*) kochia (*Kochia scoparia*), shepherd's purse (*Capsella bursapastoris*), Matricaria inodora, black nightshade (*Solanum nigrum*), yellow rocket (*Barbarea vulgaris*), rapeseed and wild buckwheat (*Polygonum convolvulus*). The above two pans were treated pre-emergence. At the same time two pans in which the above plant species were growing were treated post-emergence. Plant height at the time of treatment ranged from 1–15 cm depending on plant species.

The test compounds were diluted with a non-phytotoxic solvent and sprayed over-the-top of the pans at two rates of application. An untreated control and a solvent alone control were included for comparison. All treatments were maintained in the greenhouse for 20 days at which time the treatments were compared to the controls and the effects visually rated. The recorded data are presented in Table C. The data indicate that the compounds tested have potential utility for the pre- and/or post-emergence weed control of certain weed species in cereal crops such as wheat and barley.

Test D

Two compounds from within the scope of the invention were dissolved in a non-phytotoxic solvent and applied to rice which had been transplanted three days previously into simulated paddies. The paddies also contained plantings of barnyardgrass, water chestnut and arrowhead, serious weed problems in rice fields. The test was maintained in a greenhouse. Plant response ratings were made five to eight weeks after application utilizing the rating system as described for Test A. The data are summarized in Table D. At least one of the compounds tested has utility for selective weed control in rice.

TABLE D

| Cmpd. | Rate g/ha | Rice | Barnyard-grass | Water Chestnut | Arrow-head |
|---|---|---|---|---|---|
| 1 | 10 | 1G | 7H | 3G | 9G |
| | 20 | 4G, 5I | 9H | 7G | 9G, 4C |
| | 40 | 7G, 5I | 10C | 9G | 10E |
| | 80 | 8G, 5I | 10C | 10C | 10E |
| 2 | 10 | 0 | 0 | 0 | 0 |
| | 40 | 0 | 4G | 0 | 0 |
| 3 | 10 | 0 | 9E | 0 | 5G |
| | 40 | 0 | 9E | 8G | 10G |
| 3 | 10 | 0 | 8C | 7G | 10E |
| | 20 | 0 | 9C | 8G | 10G |
| | 40 | 3G, 5I | 9C | 9G, 3C | 10E |
| | 80 | 3G, 5I | 9C | 10G, 1C | 10E |
| | 100 | 4G, 5I | 9C | 10G, 4C | 10G, 5C |
| | 120 | 3G, 5I | 10C | 10C | 10G, 6C |
| 4 | 20 | 3G, 5I | 5G | 9G | 0 |
| | 40 | 4G, 5I | 9C | 9G | 0 |
| | 80 | 7G, 5I | 10C | 10G, 2C | 2G, 2H |
| 5 | 20 | 6G, 5I | 9C | 0 | 9G |
| | 40 | 7G, 5I | 9C | 7G | 10G |
| | 80 | 8G, 3C | 9G | 1G | 10G |

TABLE C

| | Compound 1 | | | | Compound 3 | | | |
|---|---|---|---|---|---|---|---|---|
| | Pre-Emergence | | Post-Emergence | | Pre-Emergence | | Post-Emergence | |
| Rate kg/ha | 0.06 | 0.015 | 0.06 | 0.015 | 0.015 | 0.06 | 0.015 | 0.06 |
| wheat | 1C,2G | 1C,1G | 3G | 0 | 6G | 7G | 2G | 6G |
| barley | 3G | 2G | 3G | 0 | 4G | 6G | 4G | 6G |
| wild oats | 1C,5G | 4G | 5G | 3G | 5G | 8G | 3G | 7G |
| downy brome | 2C,6G | 4G | 8G | 5G | 8G | 8G | 0 | 4G |
| cheatgrass | 9C,9G | 2C,8G | 8C,9G | 1C,7G | 5G | 10C | 4G | 7G |
| blackgrass | 8C,7G | 3C,6G | 9C,9G | 6G | 1C,8G | 2C,9G | 5G | 2C,8G |
| annual bluegrass | 1C,6G | 1C,5G | 5C,8G | 7G | 8G | 9G | 5G | 8G |
| green foxtail | 2G | 0 | 1C,2G | 0 | 0 | 5G | 3G | 3G |
| quackgrass | 8G | 6G | 8G | 5G | 8G | 9G | 7G | 8G |
| Italian ryegrass | 6G | 1C,5G | 5G | 5G | 4G | 8G | 4G | 6G |
| ripgut brome | 7G | 1C,5G | 3C,8G | 6G | 7G | 2C,8G | 6G | 8G |
| Russian thistle | 2C,2G | 1C,1G | 7C,7C | 2C,3G | 0 | 1C | 3G | 4G |
| tansy mustard | 9G | 10E | 10C | 10C | 9G | 2C,9G | 10C | 10C |
| *Galium aparine* | 9C,8G | 1C,8G | 8G | 6G | 9G | 2C,9G | 5C,9G | 10C |
| tumble mustard | 10C | 8G | 9C,9G | 9C,9G | 9G | 10C | 10C | 10C |
| kochia | 5G | 2G | 2G | 0 | 3G | 6G | 5G | 5G |
| shepherd's purse | 10C | 9C,9G | 9C,9G | 10C | 3C,9G | 9C,9G | 10C | 10C |
| *Matricaria inodora* | 9G | 9G | 10C | 7C,8G | 9G | 3C,9G | 10C | 10C |
| black nightshade | 8G | 1G | 3G | 0 | 7G | 7G | 2C | 4G |
| yellow rocket | 9C,9G | 9G | 9C,9G | 8G | 9G | 2C,9G | 10C | 10C |
| rapeseed | 9C,9G | 5C,9G | 10C | 10C | 2C,9G | 2C,9G | 9C,9G | 10C |
| wild buckwheat | 5C,8G | 1C,5G | 4C,7G | 2C,7G | 7G | 2C,8G | 2C,8G | 7C,9G |

Test E

The test chemicals, dissolved in a non-phytotoxic solvent, were applied in an overall spray to the foliage and surrounding soil of selected plant species. One day after treatment, plants were checked for rapid burn injury. Approximately fourteen days after treatment all species were visually compared to untreated controls and rated for response to treatment. The rating system was as described previously for Test A. The data are presented in Table E.

All plant species were seeded in Woodstown sandy loam soil and grown in a greenhouse. The following species were grown in soil contained in plastic pots (25 cm diameter by 13 cm deep): soybeans, cotton, alfalfa, corn, rice, wheat, sorghum, velvetleaf (*Abutilon theophrasti*), sesbania (*Sesbania exaltata*), sicklepod (*Cassia obtusifolia*), morningglory (*Ipomoea hederacea*), jimsonweed (*Datura stramonium*), cocklebur (*Xanthium pensylvanicum*), crabgrass (Digitaria spp.), nutsedge (*Cyperus rotundus*), barnyardgrass (*Echinochloa crusgalli*), giant foxtail (*Setaria faberii*), and wild oats (*Avena fatua*). The following species were grown in soil in a paper cup (12 cm diameter by 13 cm deep): sunflower, sugar beets, and rape. All plants were sprayed approximately 14 days after planting. Additional plant species, such as johnsongrass and field bindweed, are sometimes added to this standard test in order to evaluate unusual selectivity.

Several of the compounds tested by this procedure are useful for the post-emergence control of weeds in wheat and rice.

TABLE E

| | Over-the-Top Soil/Foliage Treatment | | | | | | | |
|---|---|---|---|---|---|---|---|---|
| | Compound 1 | | Compound 2 | | | Compound 5 | | |
| Rate g/ha | 125 | 31 | 62 | 15 | 4 | 62 | 15 | 4 |
| Soybeans | 9G,8C | 10C | 4G,4C | 2G,3C | 1G,1C | 9C | 9G | 9G |
| Velvetleaf | 9G,9C | 8G,2C | 9G,6C | 8G,4C | 4G | 8G | 10C | 4G |
| Sesbania | 9G,4C | 8G,4C | 9G,5C | 8G,4C | 8G,4C | 8G | 6G | 3G |
| Sicklepod | 4G,3C | 4G,4C | 0 | 0 | 0 | 2G | 2G | 1G |
| Cotton | 10C | 10C,4C | 9G | 9G | 8G | 9G | 8G | 8G |
| Morninglory | 9G,8C | 7G | 8G,7C | 7G,2C | 2C | 6G,5C | 0 | 0 |
| Alfalfa | 9G,5C | 8G,5C | 8G | 6G | 0 | 7C,4G | 9G | 4C,6G |
| Jimsonweed | 9G | 4C | 0 | 0 | 0 | 9G | 8G | 8G |
| Cocklebur | 9G,2C | 9G,2C | — | 0 | 0 | 7G | 6G | 6G |
| Sunflower | 10C | 10C | 9G,5C | 9G,2C | 9G,2C | 10C | 10C | 10C |
| Rape | 10C | 10C | 9G,4C | 9G | 7G,4C | 8G | 8G | 8G |
| Sugar beets | 8G | 5G | 8G | 6G | 6G | 10C | 5G | 4G |
| Corn | 9G,8C | 7C | 8G,5H | 5G,2C | 0 | 10C | 10C | 8G |
| Crabgrass | 0 | 0 | 0 | 0 | 0 | 8G | 2G | 2G |
| Rice | 1G | 0 | 0 | 0 | 0 | 2G | 2G | 1G |
| Nutsedge | 5G | 0 | 9G | 0 | 0 | 0 | 0 | 0 |
| Barnyardgrass | 7G | 6G | 7G,3C | 5G | 2G | 5G | 4G | 3G |
| Wheat | 2G | 0 | 0 | 0 | 0 | 4G | 2G | 0 |
| Giant foxtail | 7G | 0 | 6G | 4G | 2G | 3G | 2G | 0 |
| Wild Oats | 6G | 2G | 0 | 0 | 0 | 2G | 1G | 0 |
| Sorghum | 5G | 5G | 5G,3C | 3G | 0 | 9C | 8C | 8G |
| Johnsongrass | 8G,8C | 3G | 4G | 2G | 0 | 8G | 5C,6G | 5G,4C |
| Field Bindweed | 0 | 3G | 4G | 0 | 0 | 0 | 0 | 0 |

What is claimed is:

1. A compound selected from

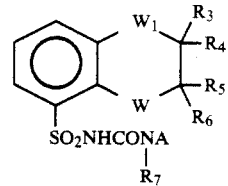

wherein
W is O;
$W_1$ is O;
$R_3$, $R_4$, $R_5$, $R_6$ and $R_7$ are independently H or $CH_3$;
A is

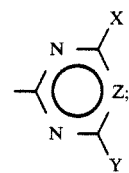

X is $CH_3$, $OCH_3$, or Cl;
Y is $C_2H_5$, $CH_3$, $OCH_3$, $OC_2H_5$, $CH_2OCH_3$, $NH_2$, $NHCH_3$, $SCH_3$, $N(CH_3)_2$, $CH(OCH_3)_2$ or

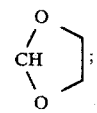

and
Z is N.

2. Compounds of claim 1 Formula II where W and $W_1$ have identical values.

3. Compounds of claim 2 where
A is

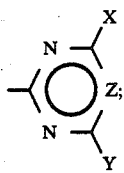

and R$_7$ is H.

4. Compounds of claim 3 where Y is CH$_3$ or OCH$_3$.

5. A composition suitable for controlling the growth of undesired vegetation which comprises an effective amount of a compound of claim 1 and at least one of the following: surfactant, solid or liquid diluent.

6. A composition suitable for controlling the growth of undesired vegetation which comprises an effective amount of a compound of claim 2 and at least one of the following: surfactant, solid or liquid diluent.

7. A composition suitable for controlling the growth of undesired vegetation which comprises an effective amount of a compound of claim 3 and at least one of the following: surfactant, solid or liquid diluent.

8. A method for controlling the growth of undesired vegetation which comprises applying to the locus to be protected an effective amount of a compound of claim 1.

9. A method for controlling the growth of undesired vegetation which comprises applying to the locus to be protected an effective amount of a compound of claim 2.

10. A method for controlling the growth of undesired vegetation which comprises applying to the locus to be protected an effective amount of a compound of claim 3.

* * * * *